(12) United States Patent
Freeman et al.

(10) Patent No.: US 11,261,251 B2
(45) Date of Patent: Mar. 1, 2022

(54) HUMAN ANTI-PD-1, PD-L1, AND PD-L2 ANTIBODIES AND USES THEREFOR

(71) Applicants: DANA-FARBER CANCER INSTITUTE, INC., Boston, MA (US); EMORY UNIVERSITY, Atlanta, GA (US)

(72) Inventors: Gordon J. Freeman, Brookline, MA (US); Rafi Ahmed, Atlanta, GA (US); Timothy D. Jones, Cambridgeshire (GB); Francis J. Carr, Aberdeenshire (GB); James P. Gregson, Essex (GB)

(73) Assignees: DANA-FARBER CANCER INSTITUTE, INC., Boston, MA (US); EMORY UNIVERSITY, Atlanta, GA (US)

(*) Notice: Subject to any disclaimer, the term of this patent is extended or adjusted under 35 U.S.C. 154(b) by 292 days.

(21) Appl. No.: 16/506,840

(22) Filed: Jul. 9, 2019

(65) Prior Publication Data
US 2020/0172616 A1  Jun. 4, 2020

Related U.S. Application Data

(60) Division of application No. 15/995,584, filed on Jun. 1, 2018, now Pat. No. 10,370,448, which is a division of application No. 14/822,651, filed on Aug. 10, 2015, now Pat. No. 10,011,656, which is a division of application No. 13/802,172, filed on Mar. 13, 2013, now Pat. No. 9,102,727, which is a continuation of application No. 13/120,406, filed as application No. PCT/US2009/058475 on Sep. 25, 2009, now Pat. No. 8,552,154.

(60) Provisional application No. 61/100,534, filed on Sep. 26, 2008.

(51) Int. Cl.
| | | |
|---|---|---|
| C07K 16/28 | (2006.01) | |
| A61K 39/395 | (2006.01) | |
| A61P 35/00 | (2006.01) | |
| A61K 39/00 | (2006.01) | |

(52) U.S. Cl.
CPC ...... *C07K 16/2803* (2013.01); *C07K 16/2818* (2013.01); *C07K 16/2827* (2013.01); *A61K 2039/505* (2013.01); *C07K 2317/21* (2013.01); *C07K 2317/24* (2013.01); *C07K 2317/34* (2013.01); *C07K 2317/74* (2013.01); *C07K 2317/76* (2013.01); *C07K 2317/92* (2013.01); *Y02A 50/30* (2018.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,474,893 A | 10/1984 | Reading |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,790,824 A | 12/1988 | Morrow et al. |
| 4,816,567 A | 3/1989 | Cabilly |
| 4,873,316 A | 10/1989 | Meade et al. |
| 4,941,880 A | 7/1990 | Burns |
| 5,064,413 A | 11/1991 | McKinnon et al. |
| 5,223,409 A | 6/1993 | Ladner et al. |
| 5,225,539 A | 7/1993 | Winter |
| 5,272,071 A | 12/1993 | Chappel |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg |
| 5,625,126 A | 4/1997 | Ladner et al. |
| 5,629,204 A | 5/1997 | Honjo et al. |
| 5,633,425 A | 5/1997 | Lonberg et al. |
| 5,661,016 A | 8/1997 | Lonberg et al. |

(Continued)

FOREIGN PATENT DOCUMENTS

| | | |
|---|---|---|
| EP | 0125023 A1 | 11/1984 |
| EP | 0171496 A2 | 2/1986 |

(Continued)

OTHER PUBLICATIONS

Aalberse, R.C. et al. (2002). "IgG4 Breaking the Rules," Immunology 105:9-19.

Agata, Y. et al. (1996). "Expression of the PD-1 Antigen on the Surface of Stimulated Mouse T and B Lymphocytes," International Immunology 8(5):765-772.

Aicher, A. et al. (2000). "Characterization of Human Inducible Costimulator Ligand Expression and Function," J. Immunol. 164:4689-4696.

(Continued)

*Primary Examiner* — Ilia I Ouspenski
(74) *Attorney, Agent, or Firm* — Morrison & Foerster LLP

(57) ABSTRACT

The present invention is based, in part, on the identification of novel human anti-PD-1, PD-L1, and PD-L2 antibodies. Accordingly, the invention relates to compositions and methods for diagnosing, prognosing, and treating conditions that would benefit from modulating PD-1, PD-L1, and/or PD-L2 activity (e.g., persistent infections diseases, autoimmune diseases, asthma, transplant rejection, inflammatory disorders and tumors) using the novel human anti-PD-1, PD-L1, and PD-L2 antibodies described herein.

19 Claims, 42 Drawing Sheets

Specification includes a Sequence Listing.

(56) References Cited

U.S. PATENT DOCUMENTS

| | | | |
|---|---|---|---|
| 5,733,743 A | 3/1998 | Johnson et al. |
| 5,770,429 A | 6/1998 | Lonberg et al. |
| 5,789,650 A | 8/1998 | Lonberg et al. |
| 5,798,229 A | 8/1998 | Strittmatter et al. |
| 5,814,318 A | 9/1998 | Lonberg et al. |
| 5,871,907 A | 2/1999 | Winter et al. |
| 5,874,299 A | 2/1999 | Lonberg et al. |
| 5,877,397 A | 3/1999 | Lonberg et al. |
| 5,959,084 A | 9/1999 | Ring et al. |
| 6,495,137 B1 | 12/2002 | Mezes et al. |
| 6,632,927 B2 | 10/2003 | Adair et al. |
| 6,803,192 B1 | 10/2004 | Chen |
| 7,029,674 B2 | 4/2006 | Carreno et al. |
| 7,105,328 B2 | 9/2006 | Wood et al. |
| 8,552,154 B2 | 10/2013 | Freeman et al. |
| 9,102,727 B2 | 8/2015 | Freeman et al. |
| 10,011,656 B2 | 7/2018 | Freeman et al. |
| 10,370,448 B2 | 8/2019 | Freeman |
| 2002/0164600 A1 | 11/2002 | Freeman et al. |
| 2005/0004354 A1 | 1/2005 | Salfeld et al. |
| 2005/0129690 A1 | 6/2005 | Bowdish |
| 2005/0226867 A1 | 10/2005 | Iida |
| 2005/0255102 A1 | 11/2005 | Violette et al. |
| 2007/0122378 A1 | 5/2007 | Freeman et al. |
| 2008/0004417 A1 | 1/2008 | Jansen et al. |
| 2008/0166756 A1 | 7/2008 | Tsuchiya et al. |
| 2010/0092457 A1 | 4/2010 | Aburatani et al. |
| 2011/0271358 A1 | 11/2011 | Freeman et al. |
| 2013/0291136 A1 | 10/2013 | Freeman et al. |
| 2016/0137731 A1 | 5/2016 | Freeman et al. |
| 2016/0311903 A1 | 10/2016 | West et al. |

FOREIGN PATENT DOCUMENTS

| | | | |
|---|---|---|---|
| EP | 0173494 A2 | 3/1986 |
| EP | 0184187 A2 | 6/1986 |
| EP | 0264166 A1 | 4/1988 |
| EP | 1907424 B1 | 7/2015 |
| JP | 2004-501631 A | 1/2004 |
| JP | 2006-521783 A | 9/2006 |
| JP | 2007-504804 A | 3/2007 |
| JP | 2008-509656 A | 4/2008 |
| KR | 10-2008-0045674 A | 5/2008 |
| WO | 1986/01533 A1 | 3/1986 |
| WO | 1987/002671 A1 | 5/1987 |
| WO | 1990/02809 A1 | 3/1990 |
| WO | 1991/06667 A1 | 5/1991 |
| WO | 1991/17271 A1 | 11/1991 |
| WO | 1992/01047 A1 | 1/1992 |
| WO | 1992/03918 A1 | 3/1992 |
| WO | 1992/09690 A1 | 6/1992 |
| WO | 1992/15679 A1 | 9/1992 |
| WO | 1992/18619 A1 | 10/1992 |
| WO | 1992/20791 A1 | 11/1992 |
| WO | 1992/22645 A1 | 12/1992 |
| WO | 1993/01288 A1 | 1/1993 |
| WO | 1993/12270 A1 | 6/1993 |
| WO | 1994/02610 A1 | 2/1994 |
| WO | 1994/25585 A1 | 11/1994 |
| WO | 1994/29346 A1 | 12/1994 |
| WO | 1995/03832 A1 | 2/1995 |
| WO | 1998/24884 A1 | 6/1998 |
| WO | 1998/38216 A1 | 9/1998 |
| WO | 1999/045962 A1 | 9/1999 |
| WO | 2002/00730 A2 | 1/2002 |
| WO | 2002/43478 A2 | 6/2002 |
| WO | 2004/056875 A1 | 7/2004 |
| WO | 2005/011376 A2 | 2/2005 |
| WO | 2005/121180 A2 | 12/2005 |
| WO | 2006/067913 A1 | 6/2006 |
| WO | 2006/082406 A2 | 8/2006 |
| WO | 2006/121168 A1 | 11/2006 |
| WO | 2006/133396 A2 | 12/2006 |
| WO | 2007/005874 A2 | 1/2007 |
| WO | 2008/020586 A1 | 2/2008 |
| WO | 2008/044032 A2 | 4/2008 |
| WO | 2008/083174 A2 | 7/2008 |

OTHER PUBLICATIONS

Allen, T.M. et al. (Jan. 15, 1998). "Characterization of the Peptide Binding Motif of a Rhesus MHC Class I Molecule (Mamu-A*01) that Binds an Immunodominant CTL Epitope From Simian Immunodeficiency Virus," J. Immunol. 160:6062-6071.

Allen, T.M. et al. (Sep. 21, 2000). "Tat-Specific Cytotoxic T Lymphocytes Select for SIV Escape Variants During Resolution of Primary Viraemia," Nature 407(2):386-390.

Allison, J.P. et al. (Nov. 10, 1995). "The Yin and Yang of T Cell Costimulation," Science 270:932-933.

Almagro, J.C. et al. (Jan. 1, 2008). "Humanization of Antibodies," Frontiers in Bioscience 13:1619-1633.

Altschul, S.F. et al. (1990). "Basic Local Alignment Search Tool," J. Mol. Biol. 215: 403-410.

Altschul, S.F. et al. (1997). "Gapped BLAST and PSI-BLAST: A New Generation of Protein Database Search Programs," Nucleic Acids Res. 25(17):3389-3402.

Amann, E. et al. (1988). "Tightly Regulated tac Promoter Vectors Useful for the Expression of Unfused and Fused Proteins in *Escherichia coli*," Gene 69:301-315.

Amara, R.R. et al. (Apr. 6, 2001). "Control of a Muscosal Challenge and Prevention of AIDS by a Multiprotein DNA/MVA Vaccine," Science 292:69-74.

Armitage, R.J. et al. (May 7, 1992). "Molecular and Biological Characterization of a Murine Ligand for CD40," Nature 357:80-82.

Arnon, R. et al. (1985). "Monoclonal Antibodies for Immunotargeting of Drugs in Cancer Therapy", Monoclonal Antibodies and Cancer Therapy, Reisfeld, R.A. et al. eds., Alan R. Liss, Inc., New York, New York, pp. 243-256.

Azuma, M. et al. (Nov. 4, 1993). "B70 Antigen is a Second Ligand for CTLA-4 and CD28," Nature 366:76-79.

Baldari, C. et al. (1987). "A Novel Leader Peptide Which Allows Efficient Secretion of a Fragment of Human Interleukin 1β in *Saccharomyces cerevisiae*," EMBO J. 6(1):229-234.

Banerji, J. et al. (Jul. 1983) "A Lymphocyte-Specific Cellular Enhancer Is Located Downstream of the joining Region in Immunoglobulin Heavy Chain Genes," Cell 33:729-740.

Barbas, III, C.F. et al. (Sep. 1991). "Assembly of Combinatorial Antibody Libraries on Phage Surfaces: The Gene III Site," Proc. Natl. Acad. Sci. USA 88:7978-7982.

Baskar, S. et al. (Jun. 1993). "Constitutive Expression of B7 Restores Immunogenicity of Tumor Cells Expressing Truncated Major Histocompatibility Complex II Molecules," Proc. Natl. Acad. Sci. 90:5687-5690.

Beerli, R.R. et al. (Oct. 28, 1994). "Autocrine Inhibition of the Epidermal Growth Factor Receptor by Intracellular Expression of a Single-Chain Antibody," Biochem. Biophys. Res. Commun. 204(2):666-672.

Beerli, R.R. et al. (Sep. 30, 1994). "Intracellular Expression of Single Chain Antibodies Reverts ErbB-2 Transformation," J. Biol. Chem. 269(39):23931-23936.

Beidler, C.B. et al. (Dec. 1, 1988). "Cloning and High Level Expression of a Chimeric Antibody With Specificity for Human Carcinoembryonic Antigen," J. Immunol. 141 (11):4053-4060.

Berge et al. (1977). "Pharmaceutical Salts," J. Pharm. Sci. 66(1):1-19.

Berger, S.L. (1987), "Isolation of Cytoplamic RNA: Ribonucleoside-Vanadyl Complexes," Methods in Enzymology 152:227-234.

Better, M. et al. (May 20, 1988). "*Escherichia coli* Secretion of an Active Chimeric Antibody Fragment," Science 240:1041-1043.

Biocca, S. et al. (1990). "Expression and Targeting of Intracellular Antibodies in Mammalian Cells," EMBO J. 9 (1):101-108.

Biocca, S. et al. (Apr. 12, 1994). "Intracellular Immunization With Cytosolic Recombinant Antibodies," Bio/Technology 12:396-399.

Bird, R.E. et al. (Oct. 1988). "Single-Chain Antigen-Binding Proteins," Science 242:423-426.

(56) References Cited

OTHER PUBLICATIONS

Bloeman, P.G.M. et al. (1995). "Adhesion Molecules: A New Target for Immunoliposome-Mediated Drug Delivery," FEBS Lett. 357:140-144.
Bluestone, J.A. (Jun. 1995). "New Perspectives of CD28-B7-Mediated. Minireview T Cell Costimulation," Immunity 2:555-559.
Boussiotis, V.A et al. (Nov. 1, 1993). "B7 But Not Intercellular Adhesion Molecule-1 Costimulation Prevents the Induction of Human Alloantigen-Specific Tolerance," J. Exp. Med. 178:1753-1763.
Briscoe, P. et al. (Mar. 1, 1995). "Delivery of Superoxide Dismutase to Pulmonary Epithelium Via pH-Sensitive Liposomes," Am. J. Physiol. 268(3):L374-L380.
Brodie, D. et al. (Mar. 10, 2000). "LICOS, A Primordial Costimulatory Ligand,?" Curr. Biol. 10(6):333-336.
Brown, A.J. et al. (Feb. 1, 2003). "Blockade of Programmed Death-1 Ligands on Dendritic Cells Enhances T Cell Activation and Cytokine Production," The Journal of Immunology 170(30):1257-1266.
Brown, J.P. et al. (Aug. 1981). "Structural characterization of Human Melanoma-Associated Antigen p97 With Monoclonal Antibodies," The Journal of Immunology 127(2):539-546.
Brown, J.P. et al. (Jun. 10, 1980). "Protein Antigens of Normal Malignant Human Cells Identified by Immunoprecipitation with Monoclonal Antibodies," J. Biol. Chem. 255(11):4980-4983.
Brunet, J-F. et al. (Jul. 16, 1987). "A New Member of the Immunogobulin Superfamily—CTLA-4," Nature 328:267-270.
Butte, M.J. et al. (Jul. 2007). "Programmed Dealth-1 Ligand 1 Interacts Specifically With the B7-1 Costimulatory Molecule to Inhibit T Cell Responses," Immunity 27:111-122.
Byrne, G.W. et al. (Jul. 1989). "Multiplex Gene Regulation: A Two-Tiered Approach to Transgene Regulation in Transgenic Mice," Proc. Natl. Acad. Sci. USA 86:5473-5477.
Calame, K. et al. (1988). "Transcriptional Controlling Elements in the Immunoglobulin and T Cell Receptor Loci," Adv. Immunol. 43:235-275.
Camper, S.A. et al.(1989). "Postnatal Repression of the a-Fetoprotein Gene is Enhancer Independent," Genes Dev. 3:537-546.
Capel, P.J.A. et al. (1994). "Heterogeneity of human IgG Fc Receptors," Immunomethods 4:25-34.
Carlson, J.R. (Aug. 1993). "A New Use For Intracellular Antibody Expression: Inactivation of Human Immunodeficiency Virus Type 1," Proc. Natl. Acad. Sci. USA 90:7427-7428.
Carlson, J.R. (Jun. 1988). "A New Means of Inducibly Inactivating A Cellular Protein," Mol. Cell. Biol. 8 (6):2638-2646.
Chaiken, I.M. (Sep. 1981). "Semisynthetic Peptides and Proteins," CRC Crit. Rev. Biochem. 11(3):255-301.
Chemnitz, J.M. et al. (2004). "SHP-1 and SHP-2 Associate With Immunoreceptor Tyrosine-Based Switch Motif of Programmed Death 1 Upon Primary Human T Cell Simulation, But Only Receptor Ligation Prevents T Cell Activation," J. Immunol. 173:945-954.
Chen, J. et al. (1993). "B Cell Development in Mice That Lack One or Both Immunoglobulin κ Light Chain Genes," EMBO J. 12(3):821-830.
Chen, J. et al. (1993). "Immunoglobulin Gene Rearrangement in B Cell Deficient Mice Generated by Targeted Deletion of the JH Locus," International Immunology 5(6):647-656.
Chen, L. et al. (Dec. 24, 1992). "Costimulation of Antitumor Immunity by the B7 Counterreceptor for the T Lymphocyte Molecules CD28 and CTLA-4," Cell 71:1093-1102.
Chen, S-Y. et al. (1994). "Intracellular Antibodies as a New Class of Therapeutic Molecules for Gene Therapy," Hum. Gene Ther. 5:595-601.
Chen, S-Y. et al. (Jun. 1994). "Combined Intra- and Extracellular Immunization Against Human Immunodeficiency Virus Type 1 Infection With A Human Anti-gp120 Antibody," Proc. Natl. Acad. Sci. USA 91:5932-5936.
Choi, T.K. et al. (Jun. 1993). "Transgenic Mice Containing A Human Heavy Chain Immunoglobulin Gene Fragment Cloned in a Yeast Artificial Chromosome," Nature Genetics 4:117-123.
Chothia, C. (1987). "Canonical Structures for the Hypervariable Regions of Immunoglobulins," J. Mol. Biol. 196:901-917.
Church, G.M. et al. (Apr. 1984). "Genomic Sequencing. DNA Methylation/UV Crosslinking/Filter Hybridization/Immunoglobulin Genes," Proc. Natl. Acad. Sci. USA 81:1991-1995.
Clackson, T. et al. (Aug. 15, 1991). "Making Antibody Fragments Using Phage Display Libraries," Nature 352:624-628.
Clarke et al. (Apr. 1, 1990). "V region gene usage and somatic mutation in the primary and secondary responses to influenza virus hemagglutinin," J. Immunol. 144(7):2795-2801.
Cole, S.P.C. et al. (1985). "The EBV-Hybridoma Technique and Its Application to Human Lung Cancer," Monoclonal Antibodies and Cancer Therapy pp. 77-96.
Daeron, M. (1997). "Fc Receptor Biology," Annu. Rev. Immunol. 15:203-234.
Dehaas, M. et al. (1995). "Fcy Receptors of Phagocytes," J. Lab. Clin. Med. 126:330-341.
Dorfman, D. (Jul. 2006). "Programmed Death-1 (PD-1) is a Marker of Germinal Center-Associated T Cells and Angioimmunoblastic T-Cell Lymphoma," Am. J. Surg. Pathol. 30(7):802-810.
Duan, L. et al. (May 1994). "Potent Inhibition of Human Immunodeficiency Virus Type 1 Replication by an Intracellular Anti-Rev Single-Chain Antibody," Proc. Natl. Acad. Sci. USA 91:5075-5079.
Dustin, M. I. et al. (Feb. 1989). "Correlation of CD2 Binding and Functional Properties of Multimeric and Monomeric Lymphocyte function-Associated Antigen 3," J. Exp. Med. 169:503-517.
Edlund, T. et al. (Nov. 22, 1985). "Cell-Specific Expression of the Rat Insulin Gene: Evidence For Role of Two Distinct 5' Flanking Elements," Science 230:912-916.
Extended European Search Report dated Jan. 25, 2017, for European Patent Application No. 16173372.0, filed on Sep. 25, 2009, 10 pages.
Extended European Search Report dated Jul. 3, 2019, for European Patent Application No. 18175924.2, filed on Sep. 25, 2009, 10 pages.
Fishwild, D. et al. (Jul. 1996). "High-Avidity Human IgGK Monoclonal Antibodies From a Novel Strain of Minilocus Transgenic Mice," Nature Biotechnology 14:845-851.
Fitz, L.J. et al. (1997). "Characterization of Murine Flt4 Ligand/VEGF-C," Oncogene 15:613-618.
Foote, J. et al. (Mar. 20, 1992). "Antibody Framework Residues Affecting the Conformation of the Hypervariable Loops," J. Mol. Biol. 224(2):487-499.
Freeman, G.J. et al. (2000). "Engagement of the PD-1 Immunoinhibitory Receptor by a Novel B7 Family Member Leads to Negative Regulation of Lymphocyte Activation," J. Exp. Med. 192(7):1027-1034.
Freeman, G.J. et al. (Nov. 5, 1993). "Uncovering of Functional Alternative CTLA-4 Counter-Receptor in B7-Deficient Mice," Science 262:907-909.
Freeman, G.J. et al. (Oct. 15, 1989). "B7, A New Member of the Ig Superfamily With Unique Expression on Activated and Neoplastic B Cells," J. Immunol. 143(8):2714-2722.
Freeman, G.J. et al. (Oct. 2, 2006, e-published on Sep. 25, 2006). "Reinvigorating Exhausted HIV-Specific T Cells Via PD-1-PD-1 Ligand Blockade," J. Exp. Med. 203(10):2223-2227.
Freeman, G.J. et al. (Sep. 1, 1991). "Structure, Expression, and T Cell Costimulatory Activity of the Murine Homologue of the Human B Lymphocyte Activation Antigen B7," J. Exp. Med. 174(3):625-631.
Fuchs, P. et al. (Dec. 1991). "Targeting Recombinant Antibodies to the Surface of *Escherichia coli*: Fusion to a Peptidoglycan Associated Lipoprotein," Biotechnology 9(12):1369-1372.
Galfre, G. et al. (Apr. 7, 1977) "Antibodies to Major Histocompatibility," Nature 266:550-552.
Garrard. L.J. et al. (Dec. 1991). "FAB Assembly and Enrichment in Monovalent Phage Display System," Bio/Technology 9:1373-1377.
Gefter, M. L. et al. (1977). "A Simple Method for Polyethylene Glycol-Promoted Hybridization of Mouse Myeloma Cells," Somatic Cell Genet. 3(2):231-236.
GenBank Accession No. AB160459.1, last updated Jul. 26, 2016, located at http://www.ncbi.nlm.nih.gov/nuccore/AB160659, last visited on Aug. 17, 2016, two pages.

(56) References Cited

OTHER PUBLICATIONS

GenBank Accession No. AB160804.1, last updated Jul. 26, 2016, located at http://www.ncbi.nlm.nih.gov/nuccore/AB160804, last visited on Aug. 17, 2016, two pages.
GenBank Accession No. AJ519552.1, last updated Jul. 24, 2016, located at http://www.ncbi.nlm.nih.gov/nuccore/AJ519552, last visited on Aug. 17, 2016, two pages.
GenBank Accession No. Z22074.1, last updated Jul. 25, 2016, located at http://www.ncbi.nlm.nih.gov/nuccore/Z22074.1, last visited on Aug. 17, 2016, two pages.
Gimmi, C.D. et al. (Aug. 1991). "B-Cell Surface Antigen B7 Provides a Costimulatory Signal That Induces T Cells to Proliferate and Secrete interleukin 2," Proc. Natl. Acad. Sci. USA 88(15):6575-6579.
Gimmi, C.D. et al. (Jul. 15, 1993). "Human T-Cell Clonal Anergy is Induced by Antigen Presentation in the Absence of B7 Costimulation," Proc. Natl. Acad. Sci. USA 90(14):6586-6590.
Gottesman, S. (1990). "Minimizing Proteolysis in *Escherichia coli*: Genetic Solutions," Methods Enzymol. 185:119-128.
Gram, H. et al. (Apr. 1992). "In vitro Selection and Affinity Maturation of Antibodies From a Naive Combinatorial Immunoglobulin Library," Proc. Natl. Acad. Sci. USA 89:3576-3580.
Griffiths, A.D. et al. (1993) "Human Anti-Self Antiboddies With High Specificity From Phage Display Libraries," EMBO J. 12(2)725-734.
Hamers-Casterman, C. et al. (Jun. 3, 1993). "Naturally Occurring Antibodies Devoid of light Chains," Nature 363:446-448.
Harding, F.A. et al. (Apr. 16, 1992) "CD28-Mediated Signalling co-Stimulates Murine T Cells and Prevents Induction of Anergy in T-cell Clones," Nature 356:607-609.
Harding, F.A. et al. (Sep. 1995). "Class Switching in Human Immunoglobulin Transgenic Mice," Ann. N. Y Acad. Sci 764:536-546.
Hawkins, R.E. et al. (1992). "Selection of Phage Antibodies by Binding Affinity Mimicking Affinity Maturation," J. Mol. Biol. 226:889-896.
Hay, B.N. et al. (Apr. 1992). "Bacteriophage Cloning and *Escherichia coli* expression of a Human IgM Fab," Hum. Antibod. Hybridomas 3:81-85.
He, L. et al. (2005). "Blockade of B7-H1 With sPD-1 Improves Immunity Against Murine Hepatocarcinoma," Anticancer Research 25:3309-3314.
Hellstrom, K.E. et al. (1987). "Antibodies For Drug Delivery", Controlled Drug Delivery, Robinson, J.R et al. eds., Marcel Dekker, Inc., New York, New York, pp. 623-653.
Hirano, F et al. (Feb. 1, 2005). "Blockade of B7-H1 and PD-1 by Monoclonal Antibodies Potentiates Cancer Therapeutic Immunity," Cancer Res. 65:1089-1096.
Hoogenboom, H. R. et al. (1991). "Multi-Subunit Proteins on the Surface of Filamentous Phage: Methodologies for Displaying Antibody (Fab) Heavy and Light Chains," Nucleic Acids Res. 19(15):4133-4137.
Huse, W. D. et al. (Decembers, 1989). "Generation of a Large Combinatorial Library of the Immunoglobulin Repertoire in Phage Lambda," Science 246:1275-1281.
Huston, J.S. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. USA 85: 5879-5883.
Hutloff, A. et al. (Jan. 21, 1999). "ICOS is an Inducible T-Cell Co-Stimulator Structurally and Functionally Yelated to CD28," Nature 397:263-266.
Hwang, W.Y.K. et al. (2005). "Use of Human Germline Genes in a CDR Homology-Based Approach to Antibody Humanization," Methods 36:35-42.
International Search Report dated Jul. 22, 2010, for PCT Patent Application No. PCT/US2009/058475, filed on Sep. 25, 2009, 1 page.

Jenkins, M.K. et al. (Feb. 1987). "Antigen Presentation by chemically Modified Splenocytes Induces Antigen-Specific T Cell Unresponsiveness In Vitro and In Vivo," J. Exp. Med. 165:302-319.
Jenkins, M.K. et al. (May 15, 1988). "Allogeneic Non-T Spleen cells restore the Responsiveness of Normal T Cell Clones Stimulated With Antigen and Chemically Modified Antigen-Presenting Cells," J. Immunol. 140(10):3324-3330.
Johnson, G. et al. (2003). "The Kabat Database and a Bioinformatics Example," Methods in Molecular Biology 248:11-25.
Jones, P.T. et al. (May 29, 1986). "Replacing the Complementarity-Determining Regions in a Human Antibody With Those From a Mouse," Nature 321:552-525.
June, C.H. et al. (1990) "Role of the CD28 Receptor in T-Cell Activation," Immunol. Today 11 (6):211-216.
Kabat, E.A. et al. (1991). "Sequences of Proteins of Immunological Interest, 5th Ed. Public Health Service," National Institutes of Health, Bethesda, MD. pp. iii-xix. (Table of Contents Only).
Kaiser, E.T. et al. (Jan. 13, 1989). "Peptide and Protein Synthesis by Segment Synthesis-Condensation," Science 243:187-192.
Kang, S-M. et al. (Aug. 21, 1992). "Transactivation by AP-1 Is A Molecular Target of T Cell Clonal Anergy," Science 257:1134-1138.
Kannanganat, S. et al. (Aug. 2007, e-pub. Jun. 6, 2007). "Multiple-Cytokine-Producing Antiviral CD4 T Cells are Functionally Superior to Single-Cytokine-Producing Cells," J. Virol. 81(16):8468-8476.
Kaufman, R.J. et al. (1987). "Translational Efficiency of Polycistronic mRNAs and Their Utilization to Express Heterologous Genes in Mammalian Cells," EMBO J. 6(1):187-193.
Keinanen, K. et al. (1994). "Biosynthetic Lipid-Tagging of Antibodies," FEBS Lett. 346:123-126.
Keir, M.E. et al. (2008, e-pub. Jan. 8, 2008). "PD-1 and Its Ligands in Tolerance and Immunity," Annu. Rev. Immunol. 26:677-704, table of contents pp. v-vi.
Kent, S.B.H. (1988). "Chemical Synthesis of Peptides and Proteins," Annu.. Rev. Biochem. 57:957-989.
Kessel, M. et al. (Jul. 27, 1990). "Murine Developmental Control Genes," Science 249:374-379.
Killion, J.J. et al. (1994). "Systemic Targeting of Liposome-Encapsulated Immunomodulators to Macrophages for Treatment of cancer Metastasis," Immunomethods 4:273-279.
Kohler, G. et al. (Aug. 7, 1975). "Continuous Cultures of Fused Cells secreting Antibodies of Predefined Specificity," Nature 256:495-497.
Koulova L. et al. (Mar. 1991). "The CD28 Ligand B7/BB1 Provides Costimulatory Signal for Alloactivation of CD4+ Cells," J. Exp. Med. 173:759-762.
Kozak, M. (Oct. 25, 1991). "Structural Features in Eukaryotic mRNAs That Modulate the Initiation of Translation," J. Biol. Chem. 266(30):19867-19870.
Kozbor, D. et al. (1983). "The Production of Monoclonal Antibodies From Human Lymphocytes," Immunol. Today 4 (3): 72-79.
Kurjan, J. et al. (Oct. 1982). "Structure of a yeast Pheromone Gene (MFa): A Putative a-Factor Precursor Contains Four Tandem Copies of Mature a-Factor," Cell 30:933-943.
Lai, L. et al. (2007, e-pub. on Aug. 14, 2007). "GM-CSF DNA: An Adjuvant for Higher Avidity IgG, Rectal IgA, and Increased Protection Against the Acute Phase of a SHIV-89.6P Challenge by a DNA/MVA Immunodeficiency Virus Vaccine," Virology 369:153-167.
Lasalle, J. M. et al. (Aug. 1, 1991). "Presentation of Autoantigen by Human T Cells," J. Immunol. 147(3):774-780.
Latchman, Y. et al. (Mar. 2001). "PD-L2 is a Second Ligand for PD-1 and Inhibits T Cell Activation," Nat. Immunol. 2(3):261-268.
Lenschow, D.J. et al. (1992). "Long-Term Survival of Xenogeneic Pancreatic Islet Grafts Induced by CTLA4Ig," Science 257:789-792.
Lenscow, D.J. et al. (Aug. 7, 1996). "CD28/B7 System of T Cell Costimulation," Annu. Rev. Immunol. 14:233-258.
Lerner, E.A. (1981). "How to Make a Hybridoma," Yale J. Biol. Med. 54:387-402.
Ling, V. et al. (2000). "Cutting Edge: Identification of GL50, A Novel B7-Like Protein that Functionally Binds to ICOS Receptor," J. Immunol. 164:1653-7.

(56) References Cited

OTHER PUBLICATIONS

Linsley, P.S. et al. (Mar. 1991). "Binding of the B Cell Activation Antigen B7 to CD28 Costimulates T Cell Proliferation and Interleukin 2 mRNA Accumulation," J. Exp. Med. 173:721-730.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.
Liu, Y et al. (Feb. 1992). "Heat-Stable Antigen Is a Costimulatory Molecule for CD4 T Cell Growth," J. Exp. Med. 175:437-445.
Lonberg, N. et al. (1994). "Transgenic Approaches to Human Monoclonal Antibodies," Chapters in Handbook of Experimental Pharmacology, M. Rosenberg, eds. et al., Springer-Verlag, Berlin, Germany, 113:49-101.
Lonberg, N. et al. (1995). "Human Antibodies From Transgenic Mice," Intern. Rev. Immunol. 13:65-93.
Lonberg, N. et al. (Apr. 28, 1994). "Antigen-Specific Human Antibodies From Mice Comprising Four Distinct Genetic Modifications," Nature 368:856-859.
Lucklow, V.A. et al. (1989). "High Level Expression of Nonfused Foreign Genes with Autographa californica Nuclear Polyhedrosis Virus Expression Vectors," Virology 170:31-39.
MacCallum, R.M. et al. (Oct. 11, 1996). "Antibody-Antigen Interactions: Contact Analysis and Binding Site Topography," J. Mol. Biol. 262(5):732-745.
Mages, H.W. et al. (2000). "Molecular Cloning and characterization of Murine ICOs and Identification of B7has ICOS Ligand," Eur. J. Immunol. 30:1040-1047.
Marasco, W. A. et al. (Aug. 1993). "Design, Intracellular Expression, and Activity of a Human Anti-Human Immunodeficiency virus Type 1 gp120 Single-Chain Antibody," Proc. Natl. Acad. Sci. USA 90:7889-7893.
McCafferty, J. et al. (Dec. 1990). "Phage Antibodies: Filamentous Phage Displaying Antibody variable Domains," Nature 348:552-554.
McConnell, H.M. et al. (Sep. 25, 1992). "The Cytosensor Microphysiometer: Biological Applications of Silicon Technology," Science 257:1906-1912.
Merrifield, B. (Apr. 18, 1986). "Solid Phase Synthesis," Science 232:341-342-347..
Merrifield, J. (Jan. 15, 1969). "The Total Synthesis of an Enzyme with Ribonuclease A Activity," J Am Chem. Soc. 91(2):501-502.
Meyers, E.W. et al. (1989). "Optimal Alignment in Linear Space," Cabios 4(1): 11-17.
Mhashilkar, A. M. et al. (1995). "Inhibitions of HIV-1 Tat-Mediated LTR Transactivation and HIV-1 Infection by AntiTat Single Chain Intrabodies," EMBO J. 14(7): 1542-1551.
Mills, F.C. et al. (1990). "Sequences of Human Immunoglobulin Switch Regions: Implications for Recombination and Transcription," Nucl. Acids Res. 18(24):7305-7316.
Morrison, S.L. (Sep. 20, 1985). "Tranfectomas Provide Novel Chimeric Antibodies," Science 229:1202-1207.
Mueller, D.L. et al. (May 15, 1990). "An Intracellular Calcium Increase and Protein Kinase C Activation Fail to Initiate T Cell Proliferation in the Absence of a Costimulatory Signal," J. Immunol. 144(10):3701-3709.
Needleman, S. B. et al. (1970). "A General Method Applicable to the Search for Similarities in the Amino Acid sequence of Two Proteins," J. Mol. Biol. 48:444-453.
Nishimura, H. et al. (Aug. 1999). "Development of Lupus-Like Autoimmune Diseases by Disruption of the PD-1 Gene Encoding an ITIM Motif-Carrying Immunoreceptor," Immunity 11(2):141 -151.
Nishimura, H. et al. (Jan. 12, 2001). "Autoimmune Dilated Cardiomyopathy in PD-1 Receptor-Deficient Mice," Science 291:319-322.
Nishimura, H. et al. (May 1996). "Developmentally Regulated Expression of the PD-1 Protein on the Surface of Double-Negative (CD4-CD8-) Thymocytes," Int. Immunol. 8(5):773-780.

Nishimura, Y. et al. (Feb. 15, 1987). "Recombinant Human-Mouse Chimeric Monoclonal Antibody Specific for Common Acute Lymphocytic Leukemia Antigen," Cancer Res 47(4):999-1005.
Nomi, T. et al. (Apr. 1, 2007). "Clinical Significance and Therapeutic Potential of the Programed Death-1 Ligand/Programmed Death-1 Pathway in Human Pancreatic Cancer," Clinical Cancer Research, the American Association for Cancer Research 13(7):2151-2157.
Néeraudeau, D. et al. (Jan. 1, 2000). "Upper Cretaceous Echinoids From James Ross Basin, Antarctica," GEOBIOS, Editions Scientifiques et Medicales Elseveir 33(4):455-466.
Oi, V.T. et al. (May/Jun. 1986). "Chimeric Antibodies," Biotechniques 4(3):214-219, Overview pp. 112-113.
Order, S.E. (1985). "Analysis, Results, and Future Prospective of the Therapeutic Use of Radiolabeled Antibody in Cancer Therapy,", Chapter 15 in Monoclonal Antibodies For Cancer Detection and Therapy, Baldwin, R.W. et al. eds., Academic Press, Inc., Orlando, Florida, pp. 303-316.
Owais, M. et al. (Jan. 1995) "Chloroquine Encapsulated in Malaria-Infected Erythrocyte-Specific Antibody-Bearing Liposomes Effectively Controls Chloroquine-Resistant Plasmodium Berghei Infections in Mice," Antimicrob. Agents Chemother. 39(1):180-184.
Panka, D.J. et al. (May 1988). "Variable Region Framework Differences Result in Decreased or Increased Affinity of Variant Anti-Digoxin Antibodies," Proc. Natl. Acad. Sci. USA 85(9):3080-3084.
Perez, P. et al. (Jul. 25, 1985). "Specific Targeting of Cytotoxic T Cells by Anti-T3 Linked to Anti-Target Cell Antibody," Nature 316:354-356.
Pinkert, C.A. et al. (May 1987). "An Albumin Enhancer Located 10 kb Upstream Functions Along With its Promoter to Direct Efficient, Liver-Specific Expression in Transgenic Mice," Genes Dev. 1(3):268-276.
Queen, C. et al. (Dec. 1989). "A Humanized Antibody That Binds to the Interleukin 2 Receptor," Proc. Natl. Acad. See. U.S.A. 86:10029-10033.
Queen, C.et al. (Jul. 1983) "Immunoglobulin Gene Transcription is Activated by Downstream Sequence Elements," Cell 33:741-748.
Radhakrishnan, S. et al. (2003). "Naturally Occurring Human IgM Antibody That Binds B7-DC and Potentiates T cell Stimulation by Dendritic Cells," J. Immunol. 170:1830-1838. Retracted on Jun. 1, 2010.
Ranade, V. (Aug. 1989) "Drug Delivery Systems. 1. Site-Specific Drug Using Liposames as Carriers," J. Clin. Pharmacol. 29:685-694.
Ravetch, J.V. et al. (1991). "Fc Receptors," Annu. Rev. Immunol. 9:457-492.
Reiser, H. et al. (Jan. 1, 1992). "Murine B7 Antigen Provides an Efficient Costimulatory Signal for Activation of Murine T Lymphocytes Via the T-Cell receptor/CD3 Complex," Proc. Natl. Acad. Sci. USA 89:271-275.
Richardson, J. H. et al. (Apr. 11, 1995). "Phenotypic Knockout of the High-Affinity Human Interleukin 2 Receptor by Intracellular Single-Chain Antibodies Against the α Subunit of the Receptor," Proc. Natl. Acad. Sci. USA 92 (8):3137-3141.
Riechmann, L. et al. (Mar. 24, 1988). "Reshaping Human Antibodies for Therapy," Nature 332:323-327.
Riley, J. L. et al. (Apr. 15, 2001). "ICOS Costimulation Requires IL-2 and Can be Prevented by CTLA-4 Engagement," J. Immunol. 166(8):4943-4948.
Robinson, J.R. (1978). Sustained and Controlled Release Drug Delivery Systems, Marcel Dekker, Inc., New York, New York, pp. v-vii. (Table of Contents Only.).
Rudikoff, S. et al. (Mar. 1982). "Single Amino Acid Substitution Altering Antigen-Binding Specificity," Proc. Natl. Acad. Sci. USA 79(6):1979-1983.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 29 pages, (Table of Contents only).

(56) References Cited

OTHER PUBLICATIONS

Schreier, H. et al. (Mar. 25, 1994) "Targeting of Liposomes to Cells Expressing CD4 Using Glycosylphosphatidylinositol-Anchored gp120. Influence of Liposome Composition on Intracellular Trafficking," J. Biol. Chem. 269(12):9090-9098.
Schultz, L.D. et al. (1987) "Expression and Secretion in Yeast of a 400-kDa Envelope Glycoprotein Derived From Epstein-Barr Virus," Gene 54:113-123.
Schwartz, R.S. (1993). "Autoimmunity and Autoimmune Diseases," Chapter 30 in Fundamental Immunology, Paul, W.E. ed., Raven Press, New York, New York, pp. 1033-1097.
Seed, B. (Oct. 29, 1987) "An LFA-3 cDNA Encodes a Phospholipid-Linked Membrane Protein Homologous to its Receptor CD2," Nature 329:840-842.
Sequence Data OM Protein Search run on Aug. 13, 2014, 1 QHSWEIPYT 9, 1 page.
Sharpe, A.H. et al. (2007). "The Function of Programmed Cell Death 1 and its Ligands in Regulating Autoimmunity and Infection," Nat. Immunol. 8:239-245.
Shaw, D.R. et al. (Dec. 7, 1988). "Mouse/Human Chimeric Antibodies to a Tumor-Associated Antigen: Biologic Activity of the Four Human IgG Subclasses," Natl Cancer Inst. 80(19):1553-1559.
Sheriff, S. et al. (Sep. 1996). "Redefining the Minimal Antigen-Binding Fragment," Nature Struct. Biol. 3(9): 733-736.
Shin, T. et al. (May 16, 2005). "In Vivo Costimulatory Role of B7-DC in Tuning T Helper cell 1 and Cytotoxic T Lymphocyte Responses," J. Exp Med. 201(10):1531-1541.
Sideras, P. et al. (1989). "Production of Sterile transcripts of Cy Genes in an IgM-Producing Human Neoplastic B Cell Line That Switches to IgG-Producing Cells," International Immunology 1(6):631-642.
Sjolander, S. et al. (Oct. 15, 1991). "Integrated Fluid Handling System for Biomolecular Interaction Analysis," Anal. Chem. 63(20):2338-2345.
Smith, D.B. et al. (1988). "Single-Step Purification of Polypeptides Expressed in *Escherichia coli* as Fusions With Glutathione S-Transferase," Gene 67:31-40.
Smith, G.E. et al. (Dec. 1983). "Production of Human Beta Interferon in Insect Cells Infected With a Baculovirus Expression Vector," Mol. Cell Biol. 3(12):2156-2165.
Staerz, U.D. et al. (1986). "Use of Anti-Receptor Antibodies to Focus T-Cell Activity," Immunol. Today 7(7 & 8):241-245.
Staerz, U.D. et al. (Apr. 18, 1985). "Hybrid Antibodies Can Target Sites for Attack by T Cells," Nature 314:628-631.
Staerz, U.D. et al. (Mar. 1986). "Hybrid Hybridoma Producing a Bispecific Monoclonal Antibody That Can Focus Effector T-cell Activity," Proc. Natl. Acad. Sci. USA 83:1453-1457.
Strejan, G.H. et al. (Nov. 1984). "Suppression of Chronic-Relapsing Experimental Allergic Encephalomyelitis in Strain-13 Guinea Pigs by Administration of Liposome-Associated Myelin Basic Protein," J. Neuroimmunol. 7 (1):27-41.
Studier, F.W. et al. (1990). "Use of T7 RNA Polymerase to Direct Expression of Cloned Genes," Methods Enzymol. 185:60-89.
Subudhi, S.K. et al. (Mar. 2004). "Local Expression of B7-H1 Promotes Organ-Specific Autoimmunity and Transplant Rejection," J. Clin Invest. 113(5):694-700.
Sun, L.K. et al. (Jan. 1987). "Chimeric Antibody With Human Constant Regions and Mouse Variable Regions Directed Against Carcinoma-Associated Antigen 17-1 A," Proc. Natl. Acad. Sci. 84(1):214-218.
Szabo, A. et al. (Oct. 1995). "Surface Plasmon Resonance and its use in Biomolecular Interaction analysis (BIA)," Curr. Opin. Struct. Biol. 5(5):699-705.
Tamura, H. et al. (Mar. 15, 2001). "B7-H1 Costimulation Preferentially Enhances CD28-lndependent T-Helper Cell Function," Blood 97(6):1809-1816.
Tamura, M. et al. (Feb. 2000). "Structural Correlates of an Anticarcinoma Antibody: Identification of Specificity-Determining Residues (SDRs) and Development of a Minimally Immunogenic Antibody Variant by Retention of SDRs Only," J. Immunol. 164(3): 1432-1441.

Taylor, L. et al. (Apr. 1994). "Human Immunoglobulin Transgenes Undergo Rearrangement, Somatic Mutation and Class Switching in Mice That Lack Endogenous IgM," International Immunology 6(4):579 591.
Taylor, L.D. et al. (Dec. 11, 1992). "A Transgenic Mouse That Expresses a Diversity of Human Sequence Heavy and Light Chain Immunoglobulins," Nucleic Acids Research 20(23):6287 6295.
Thorpe, P.E. (1985). "Antibody Carriers of Cytotoxic Agents In Cancer Therapy: A Review", in Monoclonal Antibodies '84: Biological and Clinical Applications, Pinchera et al. (eds.), pp. 475-506.
Thorpe, P.E. et al. (1982). "The Preparation and Cytotoxic Properties of Antibody-Toxin Conjugates," Immunol. Rev. 62:119-158.
Townsend, S.E. et al. (Jan. 15, 1993). "Tumor Rejection After Direct Costimulation of CD8+ T Cells by B7-Transfected Melanoma Cells," Science 259:368-370.
Tuaillon, N. et al. (Apr. 15, 1993). "Human Immunoglobulin Heavy-Chain Minilocus Recombination in Transgenic Mice: Gene-Segment Use in µ and γ Transcripts," Proc. Natl. Acad. Sci USA 90(8):3720 3724.
Tuaillon, N. et al. (Mar. 15, 1994). "Biased Utilization of DHQ52 and JH4 Gene Segments in a Human Ig Transgenic Minilocus is Independent of Antigenic Selection," J. Immunol. 152(6):2912-2920.
Turka, L.A. et al. (Nov. 15, 1992). "T-cell Activation by the CD28 Ligand B7 is Required for Cardiac Allograft Rejection in vivo," Proc. Natl. Acad. Sci. USA 89(22):11102-11105.
Umezawa, F. et al. (Jun. 30, 1988). "Liposome Targeting to Mouse Brain: Mannose as a Recognition Marker," Biochem. Biophys. Res. Commun. 153(3):1038-1044.
Van-Seventer, G.A. et al. (Jun. 15, 1990). "The LFA-1 Ligand ICAM-1 Provides an Important Costimulatory Signal for T Cell Receptor-Mediated Activation of Resting T Cells," J. Immunol. 144(12):4579-4586.
Velu, V. et al. (Jun. 2007). "Elevated Expression Levels of Inhibitory Receptor Programmed Death 1 on Simian Immunodeficiency Virus-Specific CD8 T Cells During Chronic Infection But Not After Vaccination," Journal of Virology 81 (11):5819-5828.
Velu, V. et al. (Mar. 12, 2009). "Enhancing SIV-Specific Immunity in vivo by PD-1 Blockade," Nature 458:206-209.
Verhoeyan, M. et al. (Mar. 25, 1988). "Reshaping Human Antibodies: Grafting an Antilysozyme Activity," Science 239:1534-1536.
Wada, K-N. et al. (May 11, 1992). "Codon Usage Tabulated From the GenBank Genetic Sequence Data," Nucleic Acids Res. 20:2111-2118.
Ward, E.S. et al. (Oct. 12, 1989). "Binding Activities of a Repertoire of Single Immunoglobulin Variable Domains Secreted From *Escherichia coli*," Nature 341:544-546.
Waterhouse, P. et al. (Nov. 10, 1995). "Lymphoproliferative Disorders With Early Lethality in Mice Deficient in Ctla-4," Science 270:985-988.
Werge, T.M. et al. (Nov. 12, 1990). "Intracellular Immunization. Cloning and Intracellular Expression of a Monoclonal Antibody to the p21ras Protein," FEBS Lett. 274(1-2):193-198.
Winoto, A. et al. (Mar. 1989). "A Novel, Inducible and T cell-Specific Enhancer Located at the 3' End of the T Cell Receptor a Locus," EMBO J. 8(3):729-733.
Wood, C.R. et al. (Apr. 4, 1985). "The Synthesis and in vivo Assembly of Functional Antibodies in Yeast," Nature 314:446-449.
Written Opinion of the International Searching Authority dated Jul. 22, 2010, for PCT Patent Application No. PCT/US2009/058475, filed on Sep. 25, 2009, 7 pages.
Xu, J.L. et al. (Jul. 2000). "Diversity in the CDR3 Region of VH is Sufficient for Most Antibody Specificities," Immunity 13(1):37-45.
Yamazaki, T. et al. (2002). "Expression of Programmed death 1 Ligands by Murine T cells and APC," J. Immunol. 169(10)5538-5545.
Yeh, E.T.H. et al. (Oct. 1986). "Expression of T-cell-Activating Protein in Peripheral Lymphocyte Subsets," Proc. Natl. Acad. Sci. 83(19)7424-7428.
Yeh, M.Y. et al. (Mar. 15, 1982). "A Cell-Surface Antigen Which is Present in the Ganglioside Fraction and Shared by Human Melanomas," Int. J. Cancer 29(3):269-275.

(56) References Cited

OTHER PUBLICATIONS

Yoshinaga, S.K. et al. (Dec. 16, 1999). "T-Cell Co-Stimulation Through B7RP-1 and ICOS," Nature 402:827-832.

Young, J.W. et al. (Jul. 1992). "The B7/BB1 Antigen Provides One of Several Costimulatory Signals for the Activation of CD4+ T Lymphocytes by Human Blood Dendritic Cells in Vitro," J. Clin. Invest. 90(1):229-237.

Zhong, X. et al. (Sep. 2007). "PD-L2 Expression Extends Beyond Dendritic Cells/Macrophages to B1 Cells Enriched for VH11/VH12 and Phosphatidylcholine Binding," Eur. J. Immunol. 37(9):2405-2410.

FIG. 1 Expression Vector Diagrams
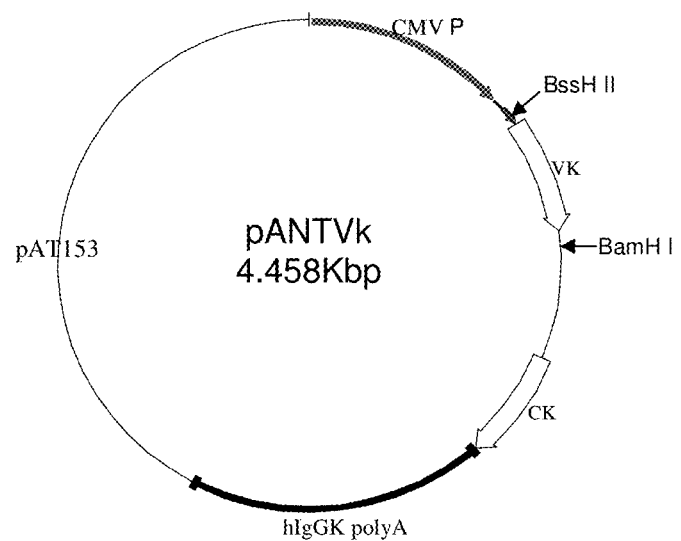
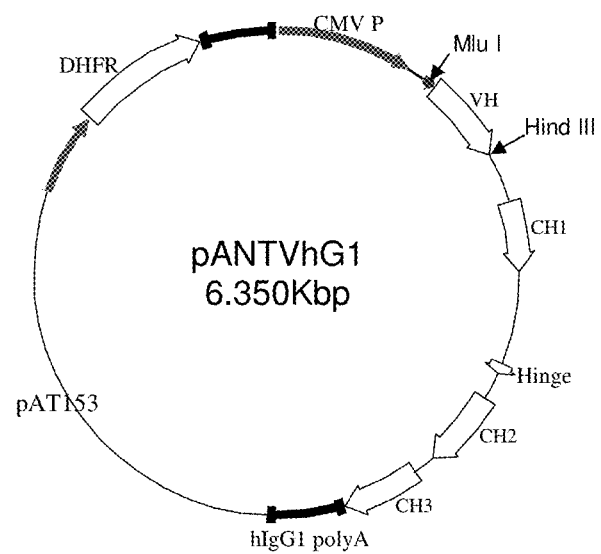

FIGS. 2A-2E: Composite, Human Antibody Sequence Variants of Anti-PD-1 Heavy Chains

FIG. 2A Heavy chain VH1

```
        10        20        30        40        50
CAGGTCCAGCTTGTGCAGTCTGGGGCTGAACTGAAACAGCCTGGGGCCTC
 Q   V   Q   L   V   Q   S   G   A   E   L   K   Q   P   G   A   S 60        70        80        90       100
AGTGAAGATGTCCTGCAAGGCTTCTGGCTACAGTTTTACTAGCTCCTGGA
  V   K   M   S   C   K   A   S   G   Y   S   F   T   S   S   W
                                                   ─────────────
                                                        CDR1

110       120       130       140       150
TACACTGGGTGAAACAGGCTCCTGGACAGGGTCTGGAATGGATTGGATAC
 I   H   W   V   K   Q   A   P   G   Q   G   L   E   W   I   G   Y
─────                                                           ──

160       170       180       190       200
ATTTATCCTAGCACTGGTTTTACTGAGTACAATCAGAAGTTCAAGGACAG
  I   Y   P   S   T   G   F   T   E   Y   N   Q   K   F   K   D   R
 ─────────────────────────────────────────────────────────────────
                       CDR2

210       220       230       240       250
GGCCACATTGACTGCAGACAAATCCACCAGCACAGCCTACATGGAACTGA
   A   T   L   T   A   D   K   S   T   S   T   A   Y   M   E   L 260       270       280       290       300
GCAGCCTGAGATCTGAGGACTCTGCAGTCTATTACTGTGCAAGATGGAGG
  S   S   L   R   S   E   D   S   A   V   Y   Y   C   A   R   W   R
                                                           ─────────

310       320       330       340       350
GACAGCTCGGGCTACCATGCTATGGACTACTGGGGTCAAGGAACCTCAGT
   D   S   S   G   Y   H   A   M   D   Y   W   G   Q   G   T   S   V
 ───────────────────────────────────────────
            CDR3

360
CACCGTCTCCTCA (SEQ ID NO:1)
  T   V   S   S   (SEQ ID NO:25)
```

FIG. 2B Heavy chain VH2

```
          10         20         30         40         50
CAGGTCCAGCTTGTGCAGTCTGGGGCTGAAGTGAAACAGCCTGGGGCCTC
  Q  V  Q  L  V  Q  S  G  A  E  V  K  Q  P  G  A  S 60         70         80         90        100
AGTGAAGATGTCCTGCAAGGCTTCTGGCTACAGTTTTACTAGCTCCTGGA
   V  K  M  S  C  K  A  S  G  Y  S  F  T  S  S  W
                                            ―――――――
                                              CDR1

110        120        130        140        150
TACACTGGGTGAAACAGGCTCCTGGACAGGGTCTGGAATGGATTGGATAC
  I  H  W  V  K  Q  A  P  G  Q  G  L  E  W  I  G  Y
  ―――                                              ―

160        170        180        190        200
ATTTATCCTAGCACTGGTTTTACTGAGTACAATCAGAAGTTCAAGGACAG
   I  Y  P  S  T  G  F  T  E  Y  N  Q  K  F  K  D  R
   ――――――――――――――――――――――――――――――――――――――――――――――――
                        CDR2

210        220        230        240        250
GGCCACATTGACTGCAGACAAATCCACCAGCACAGCCTACATGGAACTGA
   A  T  L  T  A  D  K  S  T  S  T  A  Y  M  E  L 260        270        280        290        300
GCAGCCTGAGATCTGAGGACACTGCAGTCTATTACTGTGCAAGATGGAGG
  S  S  L  R  S  E  D  T  A  V  Y  Y  C  A  R  W  R
                                               ――――

310        320        330        340        350
GACAGCTCGGGCTACCATGCTATGGACTACTGGGGTCAAGGAACCTCAGT
   D  S  S  G  Y  H  A  M  D  Y  W  G  Q  G  T  S  V
   ―――――――――――――――――――――――――
            CDR3

360
CACCGTCTCCTCA (SEQ ID NO:3)
   T  V  S  S  (SEQ ID NO:26)
```

FIG. 2C Heavy chain VH3

```
          10        20        30        40        50
CAGGTCCAGCTTGTGCAGTCTGGGGCTGAAGTGAAACAGCCTGGGGCCTC
  Q  V  Q  L  V  Q  S  G  H  E  V  K  Q  P  G  A  S 60        70        80        90       100
AGTGAAGATGTCCTGCAAGGCTTCTGGCTACAGTTTTACTAGCTCCTGGA
   V  K  M  S  C  K  A  S  G  Y  S  F  T  S  S  W
                                          ─────────
                                             CDR1

110       120       130       140       150
TACACTGGGTGAAACAGGCTCCTGGACAGGGTCTGGAATGGATTGGATAC
   I  H  W  V  K  Q  A  P  G  Q  G  L  E  W  I  G  Y
   ───                                             ─

160       170       180       190       200
ATTTATCCTAGCACTGGTTTTACTGAGTACAATCAGAAGTTCAAGGACAG
   I  Y  P  S  T  G  F  T  E  Y  N  Q  K  F  K  D  R
   ──────────────────────────────────────────────
                        CDR2

210       220       230       240       250
GGCCACATTGACTGCAGACAAATCCACCAGCACAGCCTACATGGAACTGA
   A  T  L  T  A  D  K  S  T  S  T  A  Y  M  E  L 260       270       280       290       300
GCAGCCTGAGATCTGAGGACACTGCAGTCTATTACTGTGCAAGATGGAGG
   S  S  L  R  S  E  D  T  A  V  Y  Y  C  A  R  W  R
                                                ─────

310       320       330       340       350
GACAGCTCGGGCTACCATGCTATGGACTACTGGGGTCAAGGAACCCTGGT
   D  S  S  G  Y  H  A  M  D  Y  W  G  Q  G  T  L  V
   ──────────────────────────────
              CDR3

360
CACCGTCTCCTCA  (SEQ ID NO:5)
   T  V  S  S  (SEQ ID NO:27)
```

FIG. 2D Heavy chain VH4

```
          10         20         30         40         50
CAGGTCCAGCTTGTGCAGTCTGGGCATGAAGTGAAACAGCCTGGGGCCTC
  Q  V  Q  L  V  Q  S  G  H  E  V  K  Q  P  G  A  S 60         70         80         90        100
AGTGAAGATGTCCTGCAAGGCTTCTGGCTACAGTTTTACTAGCTCCTGGA
   V  K  M  S  C  K  A  S  G  Y  S  F  T  S  S  W
                                            ─────────
                                              CDR1
         110        120        130        140        150
TACACTGGGTGAGACAGGCTCCTGGACAGGGTCTGGAATGGATTGGATAC
  I  H  W  V  R  Q  A  P  G  Q  G  L  E  W  I  G  Y
  ────                                           ───

160        170        180        190        200
ATTTATCCTAGCACTGGTTTTACTGAGTACAATCAGAAGTTCAAGGACAG
  I  Y  P  S  T  G  F  T  E  Y  N  Q  K  F  K  D  R
  ──────────────────────────────────────────────
                        CDR2

210        220        230        240        250
GGCCACATTGACTGCAGACAAATCCACCAGCACAGCCTACATGGAACTGA
   A  T  L  T  A  D  K  S  T  S  T  A  Y  M  E  L 260        270        280        290        300
GCAGCCTGAGATCTGAGGACACTGCAGTCTATTACTGTGCAAGATGGAGG
  S  S  L  R  S  E  D  T  A  V  Y  Y  C  A  R  W  R
                                              ──────

310        320        330        340        350
GACAGCTCGGGCTACCATGCTATGGACTACTGGGGTCAAGGAACCCTGGT
  D  S  S  G  Y  H  A  M  D  Y  W  G  Q  G  T  L  V
  ──────────────────────────────
           CDR3

360
CACCGTCTCCTCA (SEQ ID NO:52)
  T  V  S  S  (SEQ ID NO:28)
```

FIG. 2E Heavy chain VH5

```
         10        20        30        40        50
CAGGTCCAGCTTGTGCAGTCTGGGCATGAAGTGAAACAGCCTGGGGCCTC
 Q   V   Q   L   V   Q   S   G   H   E   V   K   Q   P   G   A   S 60        70        80        90       100
AGTGAAGGTGTCCTGCAAGGCTTCTGGCTACAGTTTTACTAGCTCCTGGA
 V   K   V   S   C   K   A   S   G   Y   S   F   T   S   S   W
                                                  ‾‾‾‾‾‾‾‾‾
                                                     CDR1

110       120       130       140       150
TACACTGGGTGAGACAGGCTCCTGGACAGGGTCTGGAATGGATTGGATAC
 I   H   W   V   R   Q   A   P   G   Q   G   L   E   W   I   G   Y
‾‾‾‾‾                                                           ‾‾‾

160       170       180       190       200
ATTTATCCTAGCACTGGTTTTACTGAGTACAATCAGAAGTTCAAGGACAG
 I   Y   P   S   T   G   F   T   E   Y   N   Q   K   F   K   D   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                       CDR2

210       220       230       240       250
GGCCACAATCACTGCAGACAAATCCACCAGCACAGCCTACATGGAACTGA
 A   T   I   T   A   D   K   S   T   S   T   A   Y   M   E   L 260       270       280       290       300
GCAGCCTGAGATCTGAGGACACTGCAGTCTATTACTGTGCAAGATGGAGG
 S   S   L   R   S   E   D   T   A   V   Y   Y   C   A   R   W   R
                                                         ‾‾‾‾‾‾‾‾‾

310       320       330       340       350
GACAGCTCGGGCTACCATGCTATGGACTACTGGGGTCAAGGAACCCTGGT
 D   S   S   G   Y   H   A   M   D   Y   W   G   Q   G   T   L   V
‾‾‾‾‾‾‾‾‾‾‾‾‾‾‾‾‾‾‾‾‾‾‾‾‾‾‾‾‾‾
         CDR3

360
CACCGTCTCCTCA (SEQ ID NO:53)
 T   V   S   S  (SEQ ID NO:29)
```

FIGS. 3A-3D: Composite, Human Antibody Sequence Variants of Anti-PD-1 Light Chains

FIG. 3A Light chain VK1

```
         10        20        30        40        50
GACATTGTGCTGACACAGTCTCCTGCTTCCTTAACTCTGTCTCCAGGGCA
  D  I  V  L  T  Q  S  P  A  S  L  T  L  S  P  G  Q 60        70        80        90       100
GAGGCTCACCATCTCATGCAGGGCCAGCCAAAGTGTCAGTACATCTGGCT
   R  L  T  I  S  C  R  A  S  Q  S  V  S  T  S  G
                     ─────────────────────────────
                                  CDR1

110       120       130       140       150
ATAGTTATATGCACTGGTACCAACAGAAACCAGACCAGTCCCCCAAACTC
 Y  S  Y  M  H  W  Y  Q  Q  K  P  D  Q  S  P  K  L
 ─────────────

160       170       180       190       200
CTCATCAAGTTTGGCTCCAACCTAGAATCTGGCATCCCTGCCAGGTTCAG
   L  I  K  F  G  S  N  L  E  S  G  I  P  A  R  F  S
         ──────────────────────
                 CDR2

210       220       230       240       250
TGGCAGTGGGTCTGGGACAGACTTCACCCTCACCATCTCTTCTCTGGAGG
   G  S  G  S  G  T  D  F  T  L  T  I  S  S  L  E 260       270       280       290       300
AGGAGGATTTTGCAACATATTACTGTCAGCACAGTTGGGAGATTCCGTAC
   E  E  D  F  A  T  Y  Y  C  Q  H  S  W  E  I  P  Y
                           ─────────────────────────
                                      CDR3

310       320       330
ACGTTCGGACAGGGGACCAAGCTGGAAATAAAA (SEQ ID NO:54)
   T  F  G  Q  G  T  K  L  E  I  K  (SEQ ID NO:30)
   ─
```

FIG. 3B Light chain VK2

```
         10        20        30        40        50
GACATTGTGCTGACACAGTCTCCTGCTACCTTATCTCTGTCTCCAGGGCA
 D  I  V  L  T  Q  S  P  A  T  L  S  L  S  P  G  Q 60        70        80        90       100
GAGGCTCACCATCTCATGCAGGGCCAGCCAAAGTGTCAGTACATCTGGCT
 R  L  T  I  S  C  R  A  S  Q  S  V  S  T  S  G
                   ─────────────────────────────────
                                CDR1

110       120       130       140       150
ATAGTTATATGCACTGGTACCAACAGAAACCAGACCAGTCCCCCAAACTC
 Y  S  Y  M  H  W  Y  Q  Q  K  P  D  Q  S  P  K  L
 ────────────────

160       170       180       190       200
CTCATCAAGTTTGGCTCCAACCTAGAATCTGGCATCCCTGCCAGGTTCAG
 L  I  K  F  G  S  N  L  E  S  G  I  P  A  R  F  S
          ───────────────────────
                   CDR2

210       220       230       240       250
TGGCAGTGGGTCTGGGACAGACTTCACCCTCACCATCTCTTCTCTGGAGC
 G  S  G  S  G  T  D  F  T  L  T  I  S  S  L  E 260       270       280       290       300
CTGAGGATTTTGCAACATATTACTGTCAGCACAGTTGGGAGATTCCGTAC
 P  E  D  F  A  T  Y  Y  C  Q  H  S  W  E  I  P  Y
                            ──────────────────────────
                                       CDR3

310       320       330
ACGTTCGGACAGGGGACCAAGCTGGAAATAAAA (SEQ ID NO:55)
 T  F  G  Q  G  T  K  L  E  I  K  (SEQ ID NO:31)
 ─
```

FIG. 3C Light chain VK3

```
         10        20        30        40        50
GAGATTGTGCTGACACAGTCTCCTGCTACCTTATCTCTGTCTCCAGGGCA
  E  I  V  L  T  Q  S  P  A  T  L  S  L  S  P  G  Q 60        70        80        90       100
GAGGCTCACCATCTCATGCAGGGCCAGCCAAAGTGTCAGTACATCTGGCT
  R  L  T  I  S  C  R  A  S  Q  S  V  S  T  S  G
                    ────────────────────────────────
                                             CDR1

110       120       130       140       150
ATAGTTATATGCACTGGTACCAACAGAAACCAGACCAGTCCCCCAAACTC
  Y  S  Y  M  H  W  Y  Q  Q  K  P  D  Q  S  P  K  L
  ───────────────

160       170       180       190       200
CTCATCAAGTTTGGCTCCAACCTAGAATCTGGCATCCCTGCCAGGTTCAG
  L  I  K  F  G  S  N  L  E  S  G  I  P  A  R  F  S
           ────────────────────────
                CDR2

210       220       230       240       250
TGGCAGTGGGTCTGGGACAGACTTCACCCTCACCATCTCTTCTCTGGAGC
  G  S  G  S  G  T  D  F  T  L  T  I  S  S  L  E 260       270       280       290       300
CTGAGGATTTTGCAACATATTACTGTCAGCACAGTTGGGAGATTCCGTAC
  P  E  D  F  A  T  Y  Y  C  Q  H  S  W  E  I  P  Y
                           ─────────────────────────
                                             CDR3

310       320       330
ACGTTCGGACAGGGGACCAAGCTGGAAATAAAA (SEQ ID NO:56)
  T  F  G  Q  G  T  K  L  E  I  K   (SEQ ID NO:32)
  ─
```

FIG. 3D Light chain VK4

```
          10        20        30        40        50
GACATTGTGCTGACACAGTCTCCTGCTACCTTATCTCTGTCTCCAGGGCA
 D  I  V  L  T  Q  S  P  A  T  L  S  L  S  P  G  Q 60        70        80        90       100
GAGGCTCACCATCTCATGCAGGGCCAGCCAAAGTGTCAGTACATCTGGCT
 R  L  T  I  S  C  R  A  S  Q  S  V  S  T  S  G
                      ─────────────────────────────
                                              CDR1

110       120       130       140       150
ATAGTTATATGCACTGGTACCAACAGAAACCAGACCAGTCCCCCAAACTC
 Y  S  Y  M  H  W  Y  Q  Q  K  P  D  Q  S  P  K  L
 ───────────────

160       170       180       190       200
CTCATCAAGTTTGGCTCCAACCTAGAATCTGGCATCCCTGCCAGGTTCAG
 L  I  K  F  G  S  N  L  E  S  G  I  P  A  R  F  S
          ──────────────────
                CDR2

210       220       230       240       250
TGGCAGTGGGTCTGGGACAGACTTCACCCTCACCATCTCTTCTCTGGAGC
 G  S  G  S  G  T  D  F  T  L  T  I  S  S  L  E 260       270       280       290       300
CTGAGGATTTTGCAGTGTATTACTGTCAGCACAGTTGGGAGATTCCGTAC
 P  E  D  F  A  V  Y  Y  C  Q  H  S  W  E  I  P  Y
                            ─────────────────────────
                                              CDR3

310       320       330
ACGTTCGGACAGGGGACCAAGCTGGAAATAAAA (SEQ ID NO:57)
 T  F  G  Q  G  T  K  L  E  I  K  (SEQ ID NO:33)
 ─
```

FIGS. 4A-4E: Composite, Human Antibody Sequence Variants of Anti-PD-L1 Heavy Chains

FIG. 4A Heavy chain VH1

```
            10         20         30         40         50
GAGGTCCAGCTGGTGCAGTCTGGACCTGAGCTGAAAAAGCCTGGGGCTTC
 E   V   Q   L   V   Q   S   G   P   E   L   K   K   P   G   A   S 60         70         80         90        100
AGTGAAGATGTCCTGCAAGGCTTCTGGATACACATTCACTAGCTATGTTA
 V   K   M   S   C   K   A   S   G   Y   T   F   T   S   Y   V
                                                   ─────────────
                                                        CDR1

110        120        130        140        150
TGCACTGGGTGAAGCAGGCCCCTGGGCAGCGCCTTGAGTGGATTGGATAT
 M   H   W   V   K   Q   A   P   G   Q   R   L   E   W   I   G   Y
─────                                                          ───

160        170        180        190        200
GTTAATCCTTTCAATGATGGTACTAAGTACAATGAGATGTTCAAAGGCAG
 V   N   P   F   N   D   G   T   K   Y   N   E   M   F   K   G   R
─────────────────────────────────────────────────────────────
                            CDR2

210        220        230        240        250
GGCCACACTGACTTCAGACAAATCCACCAGCACAGCCTACATGGAGCTCA
 A   T   L   T   S   D   K   S   T   S   T   A   Y   M   E   L 260        270        280        290        300
GCAGCCTGAGGTCTGAGGACTCTGCGGTCTATTACTGTGCAAGACAGGCT
 S   S   L   R   S   E   D   S   A   V   Y   Y   C   A   R   Q   A
                                                         ─────────

310        320        330        340
TGGGGTTACCCCTGGGGCCAAGGGACTCTGGTCACTGTCTCTTCT  (SEQ ID NO:58)
 W   G   Y   P   W   G   Q   G   T   L   V   T   V   S   S  (SEQ ID NO:34)
─────────────
   CDR3
```

FIG. 4B Heavy chain VH2

```
          10        20        30        40        50
GAGGTCCAGCTGGTGCAGTCTGGAGCTGAGGTGAAAAAGCCTGGGGCTTC
  E   V   Q   L   V   Q   S   G   A   E   V   K   K   P   G   A   S 60        70        80        90       100
AGTGAAGATGTCCTGCAAGGCTTCTGGATACACATTCACTAGCTATGTTA
  V   K   M   S   C   K   A   S   G   Y   T   F   T   S   Y   V
                                                   ‾‾‾‾‾‾‾‾‾
                                                      CDR1

110       120       130       140       150
TGCACTGGGTGAAGCAGGCCCCTGGGCAGCGCCTTGAGTGGATTGGATAT
  M   H   W   V   K   Q   A   P   G   Q   R   L   E   W   I   G   Y
 ‾‾‾‾‾                                                           ‾‾‾

160       170       180       190       200
GTTAATCCTTTCAATGATGGTACTAAGTACAATGAGATGTTCAAAGGCAG
  V   N   P   F   N   D   G   T   K   Y   N   E   M   F   K   G   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
              CDR2

210       220       230       240       250
GGCCACACTGACTTCAGACAAATCCACCAGCACAGCCTACATGGAGCTCA
  A   T   L   T   S   D   K   S   T   S   T   A   Y   M   E   L 260       270       280       290       300
GCAGCCTGAGGTCTGAGGACACTGCGGTCTATTACTGTGCAAGACAGGCT
  S   S   L   R   S   E   D   T   A   V   Y   Y   C   A   R   Q   A
                                                          ‾‾‾‾‾‾‾

310       320       330       340
TGGGGTTACCCCTGGGGCCAAGGGACTCTGGTCACTGTCTCTTCT  (SEQ ID NO:59)
  W   G   Y   P   W   G   Q   G   T   L   V   T   V   S   S  (SEQ ID NO:35)
 ‾‾‾‾‾‾‾‾‾‾‾‾‾
     CDR3
```

FIG. 4C Heavy chain VH3

```
            10         20         30         40         50
GAGGTCCAGCTGGTGCAGTCTGGAGCTGAGGTGAAAAAGCCTGGGGCTTC
 E   V   Q   L   V   Q   S   G   A   E   V   K   K   P   G   A   S 60         70         80         90        100
AGTGAAGATGTCCTGCAAGGCTTCTGGATACACATTCACTAGCTATGTTA
 V   K   M   S   C   K   A   S   G   Y   T   F   T   S   Y   V
                                                   ―――――――
                                                     CDR1

110        120        130        140        150
TGCACTGGGTGAGGCAGGCCCCTGGGCAGCGCCTTGAGTGGATTGGATAT
 M   H   W   V   R   Q   A   P   G   Q   R   L   E   W   I   G   Y
―――――                                                          ―

160        170        180        190        200
GTTAATCCTTTCAATGATGGTACTAAGTACAATGAGATGTTCAAAGGCAG
 V   N   P   F   N   D   G   T   K   Y   N   E   M   F   K   G   R
―――――――――――――――――――――――――――――――――――――――――――――――――――
                     CDR2

210        220        230        240        250
GGCCACACTGACTTCAGACAAATCCACCAGCACAGCCTACATGGAGCTCA
 A   T   L   T   S   D   K   S   T   S   T   A   Y   M   E   L 260        270        280        290        300
GCAGCCTGAGGTCTGAGGACACTGCGGTCTATTACTGTGCAAGACAGGCT
 S   S   L   R   S   E   D   T   A   V   Y   Y   C   A   R   Q   A
                                                         ―――――――

310        320        330        340
TGGGGTTACCCCTGGGGCCAAGGGACTCTGGTCACTGTCTCTTCT  (SEQ ID NO:60)
 W   G   Y   P   W   G   Q   G   T   L   V   T   V   S   S  (SEQ ID NO:36)
―――――――――――
  CDR3
```

FIG. 4D Heavy chain VH4

```
         10        20        30        40        50
GAGGTCCAGCTGGTGCAGTCTGGAGCTGAGGTGAAAAAGCCTGGGGCTTC
  E   V   Q   L   V   Q   S   G   A   E   V   K   K   P   G   A   S 60        70        80        90       100
AGTGAAGGTGTCCTGCAAGGCTTCTGGATACACATTCACTAGCTATGTTA
  V   K   V   S   C   K   A   S   G   Y   T   F   T   S   Y   V
                                                   ─────────
                                                     CDR1

110       120       130       140       150
TGCACTGGGTGAGGCAGGCCCCTGGGCAGCGCCTTGAGTGGATTGGATAT
  M   H   W   V   R   Q   A   P   G   Q   R   L   E   W   I   G   Y
 ─────                                                          ───

160       170       180       190       200
GTTAATCCTTTCAATGATGGTACTAAGTACAATGAGATGTTCAAAGGCAG
  V   N   P   F   N   D   G   T   K   Y   N   E   M   F   K   G   R
 ─────────────────────────────────────────────────
                    CDR2

210       220       230       240       250
GGCCACACTGACTTCAGACAAATCCACCAGCACAGCCTACATGGAGCTCA
  A   T   L   T   S   D   K   S   T   S   T   A   Y   M   E   L 260       270       280       290       300
GCAGCCTGAGGTCTGAGGACACTGCGGTCTATTACTGTGCAAGACAGGCT
  S   S   L   R   S   E   D   T   A   V   Y   Y   C   A   R   Q   A
                                                         ─────────

310       320       330       340
TGGGGTTACCCCTGGGGCCAAGGGACTCTGGTCACTGTCTCTTCT  (SEQ ID NO:61)
  W   G   Y   P   W   G   Q   G   T   L   V   T   V   S   S  (SEQ ID NO:37)
 ───────────────
      CDR3
```

FIG. 4E Heavy chain VH5

```
          10        20        30        40        50
GAGGTCCAGCTGGTGCAGTCTGGAGCTGAGGTGAAAAAGCCTGGGGCTTC
  E   V   Q   L   V   Q   S   G   A   E   V   K   K   P   G   A   S 60        70        80        90       100
AGTGAAGGTGTCCTGCAAGGCTTCTGGATACACATTCACTAGCTATGTTA
  V   K   V   S   C   K   A   S   G   Y   T   F   T   S   Y   V
                                                   ‾‾‾‾‾‾‾
                                                     CDR1

110       120       130       140       150
TGCACTGGGTGAGGCAGGCCCCTGGGCAGCGCCTTGAGTGGATTGGATAT
  M   H   W   V   R   Q   A   P   G   Q   R   L   E   W   I   G   Y
‾‾‾‾‾‾‾                                                         ‾‾‾

160       170       180       190       200
GTTAATCCTTTCAATGATGGTACTAAGTACAATGAGATGTTCAAAGGCAG
  V   N   P   F   N   D   G   T   K   Y   N   E   M   F   K   G   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                    CDR2

210       220       230       240       250
GGCCACAATCACTTCAGACAAATCCACCAGCACAGCCTACATGGAGCTCA
  A   T   I   T   S   D   K   S   T   S   T   A   Y   M   E   L 260       270       280       290       300
GCAGCCTGAGGTCTGAGGACACTGCGGTCTATTACTGTGCAAGACAGGCT
  S   S   L   R   S   E   D   T   A   V   Y   Y   C   A   R   Q   A
                                                         ‾‾‾‾‾‾‾‾‾

310       320       330       340
TGGGGTTACCCCTGGGGCCAAGGGACTCTGGTCACTGTCTCTTCT   (SEQ ID NO:62)
  W   G   Y   P   W   G   Q   G   T   L   V   T   V   S   S   (SEQ ID NO:38)
‾‾‾‾‾‾‾‾‾‾‾‾‾
     CDR3
```

FIGS. 5A-5D: Composite, Human Antibody Sequence Variants of Anti-PD-L1 Light Chains

FIG. 5A Light chain VK1

```
         10        20        30        40        50
GACATTGTGCTCACCCAATCTCCAGCTTCTTTGGCTCTGTCTCCCGGGGA
 D   I   V   L   T   Q   S   P   A   S   L   A   L   S   P   G   E 60        70        80        90        100
GAGAGCCACCCTCTCCTGCAGAGCCACTGAAAGTGTTGAATACTATGGCA
 R   A   T   L   S   C   R   A   T   E   S   V   E   Y   Y   G
                         ─────────────────────────────
                                    CDR1

110       120       130       140       150
CAAGTTTAGTGCAGTGGTACCAACAGAAACCAGGACAGCCACCCAAACTC
 T   S   L   V   Q   W   Y   Q   Q   K   P   G   Q   P   P   K   L
 ─────────────

160       170       180       190       200
CTCATCTATGCTGCATCCAGCGTAGATTCTGGGGTCCCTTCCAGGTTTAG
 L   I   Y   A   A   S   S   V   D   S   G   V   P   S   R   F   S
             ─────────────────────────
                      CDR2

210       220       230       240       250
TGGCAGTGGGTCTGGGACAGACTTCACCCTCACCATCAATTCTCTGGAGG
 G   S   G   S   G   T   D   F   T   L   T   I   N   S   L   E 260       270       280       290       300
AGGAGGATGCTGCAATGTATTTCTGTCAGCAAAGTAGGAGGGTTCCGTAC
 E   E   D   A   A   M   Y   F   C   Q   Q   S   R   R   V   P   Y
                                 ─────────────────────────
                                           CDR3

310       320       330
ACGTTCGGACAGGGGACCAAGCTGGAGATAAAA  (SEQ ID NO:63)
 T   F   G   Q   G   T   K   L   E   I   K   (SEQ ID NO:39)
 ───
```

FIG. 5B Light chain VK2

```
         10        20        30        40        50
GACATTGTGCTCACCCAATCTCCAGCTACTTTGTCTCTGTCTCCCGGGGA
 D  I  V  L  T  Q  S  P  A  T  L  S  L  S  P  G  E 60        70        80        90       100
GAGAGCCACCCTCTCCTGCAGAGCCACTGAAAGTGTTGAATACTATGGCA
 R  A  T  L  S  C  R  A  T  E  S  V  E  Y  Y  G
                   ─────────────────────────────────
                                 CDR1

110       120       130       140       150
CAAGTTTAGTGCAGTGGTACCAACAGAAACCAGGACAGCCACCCAAACTC
 T  S  L  V  Q  W  Y  Q  Q  K  P  G  Q  P  P  K  L
 ───────────────
```

FIG. 5C Light chain VK3

```
            10         20         30         40         50
GAGATTGTGCTCACCCAATCTCCAGCTACTTTGTCTCTGTCTCCCGGGGA
 E   I   V   L   T   Q   S   P   A   T   L   S   L   S   P   G   E 60         70         80         90        100
GAGAGCCACCCTCTCCTGCAGAGCCACTGAAAGTGTTGAATACTATGGCA
 R   A   T   L   S   C   R   A   T   E   S   V   E   Y   Y   G
                         ─────────────────────────────────────
                                        CDR1

110        120        130        140        150
CAAGTTTAGTGCAGTGGTACCAACAGAAACCAGGACAGCCACCCAAACTC
 T   S   L   V   Q   W   Y   Q   Q   K   P   G   Q   P   P   K   L
 ─────────────────

160        170        180        190        200
CTCATCTATGCTGCATCCAGCGTAGATTCTGGGGTCCCTTCCAGGTTTAG
 L   I   Y   A   A   S   S   V   D   S   G   V   P   S   R   F   S
         ─────────────────────────────
                    CDR2

210        220        230        240        250
TGGCAGTGGGTCTGGGACAGACTTCACCCTCACCATCAATTCTCTGGAGG
 G   S   G   S   G   T   D   F   T   L   T   I   N   S   L   E 260        270        280        290        300
CCGAGGATGCTGCAATGTATTTCTGTCAGCAAAGTAGGAGGGTTCCGTAC
 A   E   D   A   A   M   Y   F   C   Q   Q   S   R   R   V   P   Y
                                 ─────────────────────────────
                                                CDR3

310        320        330
ACGTTCGGACAGGGGACCAAGCTGGAGATAAAA  (SEQ ID NO:65)
 T   F   G   Q   G   T   K   L   E   I   K   (SEQ ID NO:41)
 ───
```

FIG. 5D Light chain VK4

```
          10         20         30         40         50
GACATTGTGCTCACCCAATCTCCAGCTACTTTGTCTCTGTCTCCCGGGGA
 D   I   V   L   T   Q   S   P   A   T   L   S   L   S   P   G   E 60         70         80         90        100
GAGAGCCACCCTCTCCTGCAGAGCCACTGAAAGTGTTGAATACTATGGCA
 R   A   T   L   S   C   R   A   T   E   S   V   E   Y   Y   G
                         ‾‾‾‾‾‾‾‾‾‾‾‾‾‾‾‾‾‾‾‾‾‾‾‾‾‾‾‾‾
                                      CDR1

110        120        130        140        150
CAAGTTTAGTGCAGTGGTACCAACAGAAACCAGGACAGCCACCCAAACTC
 T   S   L   V   Q   W   Y   Q   Q   K   P   G   Q   P   P   K   L
‾‾‾‾‾‾‾‾‾‾‾‾‾‾‾‾‾

160        170        180        190        200
CTCATCTATGCTGCATCCAGCGTAGATTCTGGGGTCCCTTCCAGGTTTAG
 L   I   Y   A   A   S   S   V   D   S   G   V   P   S   R   F   S
            ‾‾‾‾‾‾‾‾‾‾‾‾‾‾‾‾‾‾‾‾‾‾‾‾‾
                   CDR2

210        220        230        240        250
TGGCAGTGGGTCTGGGACAGACTTCACCCTCACCATCAATTCTCTGGAGG
 G   S   G   S   G   T   D   F   T   L   T   I   N   S   L   E 260        270        280        290        300
CCGAGGATGCTGCAACCTATTTCTGTCAGCAAAGTAGGAGGGTTCCGTAC
 A   E   D   A   A   T   Y   F   C   Q   Q   S   R   R   V   P   Y
                                ‾‾‾‾‾‾‾‾‾‾‾‾‾‾‾‾‾‾‾‾‾‾‾‾‾‾‾
                                              CDR3

310        320        330
ACGTTCGGACAGGGGACCAAGCTGGAGATAAAA  (SEQ ID NO:66)
 T   F   G   Q   G   T   K   L   E   I   K    (SEQ ID NO:42)
‾‾‾‾‾
```

FIGS. 6A-6E: Composite, human Antibody Sequence Variants of Anti-PD-L2 Heavy Chains

FIG. 6A Heavy chain VH1

```
        10        20        30        40        50
CAGGTCCAGCTGGTGCAGTCTGGAGCTGAACTGAAGAAACCTGGGGCCTC
 Q   V   Q   L   V   Q   S   G   A   E   L   K   K   P   G   A   S 60        70        80        90       100
AGTGAAGATGTCCTGCAAGGCTTCTGGCTACACCTTTACTGGCTACACGA
  V   K   M   S   C   K   A   S   G   Y   T   F   T   G   Y   T
                                                   ‾‾‾‾‾‾‾‾‾‾‾
                                                        CDR1

110       120       130       140       150
TGCACTGGGTAAAACAGGCCCCTGGACAGGGTCTGGAATGGATTGGATAC
 M   H   W   V   K   Q   A   P   G   Q   G   L   E   W   I   G   Y
‾‾‾‾‾‾‾                                                        ‾‾‾

160       170       180       190       200
ATTAATCCTAGAAGTGGATATACTGAGTATAATCAGAAGTTCAAGGACAG
  I   N   P   R   S   G   Y   T   E   Y   N   Q   K   F   K   D   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                   CDR2

210       220       230       240       250
GACCACATTGACTGCAGACAAATCTACCAGCACAGCCTACATGGAACTGA
  T   T   L   T   A   D   K   S   T   S   T   A   Y   M   E   L 260       270       280       290       300
GCAGCCTGAGATCTGAGGACTCTGCGGTCTATTATTGTGCAAGACCCTGG
  S   S   L   R   S   E   D   S   A   V   Y   Y   C   A   R   P   W
                                                           ‾‾‾‾‾‾‾

310       320       330       340
TTTGCTTACTGGGGCCAAGGGACTCTGGTCACTGTCTCTTCA (SEQ ID NO:67)
  F   A   Y   W   G   Q   G   T   L   V   T   V   S   S  (SEQ ID NO:43)
‾‾‾‾‾‾‾‾‾‾‾
  CDR3
```

FIG. 6B Heavy chain VH2

```
         10        20        30        40        50
CAGGTCCAGCTGGTGCAGTCTGGAGCTGAAGTGAAGAAACCTGGGGCCTC
 Q   V   Q   L   V   Q   S   G   A   E   V   K   K   P   G   A   S 60        70        80        90       100
AGTGAAGATGTCCTGCAAGGCTTCTGGCTACACCTTTACTGGCTACACGA
 V   K   M   S   C   K   A   S   G   Y   T   F   T   G   Y   T
                                                    ‾‾‾‾‾‾‾
                                                      CDR1

110       120       130       140       150
TGCACTGGGTAAAACAGGCCCCTGGACAGGGTCTGGAATGGATTGGATAC
 M   H   W   V   K   Q   A   P   G   Q   G   L   E   W   I   G   Y
‾‾‾‾‾‾‾                                                         ‾‾‾

160       170       180       190       200
ATTAATCCTAGAAGTGGATATACTGAGTATAATCAGAAGTTCAAGGACAG
 I   N   P   R   S   G   Y   T   E   Y   N   Q   K   F   K   D   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                       CDR2

210       220       230       240       250
GACCACATTGACTGCAGACAAATCTACCAGCACAGCCTACATGGAACTGA
 T   T   L   T   A   D   K   S   T   S   T   A   Y   M   E   L 260       270       280       290       300
GCAGCCTGAGATCTGAGGACACTGCGGTCTATTATTGTGCAAGACCCTGG
 S   S   L   R   S   E   D   T   A   V   Y   Y   C   A   R   P   W
                                                        ‾‾‾‾‾‾‾‾‾

310       320       330       340
TTTGCTTACTGGGGCCAAGGGACTCTGGTCACTGTCTCTTCA (SEQ ID NO:68)
 F   A   Y   W   G   Q   G   T   L   V   T   V   S   S  (SEQ ID NO:44)
‾‾‾‾‾‾‾‾‾‾‾
   CDR3
```

FIG. 6C Heavy chain VH3

```
         10         20         30         40         50
CAGGTCCAGCTGGTGCAGTCTGGAGCTGAAGTGAAGAAACCTGGGGCCTC
 Q   V   Q   L   V   Q   S   G   A   E   V   K   K   P   G   A   S 60         70         80         90        100
AGTGAAGATGTCCTGCAAGGCTTCTGGCTACACCTTTACTGGCTACACGA
 V   K   M   S   C   K   A   S   G   Y   T   F   T   G   Y   T
                                                   ‾‾‾‾‾‾‾‾‾
                                                      CDR1

110        120        130        140        150
TGCACTGGGTAAGACAGGCCCCTGGACAGGGTCTGGAATGGATTGGATAC
 M   H   W   V   R   Q   A   P   G   Q   G   L   E   W   I   G   Y
‾‾‾‾‾‾‾                                                       ‾‾‾

160        170        180        190        200
ATTAATCCTAGAAGTGGATATACTGAGTATAATCAGAAGTTCAAGGACAG
 I   N   P   R   S   G   Y   T   E   Y   N   Q   K   F   K   D   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                          CDR2

210        220        230        240        250
GACCACATTGACTGCAGACAAATCTACCAGCACAGCCTACATGGAACTGA
 T   T   L   T   A   D   K   S   T   S   T   A   Y   M   E   L 260        270        280        290        300
GCAGCCTGAGATCTGAGGACACTGCGGTCTATTATTGTGCAAGACCCTGG
 S   S   L   R   S   E   D   T   A   V   Y   Y   C   A   R   P   W
                                                       ‾‾‾‾‾‾‾‾‾

310        320        330        340
TTTGCTTACTGGGGCCAAGGGACTCTGGTCACTGTCTCTTCA   (SEQ ID NO:69)
 F   A   Y   W   G   Q   G   T   L   V   T   V   S   S   (SEQ ID NO:45)
‾‾‾‾‾‾‾‾‾
  CDR3
```

FIG. 6D Heavy chain VH4

```
         10         20         30         40         50
CAGGTCCAGCTGGTGCAGTCTGGAGCTGAAGTGAAGAAACCTGGGGCCTC
  Q   V   Q   L   V   Q   S   G   A   E   V   K   K   P   G   A   S 60         70         80         90        100
AGTGAAGGTGTCCTGCAAGGCTTCTGGCTACACCTTTACTGGCTACACGA
  V   K   V   S   C   K   A   S   G   Y   T   F   T   G   Y   T
                                                    ─────────────
                                                        CDR1

110        120        130        140        150
TGCACTGGGTAAGACAGGCCCCTGGACAGGGTCTGGAATGGATTGGATAC
  M   H   W   V   R   Q   A   P   G   Q   G   L   E   W   I   G   Y
 ─────                                                         ───

160        170        180        190        200
ATTAATCCTAGAAGTGGATATACTGAGTATAATCAGAAGTTCAAGGACAG
  I   N   P   R   S   G   Y   T   E   Y   N   Q   K   F   K   D   R
 ──────────────────────────────────────────────────────────────────
                   CDR2

210        220        230        240        250
GACCACATTGACTGCAGACAAATCTACCAGCACAGCCTACATGGAACTGA
  T   T   L   T   A   D   K   S   T   S   T   A   Y   M   E   L 260        270        280        290        300
GCAGCCTGAGATCTGAGGACACTGCGGTCTATTATTGTGCAAGACCCTGG
  S   S   L   R   S   E   D   T   A   V   Y   Y   C   A   R   P   W
                                                            ───────

310        320        330        340
TTTGCTTACTGGGGCCAAGGGACTCTGGTCACTGTCTCTTCA    (SEQ ID NO:70)
  F   A   Y   W   G   Q   G   T   L   V   T   V   S   S    (SEQ ID NO:46)
 ─────────
   CDR3
```

FIG. 6E Heavy chain VH5

```
          10         20         30         40         50
CAGGTCCAGCTGGTGCAGTCTGGAGCTGAAGTGAAGAAACCTGGGGCCTC
  Q   V   Q   L   V   Q   S   G   A   E   V   K   K   P   G   A   S 60         70         80         90        100
AGTGAAGGTGTCCTGCAAGGCTTCTGGCTACACCTTTACTGGCTACACGA
   V   K   V   S   C   K   A   S   G   Y   T   F   T   G   Y   T
                                                    ‾‾‾‾‾‾‾‾‾‾‾
                                                       CDR1

110        120        130        140        150
TGCACTGGGTAAGACAGGCCCCTGGACAGGGTCTGGAATGGATTGGATAC
 M   H   W   V   R   Q   A   P   G   Q   G   L   E   W   I   G   Y
                                                                ‾‾‾

160        170        180        190        200
ATTAATCCTAGAAGTGGATATACTGAGTATAATCAGAAGTTCAAGGACAG
  I   N   P   R   S   G   Y   T   E   Y   N   Q   K   F   K   D   R
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
              CDR2

210        220        230        240        250
GACCACAATCACTGCAGACAAATCTACCAGCACAGCCTACATGGAACTGA
   T   T   I   T   A   D   K   S   T   S   T   A   Y   M   E   L 260        270        280        290        300
GCAGCCTGAGATCTGAGGACACTGCGGTCTATTATTGTGCAAGACCCTGG
   S   S   L   R   S   E   D   T   A   V   Y   Y   C   A   R   P   W
                                                            ‾‾‾‾‾‾‾

310        320        330        340
TTTGCTTACTGGGGCCAAGGGACTCTGGTCACTGTCTCTTCA   (SEQ ID NO:71)
   F   A   Y   W   G   Q   G   T   L   V   T   V   S   S   (SEQ ID NO:47)
‾‾‾‾‾‾‾‾‾‾
   CDR3
```

FIGS. 7A-7D: Composite, human Antibody Sequence Variants of Anti-PD-L2 Light Chains

FIG. 7A Light chain VK1

```
         10        20        30        40        50
GACATTGTGATGACACAGTCTCCAGCCTCCCTGACTGTGACACCAGGAGA
 D   I   V   M   T   Q   S   P   A   S   L   T   V   T   P   G   E 60        70        80        90       100
GAAGGTCACTATCACCTGCAAGTCCAGTCAGAGTCTGTTAAACAGTGGAA
  K   V   T   I   T   C   K   S   S   Q   S   L   L   N   S   G
                          ─────────────────────────────
                                       CDR1

110       120       130       140       150
ATCAAAAGAACTACTTGACCTGGTACCAGCAGAAACCAGGGCAGCCTCCT
  N   Q   K   N   Y   L   T   W   Y   Q   Q   K   P   G   Q   P   P
  ───────────────────────

160       170       180       190       200
AAACTGTTGATCTACTGGGCATCCACTAGGGAATCTGGGGTCCCTGATCG
   K   L   L   I   Y   W   A   S   T   R   E   S   G   V   P   D   R
                      ─────────────────────────
                              CDR2

210       220       230       240       250
CTTCACAGGCAGTGGATCTGGAACAGATTTCACTCTCACCATCAGCAGTC
   F   T   G   S   G   S   G   T   D   F   T   L   T   I   S   S 260       270       280       290       300
TGCAGGCTGAAGACGTGGCAGTTTATTACTGTCAGAATGATTATAGTTAT
   L   Q   A   E   D   V   A   V   Y   Y   C   Q   N   D   Y   S   Y
                                      ─────────────────────
                                               CDR3

310       320       330
CCTCTCACGTTCGGTCAGGGGACCAAGCTGGAGATCAAA (SEQ ID NO:72)
   P   L   T   F   G   Q   G   T   K   L   E   I   K  (SEQ ID NO:48)
  ─────────────
```

FIG. 7B Light chain VK2

```
          10        20        30        40        50
GACATTGTGATGACACAGTCTCCAGCCTCCCTGTCTGTGACACCAGGAGA
  D  I  V  M  T  Q  S  P  A  S  L  S  V  T  P  G  E 60        70        80        90       100
GAAGGTCACTATCACCTGCAAGTCCAGTCAGAGTCTGTTAAACAGTGGAA
  K  V  T  I  T  C  K  S  S  Q  S  L  L  N  S  G
                    ─────────────────────────────────
                                                CDR1

110       120       130       140       150
ATCAAAAGAACTACTTGACCTGGTACCAGCAGAAACCAGGGCAGCCTCCT
  N  Q  K  N  Y  L  T  W  Y  Q  Q  K  P  G  Q  P  P
  ──────────────────

160       170       180       190       200
AAACTGTTGATCTACTGGGCATCCACTAGGGAATCTGGGGTCCCTGATCG
  K  L  L  I  Y  W  A  S  T  R  E  S  G  V  P  D  R
                 ───────────────────────
                            CDR2

210       220       230       240       250
CTTCACAGGCAGTGGATCTGGAACAGATTTCACTCTCACCATCAGCAGTC
  F  T  G  S  G  S  G  T  D  F  T  L  T  I  S  S 260       270       280       290       300
TGCAGGCTGAAGACGTGGCAGTTTATTACTGTCAGAATGATTATAGTTAT
  L  Q  A  E  D  V  A  V  Y  Y  C  Q  N  D  Y  S  Y
                                ─────────────────────
                                                CDR3

310       320       330
CCTCTCACGTTCGGTCAGGGGACCAAGCTGGAGATCAAA (SEQ ID NO:73)
  P  L  T  F  G  Q  G  T  K  L  E  I  K  (SEQ ID NO:49)
  ─────────
```

FIG. 7C Light chain VK3

```
         10        20        30        40        50
GACATTGTGATGACACAGTCTCCAGCCTTCCTGTCTGTGACACCAGGAGA
 D  I  V  M  T  Q  S  P  A  F  L  S  V  T  P  G  E 60        70        80        90       100
GAAGGTCACTATCACCTGCAAGTCCAGTCAGAGTCTGTTAAACAGTGGAA
 K  V  T  I  T  C  K  S  S  Q  S  L  L  N  S  G
                   ─────────────────────────────
                                CDR1

110       120       130       140       150
ATCAAAAGAACTACTTGACCTGGTACCAGCAGAAACCAGGGCAGCCTCCT
 N  Q  K  N  Y  L  T  W  Y  Q  Q  K  P  G  Q  P  P
 ─────────────────

160       170       180       190       200
AAACTGTTGATCTACTGGGCATCCACTAGGGAATCTGGGGTCCCTGATCG
 K  L  L  I  Y  W  A  S  T  R  E  S  G  V  P  D  R
              ───────────────────────
                       CDR2

210       220       230       240       250
CTTCACAGGCAGTGGATCTGGAACAGATTTCACTCTCACCATCAGCAGTC
 F  T  G  S  G  S  G  T  D  F  T  L  T  I  S  S 260       270       280       290       300
TGCAGGCTGAAGACGTGGCAGTTTATTACTGTCAGAATGATTATAGTTAT
 L  Q  A  E  D  V  A  V  Y  Y  C  Q  N  D  Y  S  Y
                             ──────────────────────
                                           CDR3

310       320       330
CCTCTCACGTTCGGTCAGGGGACCAAGCTGGAGATCAAA (SEQ ID NO:74)
 P  L  T  F  G  Q  G  T  K  L  E  I  K  (SEQ ID NO:50)
 ────────
```

FIG. 7D Light chain VK4

```
         10        20        30        40        50
GACATTGTGATGACACAGTCTCCAGCCTTCCTGTCTGTGACACCAGGAGA
 D   I   V   M   T   Q   S   P   A   F   L   S   V   T   P   G   E 60        70        80        90       100
GAAGGTCACTATCACCTGCAAGTCCAGTCAGAGTCTGTTAAACAGTGGAA
  K   V   T   I   T   C   K   S   S   Q   S   L   L   N   S   G
                          ─────────────────────────────────
                                        CDR1

110       120       130       140       150
ATCAAAAGAACTACTTGACCTGGTACCAGCAGAAACCAGGGCAGCCTCCT
  N   Q   K   N   Y   L   T   W   Y   Q   Q   K   P   G   Q   P   P
 ─────────────────────────

160       170       180       190       200
AAACTGTTGATCTACTGGGCATCCACTAGGGAATCTGGGGTCCCTGATCG
  K   L   L   I   Y   W   A   S   T   R   E   S   G   V   P   D   R
                  ─────────────────────────────
                              CDR2

210       220       230       240       250
CTTCTCCGGCAGTGGATCTGGAACAGATTTCACTCTCACCATCAGCAGTC
  F   S   G   S   G   S   G   T   D   F   T   L   T   I   S   S 260       270       280       290       300
TGCAGGCTGAAGACGTGGCAGTTTATTACTGTCAGAATGATTATAGTTAT
  L   Q   A   E   D   V   A   V   Y   Y   C   Q   N   D   Y   S   Y
                                      ─────────────────────────
                                                    CDR3

310       320       330
CCTCTCACGTTCGGTCAGGGGACCAAGCTGGAGATCAAA  (SEQ ID NO:75)
  P   L   T   F   G   Q   G   T   K   L   E   I   K   (SEQ ID NO:51)
 ─────────
```

FIGS. 8A-8C: Purification of EH12.2H7 Composite, human Antibodies
FIG. 8A Coomassie Blue Stained SDS-PAGE of Purified EH12.2H7 Antibodies:
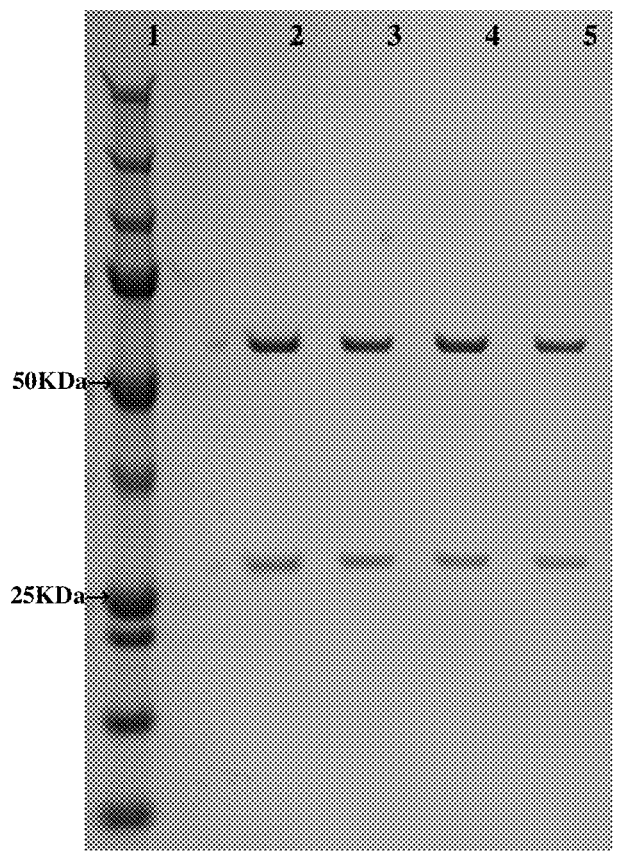
Lane 1: Bio-Rad Precision Marker
Lane 2: VH4/Vκ4
Lane 3: VH4/Vκ3
Lane 4: VH3/Vκ4
Lane 5: VH3/Vκ3
1μg of each antibody was loaded FIG. 8B Coomassie Blue Stained SDS-PAGE of Purified 29E.2A3 Antibodies:
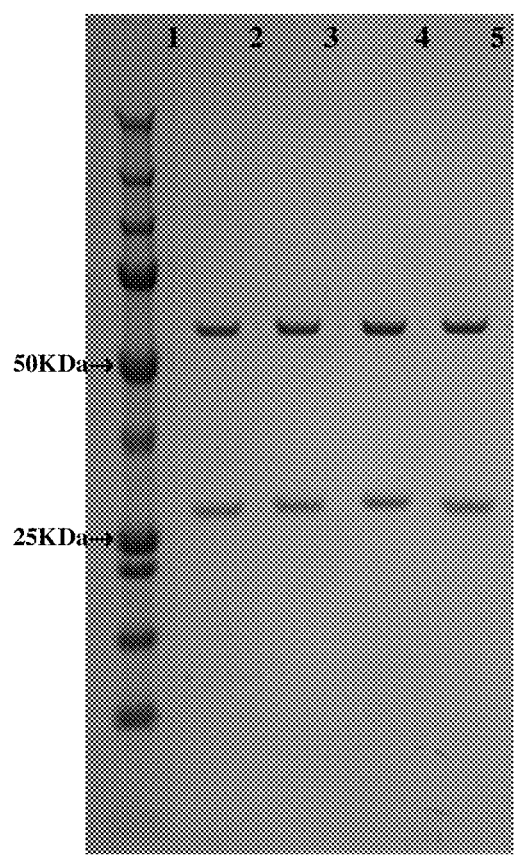
Lane 1: Bio-Rad Precision Marker
Lane 2: VH4/Vκ2
Lane 3: VH2/Vκ4
Lane 4: VH2/Vκ1
Lane 5: VH2/Vκ2
1μg of each antibody was loaded

FIG. 8C Coomassie Blue Stained SDS-PAGE of Purified 24F.10C12 Antibodies:
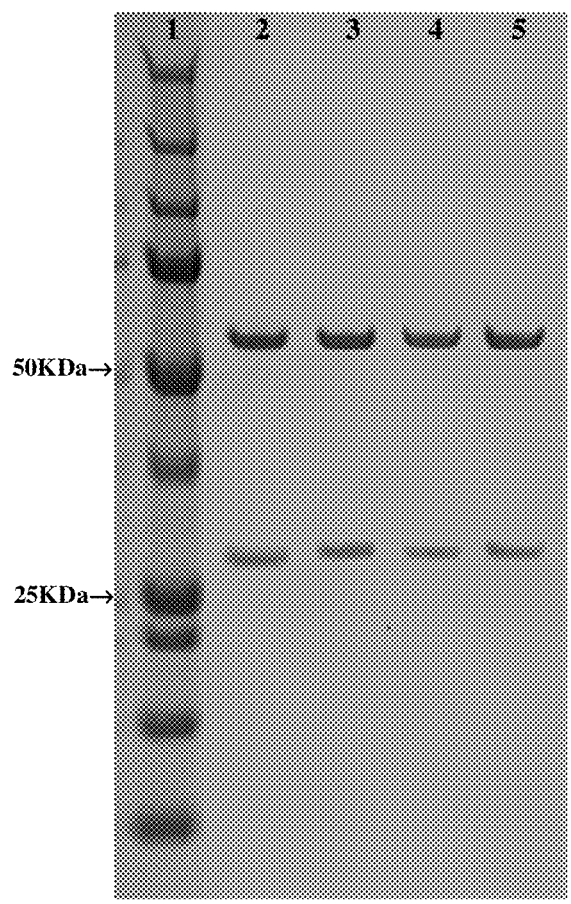
Lane 1: Bio-Rad Precision Marker
Lane 2: VH4/Vκ4
Lane 3: VH4/Vκ2
Lane 4: VH2/Vκ3
Lane 5: VH2/Vκ2
1μg of each antibody was loaded FIGS. 9A-9C: Comparison of Composite, human Antibodies Activities to Mouse Reference Antibody
FIG. 9A Human PD-1 Competition ELISA:
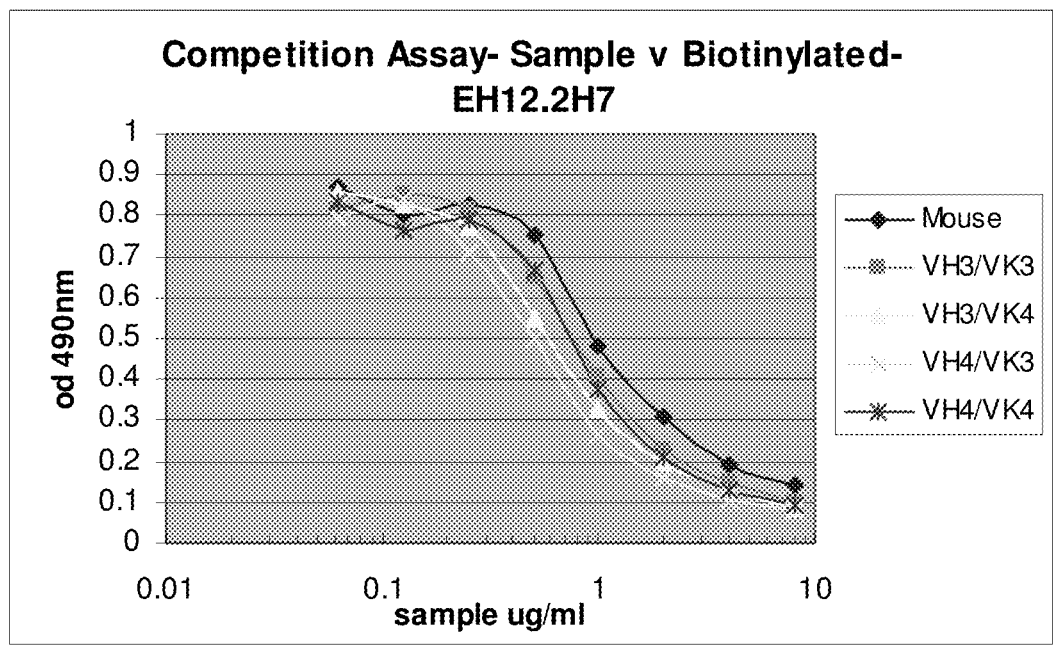

FIG. 9B Human PD-L1 Competition ELISA:
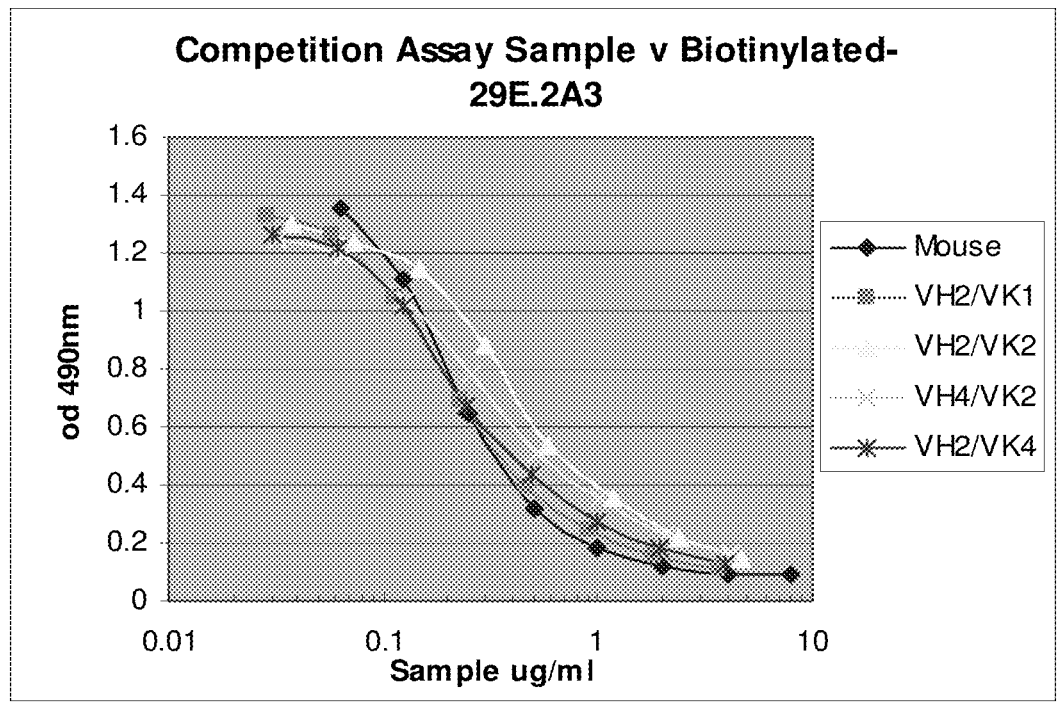

FIG. 9C Human PD-L2 Competition ELISA:
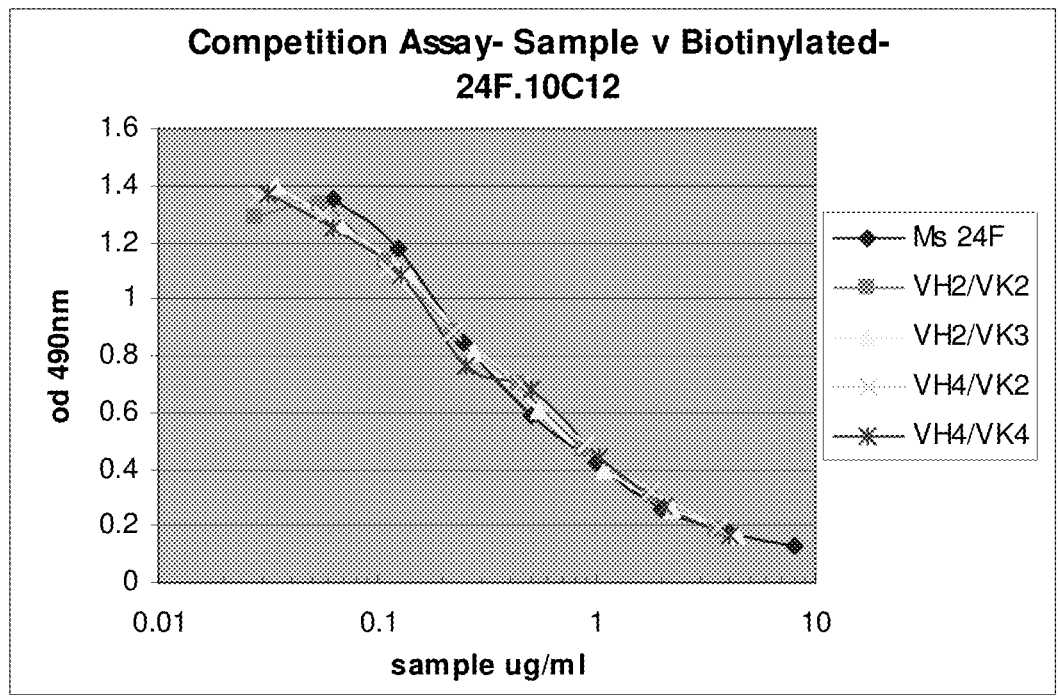

FIGS. 10A-10C: $IC_{50}$ Binding Comparing Mouse anti-Human Antibodies with Composite, Human Antibodies FIG. 10A Competition with EH12.2H7 for binding to PD-1

|     | VH1  | VH2  | VH3  | VH4  | VH5 |
|-----|------|------|------|------|-----|
| VK1 | 0.82 | 0.78 | 0.82 | 0.77 | ND  |
| VK2 | 0.66 | 0.98 | 0.82 | 0.98 | ND  |
| VK3 | 0.82 | 0.98 | 0.76 | 0.46 | ND  |
| VK4 | ND   | 0.90 | 0.60 | 0.74 | ND  |

FIG. 10B Competition with 20E.283 for binding to PD-L1

|     | VH1  | VH2  | VH3  | VH4  | VH5  |
|-----|------|------|------|------|------|
| VK1 | 3.61 | 0.96 | 3.21 | 2.10 | 5.96 |
| VK2 | 3.34 | 1.75 | 1.68 | 3.00 | 7.8  |
| VK3 | 2.26 | 2.26 | 1.92 | 3.16 | 9.16 |
| VK4 | 5.10 | 1.04 | 1.64 | 2.96 | 7.04 |

FIG. 10C Competition with 24F.10C12 for binding to PD-L2

|     | VH1  | VH2  | VH3  | VH4  | VH5 |
|-----|------|------|------|------|-----|
| VK1 | 0.82 | 0.78 | 0.82 | 0.77 | ND  |
| VK2 | 0.66 | 0.98 | 0.82 | 0.98 | ND  |
| VK3 | 0.82 | 0.98 | 0.76 | 0.46 | ND  |
| VK4 | ND   | 0.90 | 0.60 | 0.74 | ND  |

FIG. 11: Amino Acid Sequences for PD-1, PD-L1 and PD-L2

PD-1 amino acid sequence (SEQ ID NO: 2)

```
MQIPQAPWPV VWAVLQLGWR PGWFLDSPDR PWNPPTFSPA LLVVTEGDNA  50
TFTCSFSNTS ESFVLNWYRM SPSNQTDKLA AFPEDRSQPG QDCRFRVTQL 100
PNGRDFHMSV VRARRNDSGT YLCGAISLAP KAQIKESLRA ELRVTERRAE 150
VPTAHPSPSP RPAGQFQTLV VGVVGGLLGS LVLLVWVLAV ICSRAARGTI 200
GARRTGQPLK EDPSAVPVFS VDYGELDFQW REKTPEPPVP CVPEQTEYAT 250
IVFPSGMGTS SPARRGSADG PRSAQPLRPE DGHCSWPL             288
```

PD-L1 amino acid sequence (SEQ ID NO: 4)

```
MRIFAVFIFM TYWHLLNAFT VTVPKDLYVV EYGSNMTIEC KFPVEKQLDL  50
AALIVYWEME DKNIIQFVHG EEDLKVQHSS YRQRARLLKD QLSLGNAALQ 100
ITDVKLQDAG VYRCMISYGG ADYKRITVKV NAPYNKINQR ILVVDPVTSE 150
HELTCQAEGY PKAEVIWTSS DHQVLSGKTT TTNSKREEKL FNVTSTLRIN 200
TTTNEIFYCT FRRLDPEENH TAELVIPELP LAHPPNERTH LVILGAILLC 250
LGVALTFIFR LRKGRMMDVK KCGIQDTNSK KQSDTHLEET           290
```

PD-L2 amino acid sequence (SEQ ID NO: 6)

```
MIFLLLMLSL ELQLHQIAAL FTVTVPKELY IIEHGSNVTL ECNFDTGSHV  50
NLGAITASLQ KVENDTSPHR ERATLLEEQL PLGKASFHIP QVQVRDEGQY 100
QCIIIYGVAW DYKYLTLKVK ASYRKINTHI LKVPETDEVE LTCQATGYPL 150
AEVSWPNVSV PANTSHSRTP EGLYQVTSVL RLKPPPGRNF SCVFWNTHVR 200
ELTLASIDLQ SQMEPRTHPT WLLHIFIPFC IIAFIFIATV IALRKQLCQK 250
LYSSKDTTKR PVTTTKREVN SAI                            273
```

FIG. 12 CDR Amino Acid Sequences for Composite, Human Antibodies

| Antibody | Chain | CDR | Sequence | SEQ ID NO. |
|---|---|---|---|---|
| Anti-PD-1 | Heavy | CDR1 | SSWIH | 7 |
| | | CDR2 | YIYPSTGFTEYNQKFKD | 8 |
| | | CDR3 | WRDSSGYHAMDY | 9 |
| | Light | CDR1 | RASQSVSTSGYSYMH | 10 |
| | | CDR2 | FGSNLES | 11 |
| | | CDR3 | QHSWEIPYT | 12 |
| Anti-PD-L1 | Heavy | CDR1 | SYVMH | 13 |
| | | CDR2 | YVNPFNDGTKYNEMFKG | 14 |
| | | CDR3 | QAWGYP | 15 |
| | Light | CDR1 | RATESVEYYGTSLVQ | 16 |
| | | CDR2 | AASSVDS | 17 |
| | | CDR3 | QQSRRVPYT | 18 |
| Anti-PD-L2 | Heavy | CDR1 | GYTMH | 19 |
| | | CDR2 | YINPRSGYTEYNQKFKD | 20 |
| | | CDR3 | PWFAY | 21 |
| | Light | CDR1 | KSSQSLLNSGNQKNYLT | 22 |
| | | CDR2 | WASTRES | 23 |
| | | CDR3 | QNDYSYPLT | 24 |

FIG. 13 The amino acid sequences for the heavy and light chains of composite human antibody variable regions.

Anti-PD-1 Heavy Chain VH1 (SEQ ID NO 25)
QVQLVQSGAELKQPGASVKMSCKASGYSFTSSWIHWVKQAPGQGLEWIGYIYPSTGFTEYNQKFKDRA
TLTADKSTSTAYMELSSLRSEDSAVYYCARWRDSSGYHAMDYWGQGTSVTVSS

Anti-PD-1 Heavy Chain VH2 (SEQ ID NO 26)
QVQLVQSGAEVKQPGASVKMSCKASGYSFTSSWIHWVKQAPGQGLEWIGYIYPSTGFTEYNQKFKDRA
TLTADKSTSTAYMELSSLRSEDTAVYYCARWRDSSGYHAMDYWGQGTSVTVSS

Anti-PD-1 Heavy Chain VH3 (SEQ ID NO 27)
QVQLVQSGHEVKQPGASVKMSCKASGYSFTSSWIHWVKQAPGQGLEWIGYIYPSTGFTEYNQKFKDRA
TLTADKSTSTAYMELSSLRSEDTAVYYCARWRDSSGYHAMDYWGQGTLVTVSS

Anti-PD-1 Heavy Chain VH4 (SEQ ID NO 28)
QVQLVQSGHEVKQPGASVKMSCKASGYSFTSSWIHWVRQAPGQGLEWIGYIYPSTGFTEYNQKFKDRA
TLTADKSTSTAYMELSSLRSEDTAVYYCARWRDSSGYHAMDYWGQGTLVTVSS

Anti-PD-1 Heavy Chain VH5 (SEQ ID NO 29)
QVQLVQSGHEVKQPGASVKVSCKASGYSFTSSWIHWVRQAPGQGLEWIGYIYPSTGFTEYNQKFKDRA
TITADKSTSTAYMELSSLRSEDTAVYYCARWRDSSGYHAMDYWGQGTLVTVSS

Anti-PD-1 Light Chain VK1 (SEQ ID NO 30)
DIVLTQSPASLTLSPGQRLTISCRASQSVSTSGYSYMHWYQQKPDQSPKLLIKFGSNLESGIPARFSG
SGSGTDFTLTISSLEEEDFATYYCQHSWEIPYTFGQGTKLEIK

Anti-PD-1 Light Chain VK2 (SEQ ID NO 31)
DIVLTQSPATLSLSPGQRLTISCRASQSVSTSGYSYMHWYQQKPDQSPKLLIKFGSNLESGIPARFSG
SGSGTDFTLTISSLEPEDFATYYCQHSWEIPYTFGQGTKLEIK

Anti-PD-1 Light Chain VK3 (SEQ ID NO 32)
EIVLTQSPATLSLSPGQRLTISCRASQSVSTSGYSYMHWYQQKPDQSPKLLIKFGSNLESGIPARFSG
SGSGTDFTLTISSLEPEDFATYYCQHSWEIPYTFGQGTKLEIK

Anti-PD-1 Light Chain VK4 (SEQ ID NO 33)
DIVLTQSPATLSLSPGQRLTISCRASQSVSTSGYSYMHWYQQKPDQSPKLLIKFGSNLESGIPARFSG
SGSGTDFTLTISSLEPEDFAVYYCQHSWEIPYTFGQGTKLEIK

Anti-PD-L1 Heavy Chain VH1 (SEQ ID NO 34)
EVQLVQSGPELKKPGASVKMSCKASGYTFTSYVMHWVKQAPGQRLEWIGYVNPFNDGTKYNEMFKGRA
TLTSDKSTSTAYMELSSLRSEDSAVYYCARQAWGYPWGQGTLVTVSS

Anti-PD-L1 Heavy Chain VH2 (SEQ ID NO 35)
EVQLVQSGAEVKKPGASVKMSCKASGYTFTSYVMHWVKQAPGQRLEWIGYVNPFNDGTKYNEMFKGRA
TLTSDKSTSTAYMELSSLRSEDTAVYYCARQAWGYPWGQGTLVTVSS

FIG. 13 (Continued)

Anti-PD-L1 Heavy Chain VH3 (SEQ ID NO 36)
EVQLVQSGAEVKKPGASVKMSCKASGYTFTSYVMHWVRQAPGQRLEWIGYVNPFNDGTKYNEMFKGRA
TLTSDKSTSTAYMELSSLRSEDTAVYYCARQAWGYPWGQGTLVTVSS

Anti-PD-L1 Heavy Chain VH4 (SEQ ID NO 37)
EVQLVQSGAEVKKPGASVKVSCKASGYTFTSYVMHWVRQAPGQRLEWIGYVNPFNDGTKYNEMFKGRA
TLTSDKSTSTAYMELSSLRSEDTAVYYCARQAWGYPWGQGTLVTVSS

Anti-PD-L1 Heavy Chain VH5 (SEQ ID NO 38)
EVQLVQSGAEVKKPGASVKVSCKASGYTFTSYVMHWVRQAPGQRLEWIGYVNPFNDGTKYNEMFKGRA
TITSDKSTSTAYMELSSLRSEDTAVYYCARQAWGYPWGQGTLVTVSS

Anti-PD-L1 Light Chain VK1 (SEQ ID NO 39)
DIVLTQSPASLALSPGERATLSCRATESVEYYGTSLVQWYQQKPGQPPKLLIYAASSVDSGVPSRFSG
SGSGTDFTLTINSLEEEDAAMYFCQQSRRVPYTFGQGTKLEIK

Anti-PD-L1 Light Chain VK2 (SEQ ID NO 40)
DIVLTQSPATLSLSPGERATLSCRATESVEYYGTSLVQWYQQKPGQPPKLLIYAASSVDSGVPSRFSG
SGSGTDFTLTINSLEAEDAAMYFCQQSRRVPYTFGQGTKLEIK

Anti-PD-L1 Light Chain VK3 (SEQ ID NO 41)
EIVLTQSPATLSLSPGERATLSCRATESVEYYGTSLVQWYQQKPGQPPKLLIYAASSVDSGVPSRFSG
SGSGTDFTLTINSLEAEDAAMYFCQQSRRVPYTFGQGTKLEIK

Anti-PD-L1 Light Chain VK4 (SEQ ID NO 42)
DIVLTQSPATLSLSPGERATLSCRATESVEYYGTSLVQWYQQKPGQPPKLLIYAASSVDSGVPSRFSG
SGSGTDFTLTINSLEAEDAATYFCQQSRRVPYTFGQGTKLEIK

Anti-PD-L2 Heavy Chain VH1 (SEQ ID NO 43)
QVQLVQSGAELKKPGASVKMSCKASGYTFTGYTMHWVKQAPGQGLEWIGYINPRSGYTEYNQKFKDRT
TLTADKSTSTAYMELSSLRSEDSAVYYCARPWFAYWGQGTLVTVSS

Anti-PD-L2 Heavy Chain VH2 (SEQ ID NO 44)
QVQLVQSGAEVKKPGASVKMSCKASGYTFTGYTMHWVKQAPGQGLEWIGYINPRSGYTEYNQKFKDRT
TLTADKSTSTAYMELSSLRSEDTAVYYCARPWFAYWGQGTLVTVSS

Anti-PD-L2 Heavy Chain VH3 (SEQ ID NO 45)
QVQLVQSGAEVKKPGASVKMSCKASGYTFTGYTMHWVRQAPGQGLEWIGYINPRSGYTEYNQKFKDRT
TLTADKSTSTAYMELSSLRSEDTAVYYCARPWFAYWGQGTLVTVSS

Anti-PD-L2 Heavy Chain VH4 (SEQ ID NO 46)
QVQLVQSGAEVKKPGASVKVSCKASGYTFTGYTMHWVRQAPGQGLEWIGYINPRSGYTEYNQKFKDRT
TLTADKSTSTAYMELSSLRSEDTAVYYCARPWFAYWGQGTLVTVSS

FIG. 13 (Continued)

Anti-PD-L2 Heavy Chain VH5 (SEQ ID NO 47)
QVQLVQSGAEVKKPGASVKVSCKASGYTFTGYTMHWVRQAPGQGLEWIGYINPRSGYTEYNQKFKDRT
TITADKSTSTAYMELSSLRSEDTAVYYCARPWFAYWGQGTLVTVSS

Anti-PD-L2 Light Chain VK1 (SEQ ID NO 48)
DIVMTQSPASLTVTPGEKVTITCKSSQSLLNSGNQKNYLTWYQQKPGQPPKLLIYWASTRESGVPDRF
TGSGSGTDFTLTISSLQAEDVAVYYCQNDYSYPLTFGQGTKLEIK

Anti-PD-L2 Light Chain VK2 (SEQ ID NO 49)
DIVMTQSPASLSVTPGEKVTITCKSSQSLLNSGNQKNYLTWYQQKPGQPPKLLIYWASTRESGVPDRF
TGSGSGTDFTLTISSLQAEDVAVYYCQNDYSYPLTFGQGTKLEIK

Anti-PD-L2 Light Chain VK3 (SEQ ID NO 50)
DIVMTQSPAFLSVTPGEKVTITCKSSQSLLNSGNQKNYLTWYQQKPGQPPKLLIYWASTRESGVPDRF
TGSGSGTDFTLTISSLQAEDVAVYYCQNDYSYPLTFGQGTKLEIK

Anti-PD-L2 Light Chain VK4 (SEQ ID NO 51)
DIVMTQSPAFLSVTPGEKVTITCKSSQSLLNSGNQKNYLTWYQQKPGQPPKLLIYWASTRESGVPDRF
SGSGSGTDFTLTISSLQAEDVAVYYCQNDYSYPLTFGQGTKLEIK

HUMAN ANTI-PD-1, PD-L1, AND PD-L2 ANTIBODIES AND USES THEREFOR

CROSS-REFERENCE TO RELATED APPLICATIONS

This application is a divisional of U.S. application Ser. No. 15/995,584, filed Jun. 1, 2018, now U.S. Pat. No. 10,370,448, issued Aug. 6, 2019, which is a divisional of U.S. application Ser. No. 14/822,651, filed Aug. 10, 2015, now U.S. Pat. No. 10,011,656, issued Jul. 3, 2018, which is a divisional of U.S. application Ser. No. 13/802,172, filed Mar. 13, 2013, now U.S. Pat. No. 9,102,727, issued Aug. 11, 2015, which is a continuation of U.S. application Ser. No. 13/120,406, internationally filed Sep. 25, 2009, now U.S. Pat. No. 8,552,154, issued Oct. 8, 2013, which is a National Phase application under 35 U.S.C. § 371 of International Application No. PCT/US2009/058475, filed Sep. 25, 2009, which claims priority to and the benefit of U.S. Provisional Application No. 61/100,534, filed Sep. 26, 2008, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677192000111SEQLIST.TXT, date recorded: Jul. 9, 2019, size: 71 KB).

BACKGROUND OF THE INVENTION

For T cells to respond to foreign polypeptides, at least two signals must be provided by antigen-presenting cells (APCs) to resting T lymphocytes (Jenkins, M. and Schwartz, R. (1987) J. Exp. Med. 165:302-319; Mueller, D. L. et al. (1990) J. Immunol. 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) Annu. Rev. Immunol. 14:233). Costimulation is neither antigen-specific, nor MHC-restricted, and is provided by distinct cell surface molecules expressed by APCs (Jenkins, M. K. et al. (1988) J. Immunol. 140:3324-3330; Linsley, P. S. et al. (1991) J. Exp. Med 173:721-730; Gimmi, C. D. et al. (1991) Proc. Natl. Acad Sci. USA 88:6575-6579; Young, J. W. et al. (1992) J. Clin. Invest. 90:229-237; Koulova, L. et al. (1991) J. Exp. Med. 173:759-762; Reiser, H. et al. (1992) Proc. Natl. Acad Sci. USA 89:271-275; van-Seventer, G. A. et al. (1990) J. Immunol. 144:4579-4586; LaSalle, J. M. et al. (1991) J. Immunol. 147:774-80; Dustin, M. I. et al. (1989) J. Exp. Med. 169:503; Armitage, R. J. et al. (1992) Nature 357:80-82; Liu, Y. et al. (1992) J. Exp. Med 175:437-445).

The proteins B7-1 (CD80) and B7-2 (CD86) are critical costimulatory molecules (Freeman et al. (1991) J. Exp. Med. 174:625; Freeman et al. (1989) J. Immunol. 143:2714; Azuma et al. (1993) Nature 366:76; Freeman et al. (1993) Science 262:909). B7-2 plays a predominant role during primary immune responses, while B7-1, which is upregulated later during an immune response, may be important for prolonging primary T cell responses or costimulating secondary T cell responses (Bluestone (1995) Immunity 2:555).

CD28 is a ligand for both B7-1 and B7-2 that is constitutively expressed by resting T cells and increases in expression following T cell activation. Ligation of CD28 in conjunction with a TCR signal results in transduction of a costimulatory signal that induces T cells to proliferate and secrete IL-2 (Linsley, P. S. et al. (1991) J. Exp. Med. 173:721-730; Gimmi, C. D. et al. (1991) Proc. Natl. Acad. Sci. USA 88:6575-6579; June, C. H. et al. (1990) Immunol. Today 11:211-6; Harding, F. A. et al. (1992) Nature 356: 607-609). A second B7-1 and B7-2 ligand, CTLA4 (CD152), is homologous to CD28 but not expressed by resting T cells. CTLA4 expression occurs following T cell activation (Brunet, J. F. et al. (1987) Nature 328:267-270). Ligation of CTLA4 results in transduction of an inhibitory signal that prevents T cell proliferation and cytokine secretion. Thus, CTLA4 is a critical negative regulator of T cell responses (Waterhouse et al. (1995) Science 270:985) (Allison and Krummel (1995) Science 270:932). The third member of the CD28 family to be discovered is ICOS (Hutloff et al. (1999) Nature 397:263; WO 98/38216). Ligation of ICOS by its ligand (ICOS-L) results in high levels of cytokine expression, but limited T cell expansion (Riley J. L. et al. (2001) J. Immunol. 166:4943-48; Aicher A. et al. (2000) J. Immunol. 164:4689-96; Mages H. W. et al. (2000) Eur. J Immunol. 30:1040-7; Brodie D. et al. (2000) Curr. Biol. 10:333-6; Ling V. et al. (2000) J. Immunol. 164:1653-7; Yoshinaga S. K. et al. (1999) Nature 402:827-32). If T cells are stimulated through the T cell receptor in the absence of a costimulatory signal, they become nonresponsive, anergic, or die.

The importance of the B7:CD28/CTLA4/ICOS costimulatory pathway has been demonstrated in vitro and in several in vivo model systems. Blockade of this costimulatory pathway results in the development of antigen specific tolerance in murine and human systems (Harding, F. A. et al. (1992) Nature 356:607 609; Lenschow, D. J. et al. (1992) Science 257:789 792; Turka, L. A. et al. (1992) Proc. Natl. Acad. Sci. USA 89:11102 11105; Gimmi, C. D. et al. (1993) Proc. Natl. Acad. Sci. USA 90:6586 6590; Boussiotis, V. et al. (1993) J. Exp. Med. 178:1753 1763). Conversely, expression of B7 by B7-negative murine tumor cells induces T-cell mediated specific immunity accompanied by tumor rejection and long lasting protection to tumor challenge (Chen, L. et al. (1992) Cell 71:1093 1102; Townsend, S. E. and Allison, J. P. (1993) Science 259:368 370; Baskar, S. et al. (1993) Proc. Natl. Acad. Sci. 90:5687 5690.). Therefore, manipulation of the costimulatory pathways offers great potential to stimulate or suppress immune responses in humans.

The discovery of more members of the B7-1 and CD28 families has revealed additional pathways that provide costimulatory and inhibitory second signals to T cells. One of the newer pathways is represented by the programmed death 1 (PD-1; also known as CD279) receptor and its ligands, PD-L1 (B7-H1; CD274) and PD-L2 (B7-DC; CD273). PD-1 is a member of the CD28/CTLA4 family that is expressed on activated, but not resting T cells (Nishimura et al. (1996) Int. Immunol. 8:773). Ligation of PD-1 by its ligands mediates an inhibitory signal that results in reduced cytokine production, and reduced T cell survival (Nishimura et al. (1999) Immunity 11:141; Nishimura et al. (2001) Science 291:319; Chemnitz et al. (2004) J. Immunol. 173: 945).

PD-L1 is a B7 family member that is expressed on many cell types, including APCs and activated T cells (Yamazaki et al. (2002) J. Immunol. 169:5538). PD-L1 binds to both PD-1 and B7-1. Both binding of T-cell-expressed B7-1 by PD-L1 and binding of T-cell-expressed PD-L1 by B7-1 result in T cell inhibition (Butte et al. (2007) Immunity 27:111). There is also evidence that, like other B7 family members, PD-L1 can also provide costimulatory signals to T cells (Subudhi et al. (2004) J. Clin. Invest. 113:694; Tamura et al. (2001) Blood 97:1809).

PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The structure and expression of PD-1, PD-L1, and PD-L2, as well as signaling characteristics and functions of these molecules in the context of regulating T cell activation and tolerance (e.g., therapeutic effects) are reviewed in greater detail in Kier et al. (2008) Ann. Rev. Immunol. 26:677, which is herein incorporated by reference in its entirety. Manipulation of this and other costimulatory pathways offers great potential to stimulate or suppress immune responses in humans and a need exists for compositions and methods useful for effecting such manipulations.

SUMMARY OF THE INVENTION

The present invention is based on the generation and isolation of novel composite, human monoclonal antibodies which specifically bind to human PD-1, human PD-L1, and human PD-L2, as well as the characterization of such novel antibodies and the demonstration of their therapeutic value in treating a variety of conditions mediated by PD-1, PD-L1, and/or PD-L2. Common techniques used to humanize murine antibodies frequently produce humanized antibodies that have reduced antigen binding affinities compared to the original murine antibodies (Almagro and Fransson (2008) Frontiers in Bioscience 13:1619-1633; Foote and Winter (1992) J. Mol. Biol. 224:487-499; Hwang et al. (2005) Methods 36: 35-42). Surprisingly, the composite, human antibodies of the present invention have been shown to bind to PD-1, PD-L1 or PD-L2 with affinities closely approximating those of the murine antibodies. Furthermore, conventional humanization techniques produce humanized antibodies that retain some murine sequence. As a result, such antibodies can retain immunogenicity when administered to humans. For example, the humanized antibody CAMPATH® elicits immunogenicity in about 50% of patients. The composite, human antibodies of the present invention, on the other hand, are completely derived from sequences of human origin. Therefore, they are likely to be significantly less immunogenic and more therapeutically effective and useful when administered to human patients than other anti-human PD-1, PD-L1, and/or PD-L2 antibodies. Accordingly, the composite, human antibodies of the present invention provide an improved means for treating and preventing disorders mediated by PD-1, PD-L1, and/or PD-L2, attributable in part to their unique specificity, affinity, structure, functional activity and the fact that they are derived from human antibody sequences. The present invention is also based on the discovery of new therapeutic applications, including treatment of persistent infectious diseases, asthma, inflammatory diseases, and cancers, by administering the composite, human antibodies described herein.

One embodiment of the invention is an isolated antibody, or an antigen-binding fragment thereof, that binds to a PD-1 protein, a PD-L1 protein, or a PD-L2 protein (such as human PD-1, PD-L1, or PD-L2 protein), wherein the isolated antibody, or antigen-binding fragment thereof, is chimeric, humanized, composite, human or human, and comprising one, two, three, four, five, or six CDR sequences selected from the group consisting of SEQ ID NO: 7-24.

The invention also provides an isolated antibody, or an antigen-binding fragment thereof, that binds to a PD-1 protein (such as a PD-1 protein comprising the amino acid sequence of SEQ ID NO:2), wherein the isolated antibody, or antigen-binding fragment thereof, is chimeric, humanized, composite, human or human, and comprising a heavy chain variable region sequence comprising SEQ ID NOs:7-9 (CDR1 sequence of SEQ ID NO:7, CDR2 sequence of SEQ ID NO:8, and CDR3 sequence of SEQ ID NO:9) and/or a light chain variable region sequence comprising SEQ ID NO:10-12 (CDR1 sequence of SEQ ID NO:10, CDR2 sequence of SEQ ID NO:11, and CDR3 sequence of SEQ ID NO:12).

The invention also provides an isolated antibody, or an antigen-binding fragment thereof, that binds to a PD-L1 protein (such as a PD-L1 protein comprising the amino acid sequence of SEQ ID NO:4), wherein the isolated antibody, or antigen-binding fragment thereof, is chimeric, humanized, composite, human or human, and comprising a heavy chain variable region sequence comprising SEQ ID NOs: 13-15 (CDR1 sequence of SEQ ID NO:13, CDR2 sequence of SEQ ID NO:14, and CDR3 sequence of SEQ ID NO:15), and/or a light chain variable region sequence comprising SEQ ID NO:16-18 (CDR1 sequence of SEQ ID NO:16, CDR2 sequence of SEQ ID NO:17, and CDR3 sequence of SEQ ID NO:18).

The invention also provides an isolated antibody, or an antigen-binding fragment thereof, that binds to a PD-L2 protein (such as a PD-L2 protein comprising the amino acid sequence of SEQ ID NO:6), wherein the isolated antibody, or antigen-binding fragment thereof, is chimeric, humanized, composite, human or human, and comprising a heavy chain variable region sequence comprising SEQ ID NOs: 19-21 (CDR1 sequence of SEQ ID NO:19, CDR2 sequence of SEQ ID NO:20, and CDR3 sequence of SEQ ID NO:21), and/or a light chain variable region sequence comprising SEQ ID NO:22-24 (CDR1 sequence of SEQ ID NO:22, CDR2 sequence of SEQ ID NO:23, and CDR3 sequence of SEQ ID NO:24).

The invention also includes an isolated antibody, or an antigen-binding fragment thereof, that binds to a PD-1 protein, a PD-L1 protein, or a PD-L2 protein (such as human PD-1, PD-L1, or PD-L2 protein) wherein the isolated antibody, or antigen-binding fragment thereof, is chimeric, humanized, composite, and/or human, and comprising a heavy chain sequence selected from the group consisting of SEQ ID NO: 25-29, 34-38, or 43-47 or a sequence with at least about 95%, 96%, 97%, 98%, 99%, 99.5%, 99.9% or more identical homology to SEQ ID NO: 25-29, 34-38, or 43-47, and/or a light chain sequence selected from the group consisting of SEQ ID NO: 30-33, 39-42, or 48-51, or a sequence with at least about 95%, 96%, 97%, 98%, 99%, 99.5%, 99.9% or more homology to SEQ ID NO: 30-33, 39-42, or 48-51.

The invention also provides an isolated antibody, or an antigen-binding fragment thereof, that binds to a PD-1 protein comprising the amino acid sequence of SEQ ID NO:2, wherein the isolated antibody, or antigen-binding fragment thereof, is chimeric, humanized, composite, or human, and comprising a heavy chain sequence selected from the group consisting of SEQ ID NO: 25-29, or a sequence with at least about 95%, 96%, 97%, 98%, 99%, 99.5%, 99.9% or more identical or homology to SEQ ID NO: 25-29, and/or a light chain sequence selected from the group consisting of SEQ ID NO: 30-33, or a sequence with at least about 95%, 96%, 97%, 98%, 99%, 99.5%, 99.9% or more identical or homology to SEQ ID NO: 30-33. For example, the antibody or antigen binding fragment thereof comprises a heavy chain variable region sequence of SEQ ID NO: 27 or 28, and a light chain variable region sequence of SEQ ID NOs: 32 or 33. In some embodiments, the antibody or antigen binding fragment thereof comprises a heavy chain variable region sequence of SEQ ID NO: 28, and a light chain variable region sequence of SEQ ID NOs: 32.

The invention also provides an isolated antibody, or an antigen-binding fragment thereof, that binds to a PD-L1 protein comprising the amino acid sequence of SEQ ID NO:4, wherein the isolated antibody, or antigen-binding fragment thereof, is chimeric, humanized, composite, or human, and comprising a heavy chain sequence selected from the group consisting of SEQ ID NO: 34-38, or a sequence with at least about 95%, 96%, 97%, 98%, 99%, 99.5%, 99.9% or more identical or homology to SEQ ID NO: 34-38, and/or a light chain sequence selected from the group consisting of SEQ ID NO: 39-42, or a sequence with at least about 95%, 96%, 97%, 98%, 99%, 99.5%, 99.9% or more identical or homology to SEQ ID NO: 39-42. For example, the antibody or antigen binding fragment thereof comprises a heavy chain variable region sequence of SEQ ID NO: 35 or 37, and a light chain variable region sequence of SEQ ID NO: 39, 40 or 42. In some embodiments, the antibody or antigen binding fragment thereof comprises a heavy chain variable region sequence of SEQ ID NO: 35, and a light chain variable region sequence of SEQ ID NO: 42.

The invention also provides an isolated antibody, or an antigen-binding fragment thereof, that binds to a PD-L2 protein comprising the amino acid sequence of SEQ ID NO:6, wherein the isolated antibody, or antigen-binding fragment thereof, is chimeric, humanized, composite, or human, and comprising a heavy chain sequence selected from the group consisting of SEQ ID NO: 43-47, or a sequence with at least about 95%, 96%, 97%, 98%, 99%, 99.5%, 99.9% or more identical or homology to SEQ ID NO: 43-47, and/or a light chain sequence selected from the group consisting of SEQ ID NO: 48-51, or a sequence with at least about 95%, 96%, 97%, 98%, 99%, 99.5%, 99.9% or more identical or homology to SEQ ID NO: 48-51. For example, the antibody or antigen binding fragment thereof comprises a heavy chain variable region sequence of SEQ ID NO: 44 or 46, and a light chain variable region sequence of SEQ ID NO: 49, 50 or 51. In some embodiments, the antibody or antigen binding fragment thereof comprises a heavy chain variable region sequence of SEQ ID NO: 46, and a light chain variable region sequence of SEQ ID NO: 51.

Another embodiment of the invention is an isolated antibody described herein, or an antigen-binding fragment thereof, that binds to a PD-1 protein, wherein the isolated antibody inhibits the binding of biotinylated EH12.2H7 antibody to Fc-PD-1 in a competition ELISA assay. Another embodiment is an isolated antibody described herein, or an antigen-binding fragment thereof, that binds to a PD-L1 protein, wherein the isolated antibody inhibits the binding of biotinylated 29E2A3 antibody to Fc-PD-L1 in a competition ELISA assay. Another embodiment is an isolated antibody described herein, or an antigen-binding fragment thereof, that binds to a PD-L2 protein, wherein the isolated antibody inhibits the binding of biotinylated 24F.10C12 antibody to Fc-PD-L2 in a competition ELISA assay.

Another embodiment of the invention is an isolated antibody described herein, or an antigen-binding fragment thereof, that binds to a PD-1 protein, wherein the isolated antibody inhibits a PD-1-mediated signal. Another embodiment is an isolated antibody described herein, or an antigen-binding fragment thereof, that binds to a PD-L1 protein wherein the isolated antibody inhibits a PD-L1-mediated signal. Another embodiment is an isolated antibody described herein, or an antigen-binding fragment thereof, that binds to a PD-L2 protein wherein the isolated antibody inhibits a PD-L2-mediated signal.

In particular, an embodiment of the invention is an isolated nucleic acid encoding a polypeptide, wherein the polypeptide comprises a sequence selected from the group consisting of SEQ ID NO: 25-51, or a sequence with at least about 80%, 85%, 90%, 91%, 92%, 93%, 94%, 95%, 96%, 97%, 98%, 99% or more identical or homology to SEQ ID NO: 25-51. Another embodiment is a vector, host cell or animal comprising one or more of these nucleic acids. Another aspect is a nucleic acid that hybridizes, under stringent conditions, with the complement of a nucleic acid encoding a polypeptide selected from the group consisting of SEQ ID NO: 25-51, or a sequence with at least about at least about 80%, 85%, 90%, 91%, 92%, 93%, 94%, 95%, 96%, 97%, 98%, 99% or more identical homology to SEQ ID NO: 25-51.

The invention also provides an isolated nucleic acid encoding a heavy chain variable region and/or a light chain variable region of any of the antibodies or antigen binding-fragments thereof described herein. In some embodiments, the nucleic acid is in a vector, such as an expression vector. The invention also provides a host cell comprising one or more nucleic acids encoding the heavy and/or light chain of the antibodies or antigen-binding fragments described herein. In some embodiments, the host cell produces the antibodies or antigen-binding fragments. The invention also provides methods of producing the antibody or antigen-binding fragment described herein, comprising culturing a cell that produces the antibody or antigen-binding fragment, and recovering the antibody or antigen-binding fragment from the cell culture.

The invention further includes a pharmaceutical composition, comprising an isolated antibody described herein, or an antigen-binding fragment thereof, and a pharmaceutically-acceptable carrier.

The invention encompasses a method of reactivating an exhausted T cell, comprising contacting a population of T cells wherein at least some cells express PD-, PD-L1 and/or PD-L2 using an antibody described herein or an antigen-binding fragment thereof either in vitro, ex vivo, or in vivo.

The invention further pertains to a method of treating a subject suffering from a persistent infection, including a viral infection, a bacterial infection, a helminth infection, or a protozoan infection, comprising administering to the subject a composition comprising an effective amount of an isolated antibody described herein, or an antigen-binding fragment thereof.

The invention further encompasses a method of treating cancer, comprising administering to the subject a composition comprising an effective amount of an isolated antibody described herein, or an antigen-binding fragment thereof, including wherein the isolated antibody induces antibody-mediated cytotoxicity or is modified to induce antibody-mediated cytotoxicity or conjugated to an agent selected from the group consisting of a toxin and an imaging agent. In some embodiments, the antibody or the antigen-binding fragment that binds to a PD-L1 is administered to the subject having a cancer over-expressing PD-L1. In some embodiments, the antibody or the antigen-binding fragment that binds to a PD-L2 is administered to the subject having a cancer over-expressing PD-L2.

The invention further pertains to a method of treating a subject suffering from asthma, comprising administering to the subject a composition comprising an effective amount of an isolated antibody that binds to a PD-L2 protein described herein, or an antigen-binding fragment thereof.

The invention also encompasses a method of treating a subject suffering from an inflammatory disease or transplant rejection, comprising administering to the subject a composition comprising an effective amount of an isolated antibody described herein, or an antigen-binding fragment thereof, that binds to a PD-L1 protein or a PD-L2 protein.

The invention also encompasses an antibody, an antigen-binding fragment or a polypeptide described herein for use in any of the methods described herein. The invention also encompasses the use of an antibody, an antigen-binding fragment or a polypeptide described herein for the manufacture of a medicament, such as a medicament for treating any of the diseases described herein in a subject.

BRIEF DESCRIPTION OF THE DRAWINGS

FIG. 1 shows a schematic diagram of expression vectors used for cloning the assembled human immunoglobulin sequences of the present invention.

FIGS. 2A-2E show composite, human heavy chain (FIG. 2A, VH1; FIG. 2B, VH2; FIG. 2C, VH3; and FIG. 2D, VH4; FIG. 2E, VH5) variable region sequences designed to correspond to that of the mouse anti-human PD-1 antibody, EH12.2H7.

FIGS. 3A-3D show composite, human light chain (FIG. 3A, Vκ1; FIG. 3B, Vκ2; FIG. 3C, Vκ3; FIG. 3D, Vκ4) variable region sequences designed to correspond to that of the mouse anti-human PD-1 antibody, EH12.2H7.

FIGS. 4A-4E show composite, human heavy chain (FIG. 4A, VH1; FIG. 4B, VH2; FIG. 4C, VH3; FIG. 4D, VH4; FIG. 4E, VH5) variable region sequences designed to correspond to that of the mouse anti-human PD-L1 antibody, 29E.2A3.

FIGS. 5A-5D show composite, human light chain (FIG. 5A, Vκ1; FIG. 5B, Vκ2; FIG. 5C, Vκ3; FIG. 5D, Vκ4) variable region sequences designed to correspond to that of the mouse anti-human PD-L1 antibody, 29E.2A3.

FIGS. 6A-6E show composite, human heavy chain (FIG. 6A, VH1; FIG. 6B, VH2; FIG. 6C, VH3; FIG. 6D, VH4; FIG. 6E, VH5) variable region sequences designed to correspond to that of the mouse anti-human PD-L2 antibody, 24F.10C12.

FIGS. 7A-7D show composite, human light chain (FIG. 7A, Vκ1; FIG. 7B, Vκ2; FIG. 7C, Vκ3; FIG. 7D, Vκ4) variable region sequences designed to correspond to that of the mouse anti-human PD-L2 antibody, 24F.10C12.

FIGS. 8A-8C show SDS-PAGE results of 1 μg of composite, human antibodies corresponding to the mouse anti-human antibodies, EH12.2H7 (FIG. 8A), 29E.2A3 (FIG. 8B), and 24F.10C12 (FIG. 8C), respectively.

FIGS. 9A-9C show ELISA competition results of human antibodies corresponding to and relative to the mouse anti-human antibodies, EH12.2H7, 29E.2A3, and 24F.10C12, respectively. In FIG. 9A, the binding of the purified antibodies to human PD-1 was tested via competition ELISA. Varying concentrations of each antibody (0.06 μg/ml to 8 μg/ml) were mixed with a fixed concentration of biotinylated EH12.2H7 (40 ng/ml) and bound to a PD-1 coated immulon maxisorb plate. Binding was detected via streptavidin-HRP and OPD substrate. Absorbance at 490 nm was measured on a plate reader and this was plotted against the test antibody concentration. In FIG. 9B, the binding of the purified antibodies to human PD-L1 was tested via competition ELISA. Varying concentrations of each antibody (0.02 μg/ml to 8 μg/ml) were mixed with a fixed concentration of biotinylated 29E.2A3 (40 ng/ml) and bound to a PD-L1 coated immulon maxisorb plate. Binding was detected via streptavidin-HRP and OPD substrate. Absorbance at 490 nm was measured on a plate reader and this was plotted against the test antibody concentration. In FIG. 9C, the binding of the purified antibodies to human PD-L2 was tested via competition ELISA. Varying concentrations of each antibody (0.02 μg/ml to 8 μg/ml) were mixed with a fixed concentration of biotinylated 24F.10C12 (40 ng/ml) and bound to a PD-L2 coated immulon maxisorb plate. Binding was detected via streptavidin-HRP and OPD substrate. Absorbance at 490 nm was measured on a plate reader and this was plotted against the test antibody concentration.

FIGS. 10A-10C show $IC_{50}$ binding data resulting from ELISA competition analysis of composite, human antibodies formed according to different combinations of composite, human heavy and light chains designed to correspond to those of the mouse anti-human antibodies, EH12.2H7 (FIG. 10A), 29E.2A3 (FIG. 10B), and 24F.10C12 (FIG. 10C), respectively. The assay was performed as described in FIG. 3. The $IC_{50}$ for each combination of heavy and light chain was normalized against the $IC_{50}$ of the mouse antibody. ND=No Data.

FIG. 11 shows the amino acid sequences of PD-1, PD-L1 and PD-L2.

FIG. 12 shows the amino acid sequences of the CDR regions of some of the Composite, Human Antibodies described herein.

FIG. 13 shows the amino acid sequences of the variable regions of some of the Composite, Human Antibodies described herein.

DETAILED DESCRIPTION OF THE INVENTION

Figure 14A:
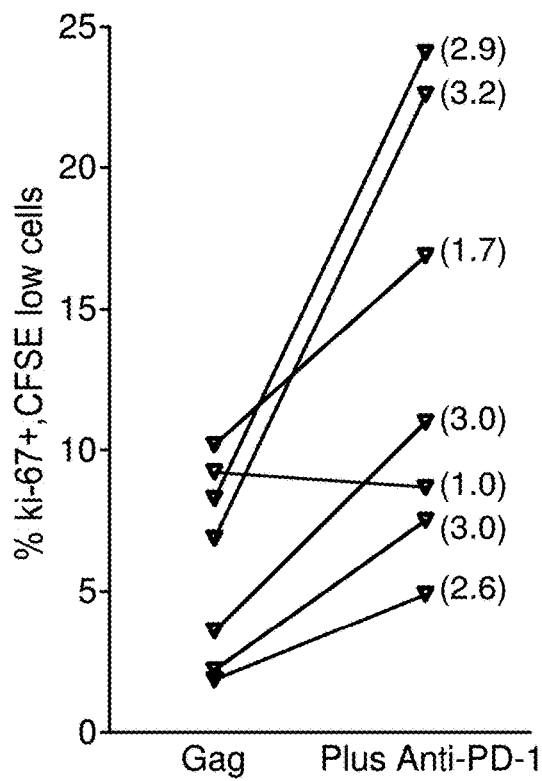
FIGS. 14A and 14B show effect of a humanized anti-PD-1 antibody (FIG. 14A) and a humanized anti-PD-L1 antibody (FIG. 14B) on the proliferative capacity of SIV Gag-specific CD8 T cells in vitro. Each symbol represents an individual macaque. Numbers in parenthesis represent fold increase in proliferation in the presence of a blocking Ab compared to no blocking Ab.

The present invention provides novel antibody-based therapeutics for treating and diagnosing a variety of disorders mediated by PD-1, PD-L1, and/or PD-L2 (e.g., treatment of persistent infectious diseases, asthma, inflammatory diseases, transplant rejections and cancers).

In order that the present invention may be more readily understood, certain terms are first defined. Additional definitions are set forth throughout the detailed description.

As used herein, the terms "PD-1", "PD-L1", and "PD-L2" include any variants or isoforms which are naturally expressed by cells, and/or fragments thereof having at least one biological activity of the full-length polypeptide, unless otherwise expressly defined. In addition, the term "PD-1 ligand" includes either or both PD-L1 (Freeman et al. (2000) *J. Exp. Med.* 192:1027) and PD-L2 (Latchman et al. (2001) *Nat. Immunol.* 2:261) and any variants or isoforms which are naturally expressed by cells, and/or fragments thereof having at least one biological activity of the full-length polypeptides. For example, PD-1, PD-L1, and PD-L2 sequences from different species, including humans, are well known in the art (see, for example, herein incorporated in their entirety by reference, Honjo et al., U.S. Pat. No. 5,629,204, which discloses human and mouse PD-1 sequences; Wood et al., U.S. Pat. No. 7,105,328, which discloses human PD-1 sequences; Chen et al., U.S. Pat. No. 6,803,192, which discloses human and mouse PD-L1 sequences; Wood et al., U.S. Pat. No. 7,105,328, which discloses human PD-L1 sequences; Freeman et al., US Pat. Pub. 20020164600, which discloses human and mouse PD-L2 sequences).

As used herein, the term "antibody" includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Leski. *J. Mol. Biol.* 196:901-917 (1987)). The end of the Chothia CDR-H1 loop when numbered using the Kabat numbering convention varies between H32 and H34 (see below) depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32, 33 or 34 | H30-H35B (Kabat Numbering) |
| H1 | H31-H35 | H26-H35 | H26-H32 | H30-H35 (Chothia Numbering) |
| H2 | H50-H65 | H50-H58 | H52-H56 | H47-H58 |
| H3 | H95-H102 | H95-H102 | H95-H102 | H93-H101 |

Hypervariable regions may comprise "extended hypervariable regions" as follows: 24-36 or 24-34 (L1), 46-56 or 50-56 (L2) and 89-97 (L3) in the VL and 26-35B (H1), 50-65, 47-65 or 49-65 (H2) and 93-102, 94-102 or 95-102 (H3) in the VH. These extended hypervariable regions are typically combinations of the Kabat and Chothia definitions, which may optionally further include residues identified using the Contact definition. The variable domain residues are numbered according to Kabat et al., supra for each of these definitions.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," 5$^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety).

As used herein, the term "antigen-binding portion" of an antibody (or simply "antibody portion"), refers to one or more fragments of an antibody that retain the ability to specifically bind to an antigen (e.g., PD-1, PD-L1, and/or PD-L2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, CL and CH1 domains; (ii) a F(ab')2 fragment, a bivalent fragment comprising two Fab fragments linked by a disulfide bridge at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to PD-1, PD-L1, or PD-L2 polypeptides. The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term an "isolated antibody" is intended to refer to an antibody which is substantially free of other antibodies having different antigenic specificities (e.g., an isolated antibody that specifically binds to PD-1, PD-L1, or PD-L2 is substantially free of antibodies that do not bind to PD-1, PD-L1, or PD-L2, respectively). An isolated antibody that specifically binds to an epitope of PD-1, PD-L1, and/or PD-L2 may, however, have cross-reactivity to other PD-1, PD-L1, and/or PD-L2 proteins, respectively, from different species. However, the antibody preferably always binds to human PD-1, PD-L1, and/or PD-L2. In addition, an isolated antibody is typically substantially free of other cellular material and/or chemicals. In one embodiment of the invention, a combination of "isolated" monoclonal antibodies having different specificities to PD-1, PD-L1, and/or PD-L2 are combined in a well defined composition.

As used herein, the term "humanized antibody" refers to an antibody that consists of the CDR of antibodies derived from mammals other than human, and the FR region and the constant region of a human antibody. A humanized antibody is useful as an effective component in a therapeutic agent according to the present invention since antigenicity of the humanized antibody in human body is lowered.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in human body is lowered.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, the term "$K_D$" is intended to refer to the dissociation equilibrium constant of a particular antibody-antigen interaction.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant human PD-1, PD-L1, or PD-L2 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "isotype" refers to the antibody class (e.g., IgM or IgG1) that is encoded by heavy chain constant region genes.

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "unrearranged" or "germline configuration" in reference to a V segment refers to the configuration wherein the V segment is not recombined so as to be immediately adjacent to a D or J segment.

As used herein, the term "nucleic acid molecule" is intended to include DNA molecules and RNA molecules. A nucleic acid molecule may be single-stranded or double-stranded, but preferably is double-stranded DNA.

As used herein, the term "isolated nucleic acid molecule" in reference to nucleic acids encoding antibodies or antibody portions (e.g., $V_H$, $V_L$, CDR3) that bind to PD-1, PD-L1, or PD-L2, is intended to refer to a nucleic acid molecule in which the nucleotide sequences encoding the antibody or antibody portion are free of other nucleotide sequences encoding antibodies or antibody portions that bind antigens other than PD-1, PD-L1, or PD-L2, respectively, which other sequences may naturally flank the nucleic acid in human genomic DNA. FIGS. 2-7 correspond to the nucleotide and amino acid sequences comprising the heavy chain ($V_H$) and light chain ($V_L$) variable regions of the human anti-PD-1, PD-L1, or PD-L2 antibodies of the present invention, respectively.

The present invention also encompasses "conservative sequence modifications" of the sequences set forth in the figures (e.g., FIGS. 2-7), including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into the sequence set forth in the figures (e.g., FIGS. 2-7) by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-PD-1, anti-PD-L1, or anti-PD-L2 antibody is preferably replaced with another amino acid residue from the same side chain family.

Alternatively, in another embodiment, mutations can be introduced randomly along all or part of a human anti-PD-1, PD-L1, or PD-L2 antibody coding sequence, such as by saturation mutagenesis, and the resulting modified human anti-PD-1, anti-PD-L1, or anti-PD-L2 antibodies can be screened for binding activity.

Accordingly, antibodies encoded by the heavy and light chain variable region nucleotide sequences disclosed herein and/or containing the heavy and light chain variable region amino acid sequences disclosed herein (e.g., FIGS. 2-7) include substantially similar antibodies encoded by or containing similar sequences which have been conservatively modified. Further discussion as to how such substantially similar antibodies can be generated based on the sequences (i.e., heavy and light chain variable regions) disclosed herein (e.g., FIGS. 2-7) is provided below.

In addition, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |

-continued

| GENETIC CODE | |
|---|---|
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=#of identical positions/total #of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, the term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "subject" includes any human or non-human animal. For example, the methods and compositions of the present invention can be used to treat a subject with an inflammatory disease, such as arthritis, e.g., rheumatoid arthritis. The term "non-human animal" includes all vertebrates, e.g., mammals and non-mammals, such as non-human primates, sheep, dog, cow, chickens, amphibians, reptiles, etc.

As used herein, the term "modulate" includes up-regulation and down-regulation, e.g., enhancing or inhibiting a response.

As used herein, the term "inhibit" includes the decrease, limitation, or blockage, of, for example a particular action, function, or interaction.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term T cell also includes T helper 1 type T cells, T helper 2 type T cells, T helper 17 type T cells and inhibitory T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

As used herein, the term "costimulate," as used with reference to activated immune cells, includes the ability of a costimulatory polypeptide to provide a second, non-activating receptor mediated signal (a "costimulatory signal") that induces proliferation and/or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "inhibitory signal" refers to a signal transmitted via an inhibitory receptor (e.g., CTLA4 or PD-1) for a polypeptide on an immune cell. Such a signal antagonizes a signal via an activating receptor (e.g., via a TCR or CD3 polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, the term "activity," when used with respect to a polypeptide, e.g., PD-1, PD-L1, or PD-L2 polypeptide, includes activities which are inherent in the structure of the protein. For example, with regard to PD-1 ligand, the term "activity" includes the ability to modulate immune cell costimulation (e.g. by modulating a costimulatory signal in an activated immune cell) or to modulate inhibition by modulating an inhibitory signal in an immune cell (e.g., by engaging a natural receptor on an immune cell). Those of skill in the art will recognize that when a PD-1 ligand polypeptide binds to a costimulatory receptor, a costimulatory signal can be generated in the immune cell. When a PD-1 ligand polypeptide binds to an inhibitory receptor, an inhibitory signal is generated in the immune cell. Also, when a PD-1 ligand binds to a B7-1 polypeptide, an inhibitory signal can be generated (Butte et al. (2007) *Immunity* 27:111).

With respect to PD-1, the term "activity" includes the ability of a PD-1 polypeptide to modulate an inhibitory signal in an immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

As used herein, the term "interaction", when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding a ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

As used herein the singular forms "a", "an", and "the" include plural referents unless the context clearly dictates otherwise.

It is understood that aspects and embodiments of the invention described herein include "consisting" and/or "consisting essentially of" aspects and embodiments.

Various aspects of the invention are described in further detail in the following subsections.

I. Isolated Nucleic Acid Molecules

One aspect of the invention pertains to isolated nucleic acid molecules that encode polypeptides of the present invention (e.g., those in FIGS. 2-7) or biologically active portions thereof, as well as nucleic acid fragments sufficient for use as hybridization probes to identify nucleic acid molecules encoding these polypeptides and fragments for use as PCR primers for the amplification or mutation of the nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention (e.g., those in FIGS. 2-7), or a portion thereof, can be isolated using standard molecular biology techniques and the sequence information provided herein. For example, a nucleic acid molecule encompassing all or a portion of sequences shown in FIGS. 2-7 can be isolated by the polymerase chain reaction (PCR) using synthetic oligonucleotide primers designed based upon the sequences shown in FIGS. 2-7.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the invention can be prepared by standard synthetic techniques, e.g., using an automated DNA synthesizer.

In another embodiment, an isolated nucleic acid molecule of the invention comprises a nucleic acid molecule which is a complement of a nucleic acid molecule of the present invention (e.g., those in FIGS. 2-7), or a portion thereof. A nucleic acid molecule which is complementary to a nucleic acid molecule of the present invention (e.g., those in FIGS. 2-7), or a portion thereof, is one which is sufficiently complementary to the nucleotide sequence shown in FIGS. 2-7, such that it can hybridize to the respective nucleotide sequence shown in FIGS. 2-7, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence shown in FIGS. 2-7, or a portion of any of these nucleotide sequences.

Moreover, the nucleic acid molecule of the invention can comprise only a portion of a nucleic acid molecule of the present invention (e.g., those in FIGS. 2-7), or a portion thereof, for example, a fragment which can be used as a probe or primer or a fragment which encodes a portion of a polypeptide of the invention, e.g., those in FIGS. 2-7. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a nucleic acid molecule of the present invention (e.g., those in FIGS. 2-7); of an anti-sense sequence of a nucleic acid molecule of the present invention (e.g., those in FIGS. 2-7); or of a mutant of a nucleic acid molecule of the present invention (e.g., those in FIGS. 2-7).

Probes based on a nucleic acid molecule of the present invention (e.g., those in FIGS. 2-7) can be used to detect transcripts or genomic sequences encoding the same or homologous polypeptides. In one embodiment, the probe further comprises a label group attached thereto, e.g., the label group can be a radioisotope, a fluorescent compound, an enzyme, or an enzyme co-factor.

A nucleic acid fragment encoding a "biologically active portion of a polypeptide of the invention" can be prepared by isolating a portion of the nucleotide sequence of a nucleic acid molecule of the present invention (e.g., those in FIGS. 2-7) which encodes a polypeptide having a biological activity of a polypeptide of the invention (e.g., the ability to bind to its antigenic target), expressing the encoded portion of the polypeptide of the invention (e.g., by recombinant expression in vitro) and assessing the activity of the encoded portion of the polypeptide of the invention.

The invention further encompasses nucleic acid molecules that differ from nucleotide sequence(s) shown in FIGS. 2-7 due to degeneracy of the genetic code and thus encode the same polypeptides as those encoded by the respective nucleotide sequence shown in FIGS. 2-7. In another embodiment, an isolated nucleic acid molecule of the invention has a nucleotide sequence encoding a polypeptide of the present invention (e.g., those in FIGS. 2-7).

Nucleic acid molecules corresponding to homologues of a nucleic acid molecule of the present invention (e.g., those in FIGS. 2-7) can be isolated based on their homology to the nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising a nucleic acid molecule of the present invention (e.g., those in FIGS. 2-7).

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further non-limiting example of stringent hybridization conditions includes hybridization at 6×SSC at 45° C., followed by one or more washes in 0.2×SSC, 0.1% SDS at 65° C. A non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(#of A+T bases)+4(#of G+C bases). For hybrids between 18 and 49 base pairs in length, $T_m$ (° C.)=81.5+16.6($\log_{10}$ [$Na^+$])+0.41(% G+C)−(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) Proc. Natl. Acad. Sci. USA 81:1991-1995 (or alternatively 0.2×SSC, 1% SDS).

The skilled artisan will further appreciate that changes can be introduced by mutation into a nucleic acid molecule of the present invention (e.g., those in FIGS. 2-7), thereby leading to changes in the amino acid sequence of the encoded polypeptides of the present invention, without altering the functional ability of the polypeptides. For example, nucleotide substitutions leading to amino acid substitutions at "non-essential" amino acid residues can be made in a nucleic acid molecule of the present invention (e.g., those in FIGS. 2-7). A "non-essential" amino acid residue is a residue that can be altered from a nucleic acid molecule of the present invention (e.g., those in FIGS. 2-7) without altering the biological activity, whereas an "essential" amino acid residue is required for biological activity. For example, amino acid residues that are conserved among the polypeptides of the present invention, e.g., those required for binding of the polypeptides to its target antigen, are predicted to be particularly unamenable to alteration.

Accordingly, another aspect of the invention pertains to nucleic acid molecules encoding polypeptides of the present invention (e.g., those in FIGS. 2-7) that contain changes in amino acid residues that are not essential for activity. Such polypeptides differ in amino acid sequence from those in FIGS. 2-7, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to those in FIGS. 2-7.

An isolated nucleic acid molecule encoding a polypeptide identical to the polypeptides of those in FIGS. 2-7 can be created by introducing one or more nucleotide substitutions, additions or deletions into the nucleotide sequence of those in FIGS. 2-7 such that one or more amino acid substitutions, additions or deletions are introduced into the encoded polypeptide. Mutations can be introduced into nucleic acid molecules of the present invention (e.g., those in FIGS. 2-7) by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the invention (e.g., those in FIGS. 2-7) can be replaced with another amino acid residue from the same side chain family. Alternatively, in another embodiment, mutations can be introduced randomly along all or part of a nucleic acid molecule(s) of the present invention (e.g., those in FIGS. 2-7), such as by saturation mutagenesis, and the resultant mutants can be screened for biological activity to identify mutants that retain activity. Following mutagenesis of a nucleic acid molecule of the present invention (e.g., those in FIGS. 2-7), the encoded polypeptide can be expressed recombinantly and the activity of the polypeptide can be determined.

In one embodiment, a mutant polypeptide of the invention can be assayed for the ability to bind to and/or modulate the activity of a natural PD-1 (e.g., PD-1 ligands) or PD-1 ligand partner (e.g., PD-1 and B7-1), modulate intra- or intercellular signaling, modulate activation of T lymphocytes, and/or modulate the immune response of an organism.

Yet another aspect of the invention pertains to isolated nucleic acid molecules encoding fusion proteins. Such nucleic acid molecules, comprising at least a first nucleotide sequence encoding a polypeptide of the invention (e.g., those in FIGS. 2-7) operatively linked to a second nucleotide sequence encoding a polypeptide of the invention (e.g., those in FIGS. 2-7) can be prepared by standard recombinant DNA techniques.

The expression characteristics of a nucleic acid molecules of the present invention (e.g., those in FIGS. 2-7) within a cell line or microorganism may be modified by inserting a heterologous DNA regulatory element into the genome of a stable cell line or cloned microorganism such that the inserted regulatory element is operatively linked with the a nucleic acid molecules of the present invention (e.g., those in FIGS. 2-7). For example, a heterologous regulatory element may be inserted into a stable cell line or cloned microorganism, such that it is operatively linked with a nucleic acid molecules of the present invention (e.g., those in FIGS. 2-7), using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated Polypeptide Molecules

One aspect of the invention pertains to isolated polypeptides of the present invention (including antibodies and antigen-binding fragments thereof described herein, and those in FIGS. 2-7), and biologically active portions thereof. In one embodiment, polypeptides of the present invention (e.g., those in FIGS. 2-7), and biologically active portions thereof can be isolated from cells or tissue sources by an appropriate purification scheme using standard protein purification techniques. In another embodiment, polypeptides of the present invention (e.g., those in FIGS. 2-7), and biologically active portions thereof are produced by recombinant DNA techniques. Alternatively, polypeptides of the present invention (e.g., those in FIGS. 2-7), and biologically active portions thereof can be chemically synthesized using standard peptide synthesis techniques.

An "isolated" or "purified" polypeptide or biologically active portion thereof is substantially free of cellular material or other contaminating proteins from the cell or tissue source from which the polypeptides of the present invention (e.g., those in FIGS. 2-7) is derived, or substantially free from chemical precursors or other chemicals when chemically synthesized. The language "substantially free of cellular material" includes preparations of polypeptide(s) of the present invention (e.g., those in FIGS. 2-7), and biologically active portions thereof, in which the polypeptide is separated from cellular components of the cells from which it is isolated or recombinantly produced. In one embodiment, the language "substantially free of cellular material" includes preparations of polypeptide(s) of the present invention (e.g., those in FIGS. 2-7), and biologically active portions thereof having less than about 30% (by dry weight) of proteins not of the present invention (also referred to herein as a "contaminating protein"), more preferably less than about 20% of proteins not of the present invention, still more preferably less than about 10% of proteins not of the present invention, and most preferably less than about 5% of proteins not of the present invention. When polypeptides of the present invention (e.g., those in FIGS. 2-7) or biologically active portion thereof are recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of polypeptide(s) of the present invention (e.g., those in FIGS. 2-7) or biologically active portion thereof in which the polypeptide is separated from chemical precursors or other chemicals which are involved in the synthesis of the polypeptide. In one embodiment, the language "substantially free of chemical precursors or other chemicals" includes preparations of polypeptide(s) of the present invention (e.g., those in FIGS. 2-7) or biologically active portion thereof having less than about 30% (by dry weight) of chemical precursors or of proteins not of the present invention, more preferably less than about 20% chemical precursors or of proteins not of the present invention, still more preferably less than about 10% chemical precursors or of proteins not of the present invention, and most preferably less than about 5% chemical precursors or of proteins not of the present invention.

As used herein, a "biologically active portion" of polypeptide(s) of the present invention (e.g., those in FIGS. 2-7) include polypeptides which participates in an interaction between PD-1 and a non-PD-1 molecule, PD-L1 and a non-PD-L1 molecule, or PD-L2 and a non-PD-L2 molecule, e.g., a natural ligand of PD-1, e.g., PD-1 ligands, or a natural ligand of PD-1 ligands, e.g., PD-1 or B7-1, respectively. Biologically active portions of a polypeptide(s) of the present invention (e.g., those in FIGS. 2-7) include peptides comprising amino acid sequences sufficiently identical to or derived from the amino acid sequence of polypeptide(s) of the present invention (e.g., those in FIGS. 2-7), which include fewer amino acids than the respective, full length polypeptide(s) of the present invention (e.g., those in FIGS. 2-7), and exhibit at least one activity of the respective polypeptide(s) of the present invention (e.g., those in FIGS. 2-7). In one embodiment, biologically active portions comprise a domain or motif with the ability to specifically bind PD-1 or a PD-L1 ligand according to the antigen, respectively, to which it was raised or designed to bind. Biologically active portions of polypeptide(s) of the present invention (e.g., those in FIGS. 2-7) can be used as targets for developing agents which modulate an activity mediated by PD-1, PD-L1, or PD-L2, e.g., immune cell activation or suppression.

In another embodiment, polypeptide(s) of the present invention (e.g., those in FIGS. 2-7) has an amino acid sequence shown in FIGS. 2-7. In other embodiments, the polypeptide is substantially identical to polypeptide(s) shown in FIGS. 2-7, and retains the functional activity of the respective polypeptide(s) shown in FIGS. 2-7, yet differs in amino acid sequence due to mutagenesis, as described in detail in subsection I above. Accordingly, in another embodiment, a polypeptide(s) of the present invention is a polypeptide which comprises an amino acid sequence at least about 71%, 75%, 80%, 85%, 90%, 91%, 92%, 93%, 94%, 95%, 96% 97%, 98%, 99%, 99.5%, or 99.9% or more identical to a polypeptide(s) shown in FIGS. 2-7.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the present invention (e.g., those in FIGS. 2-7) operatively linked to a polypeptide not of the present invention. A "polypeptide(s) of the present invention" refers to a polypeptide having an amino acid sequence corresponding to a polypeptide shown in FIGS. 2-7, whereas a "polypeptide not of the present invention" refers to a polypeptide not having an amino acid sequence corresponding to a polypeptide which is not substantially homologous to a polypeptide shown in FIGS. 2-7, e.g., a polypeptide which is different from a polypeptide shown in FIGS. 2-7 and which is derived from the same or a different organism. Within the fusion protein, the term "operatively linked" is intended to indicate that the polypeptide(s) of the present invention and the polypeptide(s) not of the present invention are fused in-frame to each other. The polypeptide(s) not of the present invention can be fused to the N-terminus or C-terminus of the polypeptide(s) of the present invention and corresponds to a moiety that alters the solubility, binding affinity, stability, or valency of the polypeptide(s) of the present invention.

For example, in one embodiment, the fusion protein is a GST fusion protein with a polypeptide(s) of the present invention. Such fusion proteins can facilitate the purification of recombinant polypeptides of the invention. In another embodiment, the fusion protein contains a heterologous signal sequence at its N-terminus. In certain host cells (e.g., mammalian host cells), expression and/or secretion of polypeptide(s) of the present invention can be increased through use of a heterologous signal sequence.

A chimeric or fusion polypeptide(s) of the present invention (e.g., those in FIGS. 2-7) can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety (e.g., a GST polypeptide).

The amino acid sequences of polypeptide(s) of the present invention (e.g., those in FIGS. 2-7) identified herein will enable those of skill in the art to produce polypeptides corresponding to polypeptide(s) of the present invention (e.g., those in FIGS. 2-7). Such polypeptides can be produced in prokaryotic or eukaryotic host cells by expression of polynucleotides encoding a polypeptide(s) of the present invention (e.g., those in FIGS. 2-7. Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference).

III. Antibodies to PD-1, PD-L1, and/or PD-L2

Antibodies to PD-1, PD-L1, or PD-L2 described herein may be produced using any methods described herein or known in the art. Monoclonal antibodies (e.g., human antibodies) of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

One method for generating hybridomas which produce monoclonal antibodies of the invention is the murine system. Hybridoma production in the mouse is well known in the art, including immunization protocols and techniques for isolating and fusing immunized splenocytes.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature 256:495-497) (see also Brown et al. (1981) J. Immunol. 127:539-46; Brown et al. (1980) J. Biol. Chem. 255:4980-83; Yeh et al. (1976) Proc. Natl. Acad. Sci. 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-PD-1, PD-L1, or PD-L2 monoclonal antibody (see, e.g., Galfre, G. et al. (1977) Nature 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/0-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PD-1, PD-L1, or PD-L2 antibodies, such as chimeric, composite, and humanized monoclonal antibodies, which can be made using standard recombinant DNA techniques, can be generated. Such chimeric, composite, and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125, 023; Better et al. (1988) *Science* 240:1041-1043; Liu et al. (1987) *Proc. Natl. Acad. Sci. USA* 84:3439-3443; Liu et al. (1987)*J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

In another embodiment, human monoclonal antibodies directed against PD-1, PD-L1, or PD-L2 can be generated using transgenic or transchromosomal mice carrying parts of the human immune system rather than the mouse system. In one embodiment, transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856 859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49 101; Lonberg, N. and Huszar, D. (1995) *Intern. Rev. Immunol.* Vol. 13: 65 93, and Harding, F. and Lonberg, N. (1995) *Ann. N. Y Acad. Sci* 764:536 546). The preparation of HuMAb mice is described in Taylor, L. et al. (1992) *Nucleic Acids Research* 20:6287 6295; Chen, J. et al. (1993) *International Immunology* 5: 647 656; Tuaillon et al. (1993) *Proc. Natl. Acad. Sci USA* 90:3720 3724; Choi et al. (1993) *Nature Genetics* 4:117 123; Chen, J. et al. (1993) *EMBO J.* 12: 821 830; Tuaillon et al. (1994) *J. Immunol.* 152:2912 2920; Lonberg et al., (1994) *Nature* 368(6474): 856 859; Lonberg, N. (1994) Handbook of Experimental Pharmacology 113:49 101; Taylor, L. et al. (1994) *International Immunology* 6: 579 591; Lonberg, N. and Huszar, D. (1995) *Intern. Rev. Immunol.* Vol. 13: 65 93; Harding, F. and Lonberg, N. (1995) *Ann. N.Y. Acad. Sci* 764:536 546; Fishwild, D. et al. (1996) *Nature Biotechnology* 14: 845 851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In another embodiment, an antibody for use in the invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229. Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-1, PD-L1, and/or a PD-L2 polypeptide. In one embodiment, the bispecific antibody could specifically bind to both a PD-1 ligand and a PD-1 polypeptide.

Yet another aspect of the invention pertains to anti-PD-1, PD-L1, or PD-L2 polypeptide antibodies that are obtainable by a process comprising, immunizing an animal with an immunogenic PD-1, PD-L1, or PD-L2 polypeptide, respectively, or an immunogenic portion thereof; and then isolating from the animal antibodies that specifically bind to the polypeptide.

In still another aspect of the invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse) (see, for example, the Examples section below).

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for this use are known in the art and include the plasmids provided in the Examples section below. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, the structural features of known, non-human or human antibodies (e.g., a mouse anti-human anti-PD-1, PD-L1, or PD-L2 antibody, such as antibodies EH12.2H7, 29E.2A3, and 24F.10C12 respectively) are used to create structurally related human anti-human PD-1, PD-L1, or PD-L2 antibodies that retain at least one functional property of the antibodies of the invention, such as binding to PD-1, PD-L1, or PD-L2. Another functional property includes inhibiting binding of EH12.2H7 to PD-1, 29E.2A3 to PD-L1, or 24F.10C12 to PD-L2 in a competition ELISA assay. In some embodiments, the structurally related anti-human PD-1, PD-L1, or PD-L2 antibodies have a lower binding affinity to the antigen as compared to antibody EH12.2H7, 29E.2A3, or 24F.10C12 as measured by the IC50 value as described in Example 2 (e.g., the affinity of the murine reference antibody is no greater than any of 3.0, 2.0, 1.9, 1.8, 1.7, 1.6, 1.5, 1.4, 1.3, 1.2 or 1.1 fold of the structurally related antibody).

In some embodiments, the structurally related anti-human PD-1, PD-L1, or PD-L2 antibodies have a higher affinity to the antigen as compared to antibody EH12.2H7, 29E.2A3, or 24F.10C12 as measured by the IC50 value as described in Example 2 (such as the affinity of the structurally related antibody is at least 1.1, 1.2, 1.3, 1.4, 1.5, 1.6, 1.7, 1.8, 1.9, or 2.0 fold of the reference antibody). In addition, one or more CDR or variable regions of the present invention (e.g., FIGS. 2-7) can be combined recombinantly with known human framework regions and CDRs to create additional, recombinantly-engineered, human anti-PD-1, PD-L1, or PD-L2 antibodies of the invention.

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of variable regions of the present invention (e.g., FIGS. 2-7). The antibodies further can comprise the CDR2s of variable regions of the present invention (e.g., FIGS. 2-7). The antibodies further can comprise the CDR1s of variable regions of the present invention (e.g., FIGS. 2-7). The antibodies can further comprise any combinations of the CDRs.

The CDR1, 2, and/or 3 regions of the engineered antibodies described above can comprise the exact amino acid sequence(s) as those of variable regions of the present invention (e.g., FIGS. 2-7) disclosed herein. However, the ordinarily skilled artisan will appreciate that some deviation from the exact CDR sequences may be possible while still retaining the ability of the antibody to bind PD-1, PD-L1, or PD-L2 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., FIGS. 2-7).

In addition to simply binding PD-1, PD-L1, or PD-L2, engineered antibodies such as those described above may be selected for their retention of other functional properties of antibodies of the invention, such as:

(1) binding to human PD-1, PD-L1, or PD-L2;
(2) inhibiting binding of EH12.2H7 to PD-1, 29E.2A3 to PD-L1, or 24F.10C12 to PD-L2;
(3) binding to human PD-1 and inhibiting the ability of the bound PD-1 to bind to PD-1 ligands (e.g., PD-L1 and/or PD-L2);
(4) binding to human PD-L1 and inhibiting the ability of the bound PD-L1 to bind to PD-L1 ligands (e.g., PD-1 and/or B7-1);
(5) binding to human PD-L2 and inhibiting the ability of the bound PD-L2 to bind to PD-L2 ligands (e.g., PD-1).

Heavy and light chain variable region amino acid sequences for antibody EH12.2H7, 29E.2A3 and 24F.10C12 are shown below.

EH12.2H7 heavy chain variable region
(SEQ ID NO: 76)
QVQLQQSGAELAKPGASVQMSCKASGYSFTSSWIHWVKQRPGQGLEWIG
IYPSTGFTEYNQKFKDKATLTADKSSSTAYMQLSSLTSEDSAVYYCARWR
DSSGYHAMDYWGQGTSVTVSS EH12.2H7 light chain variable region
(SEQ ID NO: 77)
DIVLTQSPASLTVSLGQRATISCRASQSVSTSGYSYMEIWYQQKPGQPPK
LLIKFGSNLESGIPARFSGSGSGTDFTLNIHPVEEEDTATYYCQHSWEIP
YTFGGGTKLEIK 29E.2A3 heavy chain variable region
(SEQ ID NO: 78)
EVQLQQSGPELVKPGASVKMSCKASGYTFTSYVMHWVKQKPGQGLEWIGY
VNPFNDGTKYNEMFKGKATLTSDKSSSTAYMELSSLTSEDSAVYYCARQA
WGYPWGQGTLVTVSA 29E.2A3 light chain variable region
(SEQ ID NO: 79)
DIVLTQSPASLAVSLGQRATISCRATESVEYYGTSLVQWYQQKPGQPPKL
LIYAASSVDSGVPARFSGSGSGTDFSLTIHPVEEDDIAMYFCQQSRRVPY
TFGGGTKLEIK 24F.10C12 heavy chain variable region
(SEQ ID NO: 80)
QVQLQQSAAELARPGASVKMSCKASGYTFTGYTMEIWVKQRPGQGLEWIG
YINPRSGYTEYNQKFKDKTTLTADKSSSTAYMQLSSLTSEDSAVYYCARP
WFAYWGQGTLVTVSA 24F.10C12 light chain variable region
(SEQ ID NO: 81)
DIVMTQSPSSLTVTAGEKVTMSCKSSQSLLNSGNQKNYLTWYQQKPGQPP
KLLIYWASTRESGVPDRFTGSGSGTDFTLTISSVQAEDLAVYYCQNDYSY
PLTFGAGTKLELK Antibodies' activity in inhibiting binding of PD-1, PD-L1, or PD-L2 to its ligand(s) can be determined by testing the ability of the antibody from blocking the binding between PD-1, PD-L1, or PD-L2 and its ligand. A competition ELISA assay in the presence of a labeled ligand and the antibody may be used. For example, to determine if an anti-PD-L1 antibody could block the interaction between PD-1 and PD-L1, a competitive binding experiment is performed. Cells expressing PD-L1 is preincubated with the anti-PD-L1 antibody followed by the addition of biotinylated PD-1-Ig fusion protein. If the anti-PD-L1 antibody blocks the binding of PD-1-Ig in a dose-dependent manner and with high avidity, the antib-PD-L1 antibody is considered as being effective in inhibiting the interaction between PD-1 and PD-L1. Similar tests may be carried out to test antibodies that are effective in inhibiting the interaction of PD-1 and PD-L2.

IV. Recombinant Expression Vectors and Host Cells

Another aspect of the invention pertains to vectors, preferably expression vectors, containing one, two, or more nucleic acid molecules encoding one or more polypeptides of the present invention (e.g., FIGS. 2-7) (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of polypeptides of the present invention (e.g., FIGS. 2-7) in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in E. coli with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion E. coli expression vectors include pTrc (Amann et al. (1988) Gene 69:301-315) and pET 1 Id (Studier et al. (1990) Methods Enzymol. 185:60-89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in E. coli is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., FIGS. 2-7) can be expressed in insect cells using baculovirus expression vectors. Baculovirus vectors available for expression of polypeptides in cultured insect cells (e.g., Sf 9 cells) include the pAc 'series (Smith et al. (1983) Mol. Cell Biol. 3:2156-2165) and the pVL series (Lucklow and Summers (1989) Virology 170:31-39).

In yet another embodiment, a nucleic acid of the present invention (e.g., FIGS. 2-7) is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

Another aspect of the invention pertains to host cells into which a nucleic acid molecule of the present invention (e.g., FIGS. 2-7) is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention (e.g., FIGS. 2-7) can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PD-L2 polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the present invention (e.g., FIGS. 2-7). Accordingly, the invention further provides methods for producing a polypeptide of the present invention (e.g., FIGS. 2-7) using the host cells of the present invention. In one embodiment, the method comprises culturing the host cell of the invention (into which a recombinant expression vector encoding a polypeptide of the present invention (e.g., FIGS. 2-7) has been introduced) in a suitable medium such that a polypeptide of the present invention (e.g., FIGS. 2-7) is produced. In another embodiment, the method further comprises isolating a polypeptide of the present invention (e.g., FIGS. 2-7) from the medium or the host cell.

The host cells of the invention can also be used to produce non-human transgenic animals, as described below.

V. Production of Transgenic and Transchromosomal Non-human Animals which Generate Composite, Human PD-1, PD-L1, or PD-L2 Antibodies In yet another aspect, the invention provides transgenic and transchromosomal non-human animals, such as transgenic or transchromosomal mice, which are capable of expressing human monoclonal antibodies that specifically bind to PD-1, PD-L1, or PD-L2. In a particular embodiment, the invention provides a transgenic or transchromosomal mouse having a genome comprising a human heavy chain transgene, such that the mouse produces human anti-PD-1, PD-L1, or PD-L2 antibodies when immunized with PD-1, PD-L1, or PD-L2 antigen and/or cells expressing PD-1, PD-L1, or PD-L2. The human heavy chain transgene can be integrated into the chromosomal DNA of the mouse, as is the case for transgenic, e.g., HuMAb, mice accordingly to methods well known in the art. Alternatively, the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to PD-1, PD-L1, or PD-L2 (e.g., IgG, IgA and/or IgE) by undergoing V-D-J recombination and isotype switching. Isotype switching may occur by, e.g., classical or non-classical isotype switching.

The design of a transgenic or transchromsomal non-human animal that responds to foreign antigen stimulation with a heterologous antibody repertoire, requires that the heterologous immunoglobulin transgenes contained within the transgenic animal function correctly throughout the pathway of B-cell development. This includes, for example, isotype switching of the heterologous heavy chain transgene. Accordingly, transgenes are constructed so as to produce isotype switching and one or more of the following of antibodies: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, Fundamental Immunology, 2nd edition (1989), Paul William E., ed. Raven Press, N.Y.

In certain embodiments, the transgenic or transchromosomal non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one CH gene. In addition, the heavy chain transgene may contain functional isotype switch sequences, which are capable of supporting isotype switching of a heterologous transgene encoding multiple CH genes in the B-cells of the transgenic animal. Such switch sequences may be those which occur naturally in the germline immunoglobulin locus from the species that serves as the source of the transgene CH genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., Nucl. Acids Res. 15:7305 7316 (1991); Sideras et al., Intl. Immunol. 1:631 642 (1989)). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to the PD-1, PD-L1, or PD-L2 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Transgenic and transchromsomal mice employed in the present invention can exhibit immunoglobulin production with a significant repertoire, ideally substantially similar to that of a native mouse. Thus, for example, in embodiments where the endogenous Ig genes have been inactivated, the total immunoglobulin levels can range from about 0.1 to 10 mg/ml of serum, or from about 0.5 to 5 mg/ml, or at least about 1.0 mg/ml. When a transgene capable of effecting a switch to IgG from IgM has been introduced into the transgenic mouse, the adult mouse ratio of serum IgG to IgM can be about 10:1. The IgG to IgM ratio will be much lower in the immature mouse. In general, greater than about 10%, preferably 40 to 80% of the spleen and lymph node B cells express exclusively human IgG protein.

The repertoire will ideally approximate that shown in a native mouse, usually at least about 10% as high, or 25 to 50% or more. Generally, at least about a thousand different immunoglobulins (ideally IgG), e.g., preferably $10^4$ to $10^6$ or more, will be produced, depending primarily on the number of different V, J and D regions introduced into the mouse genome. These immunoglobulins will typically recognize about one-half or more of highly antigenic proteins, e.g., staphylococcus protein A. Typically, the immunoglobulins will exhibit an affinity ($K_D$) for preselected antigens of below $10^{-7}$ M, such as of below $10^{-8}$ M, $10^{-9}$ M or $10^{-10}$ M or even lower.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

Transgenic and transchromosomal mice as described above can be immunized with, for example, a purified or enriched preparation of PD-1, PD-L1, or PD-L2 antigen and/or cells expressing PD-1, PD-L1, or PD-L2. Alternatively, the transgenic mice can be immunized with DNA encoding human PD-1, PD-L1, or PD-L2. The mice will then produce B cells which undergo class-switching via intratransgene switch recombination (cis-switching) and express immunoglobulins reactive with PD-1, PD-L1, or PD-L2. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ or $V_H$ gene segment and a human $J_L$ or $D_H$ and $J_H$ segment, even though other non-germline sequences may be present as a result of somatic mutation and differential V-J and V-D-J recombination joints. The variable regions of each antibody chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Human antibodies which bind to the predetermined antigen can result from isotype switching, such that human antibodies comprising a human sequence γ chain (such as γ1, γ 2a, γ 2B, or γ 3) and a human sequence light chain (such as kappa) are produced. Such isotype-switched human antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human antibodies may have binding affinities ($K_D$) of below $10^{-7}$ M, such as of below $10^{-8}$ M, $10^{-9}$ M, $10^{-10}$ M, $10^{-10}$ M or even lower.

Another aspect of the invention includes B cells derived from transgenic or transchromosomal mice as described herein. The B cells can be used to generate hybridomas expressing human monoclonal antibodies which bind with high affinity (e.g., lower than $10^{-7}$ M) to human PD-1, PD-L1, or PD-L2.

The development of high affinity human monoclonal antibodies against PD-1, PD-L1, or PD-L2 can be facilitated by a method for expanding the repertoire of human variable region gene segments in a transgenic mouse having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which have been classified in four categories:

(1) Transgenic animals containing an unrearranged heavy and rearranged light immunoglobulin transgene;
(2) Transgenic animals containing an unrearranged heavy and unrearranged light immunoglobulin transgene;
(3) Transgenic animal containing rearranged heavy and an unrearranged light immunoglobulin transgene; and
(4) Transgenic animals containing rearranged heavy and rearranged light immunoglobulin transgenes.

VI. Antibody Conjugates/Immunotoxins

In another aspect, the present invention features human PD-1, PD-L1, or PD-L2 antibodies conjugated to a therapeutic moiety, such as a cytotoxin, a drug (e.g., an immunosuppressant) or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated human PD-1, PD-L1, or PD-L2 antibodies can be used diagnostically or prognostically to monitor polypeptide levels in tissue as part of a clinical testing procedure, e.g., to, for example, determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $_{125}I$, $_{131}I$, $_{35}S$ or $_3H$.

The antibody conjugates of the invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

VII. Pharmaceutical Compositions

In another aspect, the present invention provides a composition, e.g., a pharmaceutical composition, containing one or a combination of the monoclonal antibodies, or antigen-binding portion(s) thereof (such as antigen-binding fragments), of the present invention, formulated together with a pharmaceutically acceptable carrier. In one embodiment, the compositions include a combination of multiple (e.g., two or more) isolated human antibodies of the invention. Preferably, each of the antibodies of the composition binds to a distinct, pre-selected epitope of PD-1, PD-L1, and/or PD-L2.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, chemotherapeutics, and psoriasis agents. The pharmaceutical compositions of the invention can also be administered in conjunction with radiation therapy. Co-administration with other antibodies, such as CD4 specific antibodies and IL-2 specific antibodies, are also encompassed by the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1 19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, or about 0.01 to 25 mg/kg body weight, or about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. It will also be appreciated that the effective dosage of antibody used for treatment may increase or decrease over the course of a particular treatment. Changes in dosage may result from the results of diagnostic assays.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, alternatively from about 0.005 percent to about 70 percent, or alternatively from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (e.g., 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in one embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in another embodiment, the liposomes include a targeting moiety. In yet another embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VIII. Uses and Methods of the Invention

The antibodies described herein (including derivatives and conjugates of the antibodies) and compositions containing the antibodies can be used in a variety of in vitro and in vivo diagnostic and therapeutic applications (e.g., by up- or down-modulating the immune response). For example, PD-1 ligand binding to PD-1 or B7-1 transmits an inhibitory signal. Thus, modulation of the interaction between PD-1 and a PD-1 ligand, or between a PD-1 ligand and a B7 polypeptide, results in modulation of the immune response. PD-1 ligands can also costimulate T cells. Thus, in one embodiment, antibodies which block the interaction between a PD-1 ligand and PD-1 or B7 can prevent inhibitory signaling. In one embodiment, antibodies that block costimulatory signal of the PD-1 ligand block a costimulatory signal to an immune cell. Furthermore, ligation of PD-L2 can induce cytokine secretion and survival of dendritic cells. Thus, antibodies that block PD-L2 ligation can inhibit dendritic cell survival and reduce cytokine expression by dendritic cells, and through these mechanisms inhibit an immune response. In particular, antibodies described herein are useful for diagnostic, prognostic, prevention, and therapeutic applications related to particular conditions mediated by PD-1, PD-L1, and/or PD-L2, as discussed, for example, in Keir et al. (2008) Annu. Rev. Immunol. 26:677; Sharpe et al., (2007) Nat. Immunol. 8:239; Freeman et al. (2007) J. Exp. Med. 10:2223; each of which is hereby incorporated by reference in their entirety.

In one embodiment, the antibodies and the antigen-binding fragments of the present invention are useful for diagnostic, prognostic, prevention, and therapeutic applications regarding neurodegenerative diseases (geriopsychosis, Alzheimer disease, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease).

In another embodiment, the antibodies and the antigen-binding fragments of the present invention are useful diagnostic, prognostic, prevention, and therapeutic applications (such as treating, and delaying the onset or progression of the diseases) for diseases that accelerate the immune reaction, for example, asthma, autoimmune diseases (glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis).

In still another embodiment, the antibodies and the antigen-binding fragments of the present invention are useful diagnostic, prognostic, prevention, and therapeutic applications (such as treating, and delaying the onset or progression of the diseases) for therapy and/or prevention for persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Other antigens associated with pathogens that can be utilized as described herein are antigens of various parasites, includes malaria, preferably malaria peptide based on repeats of NANP. In addition, bacterial, fungal and other pathogenic diseases are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria* gonorrhea, *Mycobacterium tuberculosis, Candida albicans, Candida tropicalis, Trichomonas vaginalis, Haemophilus vaginalis*, Group B *Streptococcus* sp., Microplasma *hominis, Hemophilus ducreyi*, Granuloma inguinale, Lymphopathia venereum, *Treponema pallidum, Brucella abortus. Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphy-* lococcus enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium*.

In yet another embodiment, the antibodies or the antigen-binding fragments of the present invention are useful for diagnostic, prognostic, prevention, and therapeutic applications for organ graft rejection, graft-versus-host disease (GVHD), allergic disease, and diseases caused by attenuation of immune reaction, which PD-1, PD-L1, and/or PD-L2 participates, for example, cancer and infectious disease.

The antibodies or antigen-binding fragments described herein are administered to a subject in accord with known methods, such as by intravenous (e.g., as a bolus or by continuous infusion over a period of time), subcutaneous, intramuscular, intraperitoneal, intracerobrospinal, intraarticular, intrasynovial, intrathecal, or inhalation routes administration.

A subject is treated if one or more beneficial or desired results, including desirably clinical results, are obtained. For purposes of this invention, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

1. Screening Methods

One aspect of the present invention relates to methods of using antibodies of the present to modulate an immune response by modulating costimulation (such as antibodies that modulate the function of PD-1, PD-L1, or PD-L2). Such methods utilize screening assays, including cell based and non-cell based assays. In one embodiment, the assays provide a method for identifying antibodies which modulate the interaction of a PD-1 ligand and PD-1. In another embodiment, the assays provide a method for identifying antibodies which modulate the interaction between a PD-1 ligand and a B7 polypeptide.

In one embodiment, the invention relates to assays for screening candidate or test antibodies which bind to, or modulate the activity of, PD-1, PD-L1, or PD-L2, e.g., modulate the ability of the polypeptide to interact with (e.g., bind to) its cognate binding partner. In one embodiment, a method for identifying an antibody to modulate an immune response entails determining the ability of the antibody to modulate, e.g. enhance or inhibit, the interaction between PD-1 and a PD-1 ligand, and further determining the ability of the antibody to modulate the interaction between a PD-1 ligand and a B7 polypeptide. In one embodiment, an antibody that modulates the interaction between the PD-1 ligand and PD-1 (e.g., without modulating the interaction between the PD-1 ligand and the B7 polypeptide is selected). In another embodiment, an antibody that modulates the interaction between a PD-1 ligand and a B7 polypeptide (e.g., without modulating the interaction between the PD-1 ligand and PD-1) is selected.

In another embodiment, a method for identifying an antibody to decrease an immune response entails determining the ability of a candidate antibody to enhance the interaction between a PD-1 ligand and a B7 polypeptide and selecting an antibody that inhibits the interaction between the PD-1 ligand and the B7 polypeptide. In another embodiment, a method for identifying an antibody to decrease an immune response entails determining the ability of the candidate antibody to enhance the interaction between a PD-1 ligand and PD-1 and selecting an antibody that enhances the interaction between the PD-1 ligand and PD-1

In one embodiment, an assay is a cell-based assay, comprising contacting a cell expressing PD-1, PD-L1, or PD-L2, with a test antibody and determining the ability of the test antibody to modulate (e.g. stimulate or inhibit) the binding of PD-1 or the PD-1 ligand target to its binding partner. Determining the ability of the PD-1, PD-1 ligand or B7 polypeptide to bind to, or interact with, its binding partner can be accomplished, e.g., by measuring direct binding or by measuring a parameter of immune cell activation.

For example, in a direct binding assay, the PD-1 or PD-1 ligand protein (or their respective target polypeptides) can be coupled with a radioisotope or enzymatic label such that binding of PD-1 ligand to PD-1 or to the B7 polypeptide can be determined by detecting the labeled protein in a complex. For example, PD-1 or PD-1 can be labeled with $^{125}I$, $^{35}S$, $^{14}C$, or $^3H$, either directly or indirectly, and the radioisotope detected by direct counting of radioemmission or by scintillation counting. Alternatively, PD-1 or PD-1 ligand can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between PD-1 and a PD-1 ligand or between a PD-1 ligand and a B7 polypeptide, without the labeling of any of the interactants. For example, a microphysiometer can be used to detect the interaction of PD-1 and a PD-1 ligand, or between a PD-1 ligand and a B7 polypeptide, with its target polypeptide, without the labeling of either PD-1, PD-1 ligand, B7 polypeptide, or the target polypeptide (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In another embodiment, determining the ability of the antibody to antagonize the interaction between a given set of polypeptides can be accomplished by determining the activity of one or more members of the set of polypeptides. For example, the activity of PD-1 or a PD-1 ligand can be determined by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by PD-1 or the PD-1 ligand. Determining the ability of the antibody to bind to or interact with said polypeptide can be accomplished, for example, by measuring the ability of a compound to modulate immune cell costimulation or inhibition in a proliferation assay, or by interfering with the ability of said polypeptide to bind to antibodies that recognize a portion thereof.

Antibodies that block or inhibit interaction of a PD-1 ligand with a costimulatory receptor as well as antibodies that promote a PD-1 ligand-mediated inhibitory signal can be identified by their ability to inhibit immune cell proliferation, and/or effector function, or to induce anergy when added to an in vitro assay. For example, cells can be cultured in the presence of an agent that stimulates signal transduction via an activating receptor. A number of recognized readouts of cell activation can be employed to measure, cell proliferation or effector function (e.g., antibody production, cytokine production, phagocytosis) in the presence of the activating agent. The ability of a test antibody to block this activation can be readily determined by measuring the ability of the antibody to affect a decrease in proliferation or effector function being measured, using techniques known in the art.

For example, antibodies of the present invention can be tested for the ability to inhibit or enhance costimulation in a T cell assay, as described in Freeman et al. (2000) *J. Exp. Med.* 192:1027 and Latchman et al. (2001) *Nat. Immunol.* 2:261. CD4+ T cells can be isolated from human PBMCs and stimulated with activating anti-CD3 antibody. Proliferation of T cells can be measured by $^3$H thymidine incorporation. An assay can be performed with or without CD28 costimulation in the assay. Similar assays can be performed with Jurkat T cells and PHA-blasts from PBMCs.

In yet another embodiment, an assay of the present invention is a cell-free assay in which PD-1 or a PD-1 ligand or a biologically active portion thereof, is contacted with a test antibody, and the ability of the test antibody to bind to the polypeptide, or biologically active portion thereof, is determined. Binding of the test antibody to the PD-1 or PD-1 ligand polypeptide can be determined either directly or indirectly as described above. In still another embodiment, the assay includes contacting the polypeptide, or biologically active portion thereof, with its binding partner to form an assay mixture, contacting the assay mixture with a test antibody, and determining the ability of the test antibody to interact with the polypeptide in the assay mixture, wherein determining the ability of the test antibody to interact with the polypeptide comprises determining the ability of the test antibody to preferentially bind to the polypeptide or biologically active portion thereof, as compared to the binding partner.

For example, a PD-1 ligand and a PD-1 polypeptide can be used to form an assay mixture and the ability of a test antibody to block this interaction can be tested by determining the ability of PD-1 to bind the PD-1 ligand and determining the ability of the PD-1 ligand to bind the PD-1 polypeptide, by one of the methods described above for determining binding. Determining the ability of a PD-1 polypeptide to bind a PD-1 ligand and determining the ability of a PD-1 ligand to bind a B7 polypeptide can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. PD-1, PD-1 ligand, and B7 polypeptide can be immobilized on a BIAcore chip and antibodies can be tested for binding to PD-1, PD-1 ligand, and B7 polypeptide. An example of using the BIA technology is described by Fitz et al. (1997) *Oncogene* 15:613.

The cell-free assays of the present invention are amenable to use of both soluble and/or membrane-bound forms of proteins (e.g., a PD-1 ligand or PD-1 proteins or biologically active portions thereof, or binding partners to which a PD-1 ligand or PD-1 binds). In the case of cell-free assays in which a membrane-bound form protein is used (e.g., a cell surface PD-1 ligand or PD-1 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either PD-1, a PD-1 ligand, and a B7 polypeptide, or an appropriate target polypeptide, to facilitate separation of complexed from uncomplexed forms of one or both of the proteins, as well as to accommodate automation of the assay. Binding of a test antibody to PD-1 or a PD-1 ligand can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/PD-1, PD-1 ligand, or B7 polypeptide fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PD-1, PD-1 ligand, or B7 polypeptide binding or activity determined using standard techniques.

In an alternative embodiment, determining the ability of the test compound to modulate the activity of PD-1 or a PD-1 ligand can be accomplished by determining the ability of the test antibody to modulate the activity of a polypeptide that functions downstream of PD-1 or the PD-1 ligand, e.g., a polypeptide that interacts with the PD-1 ligand, or a polypeptide that functions downstream of PD-1, e.g., by interacting with the cytoplasmic domain of PD-1. For example, levels of second messengers can be determined, the activity of the interactor polypeptide on an appropriate target can be determined, or the binding of the interactor to an appropriate target can be determined as previously described.

This invention further pertains to novel antibodies identified by the above-described screening assays. Accordingly, it is within the scope of this invention to further use an antibody identified as described herein in an appropriate animal model. For example, an antibody identified as described herein can be used in an animal model to determine the efficacy, toxicity, or side effects of treatment with such an antibody. Alternatively, an antibody identified as described herein can be used in an animal model to determine the mechanism of action of such an antibody. Furthermore, this invention pertains to uses of novel antibodies identified by the above-described screening assays for treatments as described herein.

2. Prophylactic Methods

In one aspect, the invention relates to a method for preventing in a subject, a disease or condition associated with an unwanted or less than desirable immune response. Subjects at risk for a disease that would benefit from treatment with the claimed antibodies or methods can be identified, for example, by any or a combination of diagnostic or prognostic assays known in the art. Administration of a prophylactic antibody can occur prior to the manifestation of symptoms associated with an unwanted or less than desirable immune response. The appropriate antibody used for treatment can be determined based on clinical indications and can be identified, e.g., using screening assays described herein.

3. Therapeutic Methods

Another aspect of the invention pertains to therapeutic methods of modulating an immune response, e.g., by modulating the interaction between PD-1 and a PD-1 ligand and/or a PD-1 ligand and a B7 polypeptide. For example, modulation of the interaction between PD-1 and a PD-1 ligand, or between a PD-1 ligand and a B7 polypeptide, results in modulation of the immune response. Thus, in one embodiment, antibodies which block the interaction between PD-1 and the PD-1 ligand can prevent inhibitory signaling. PD-1 ligands can also enhance costimulatory signals in T cells. Thus, in another embodiment, antibodies that prevent PD-1 ligand from providing a costimulatory signal can inhibit T cell costimulation.

These modulatory antibodies can be administered in vitro (e.g., by contacting the cell with an antibody) or, alternatively, in vivo (e.g., by administering the agent to a subject). As such, the present invention relates to methods of treating an individual afflicted with a disease or disorder that would benefit from modulation of an immune response, e.g., by modulation of the interaction between a PD-1 ligand and PD-1, or a B7 polypeptide.

4. Downregulation of Immune Responses

There are numerous embodiments of the invention for upregulating the inhibitory function or downregulating the costimulatory function of a PD-1 ligand to thereby downregulate immune responses. Downregulation can be in the form of inhibiting or blocking an immune response already in progress, or may involve preventing the induction of an immune response. The functions of activated immune cells can be inhibited by down-regulating immune cell responses, or by inducing specific anergy in immune cells, or both.

For example, the immune response can be downmodulated using: anti-PD-1 ligand antibodies that blocks costimulation by PD-1 ligand (e.g., while not affecting or increasing the interaction between PD-L1 and PD-1) or which promote the binding of a PD-1 ligand with PD-1, (e.g., while not affecting or while inhibiting costimulation by PD-1 ligand).

In one embodiment of the invention, tolerance is induced against specific antigens by co-administering an antigen with an antibody which blocks PD-1 ligand costimulation. For example, tolerance can be induced to specific proteins. In one embodiment, immune responses to allergens, or to foreign proteins to which an immune response is undesirable, can be inhibited. For example, patients that receive Factor VIII frequently generate antibodies against this clotting factor. Co-administration of an antibody that blocks a PD-1 ligand-mediated costimulatory signal or an antibody that stimulates a PD-1 mediated inhibitory signal in combination with recombinant factor VIII (or by physically linked to Factor VIII, e.g., by cross-linking) can result in downmodulation.

In one embodiment, two separate agents that downmodulate immune responses can be combined as a single composition or administered separately (simultaneously or sequentially) to more effectively downregulate immune cell mediated immune responses in a subject. Furthermore, a therapeutically active amount of one or more of the subject antibodies, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Downregulating or preventing a PD-1 ligand costimulation, or promoting an interaction between a PD-1 ligand and PD-1 is useful to downmodulate the immune response, e.g., in situations of tissue, skin and organ transplantation, in graft-versus-host disease (GVHD), or in inflammatory diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an antibody which inhibits PD-1 ligand costimulation alone or in conjunction with another downmodulatory agent, prior to or at the time of transplantation can promote the generation of an inhibitory signal. Moreover, inhibition of PD-1 ligand costimulatory signals, or promotion of a PD-1 ligand or PD-1 inhibitory signals, may also be sufficient to anergize the immune cells, thereby inducing tolerance in a subject. Induction of long-term tolerance by blocking a PD-1 ligand mediated costimulatory signal may avoid the necessity of repeated administration of these blocking reagents.

To achieve sufficient immunosuppression or tolerance in a subject, it may also be desirable to block the costimulatory function of other polypeptides. For example, it may be desirable to block the function of B7-1, B7-2, or B7-1 and B7-2 by administering a soluble form of a combination of peptides having an activity of each of these antigens, blocking antibodies against these antigens or blocking small molecules (separately or together in a single composition) prior to or at the time of transplantation. Alternatively, it may be desirable to promote inhibitory activity of a PD-1 ligand or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Downmodulation of immune responses are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of reagents which block costimulation of immune cells by disrupting interactions between PD-1 ligand and B7 polypeptides, or by promoting the interaction between PD-1 ligand and PD-1, without modulating or while downmodulating the interaction between PD-1 ligand and a B7 polypeptide, are useful for inhibiting immune cell activation and preventing production of autoantibodies or cytokines which may be involved in the disease process. Additionally, agents that promote an inhibitory function of a PD-1 ligand or PD-1 may induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is useful therapeutically in the treatment of allergy and allergic reactions, e.g., by inhibiting IgE production. An antibody that promotes a PD-1 ligand or PD-1 inhibitory function can be administered to an allergic subject to inhibit immune cell mediated allergic responses in the subject. Inhibition of PD-1 ligand costimulation of immune cells or stimulation of a PD-1 ligand or PD-1 inhibitory pathway can be accompanied by exposure to allergen in conjunction with appropriate MHC polypeptides. Allergic reactions can be systemic or local in nature, depending on the route of entry of the allergen and the pattern of deposition of IgE on mast cells or basophils. Thus, inhibition of immune cell mediated allergic responses locally or systemically by administration of an inhibitory form of an agent that inhibits the interaction of a PD-1 ligand with a costimulatory receptor, or an antibody that promotes an inhibitory function of a PD-1 ligand or PD-1.

Inhibition of immune cell activation through blockage of PD-1 ligand costimulation, or through promotion of the interaction between a PD-1 ligand and PD-1, may also be important therapeutically in viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. PD-1 ligand is normally highly expressed in placental trophoblasts, the layer of cells that forms the interface between mother and fetus and may play a role in preventing maternal rejection of the fetus. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response by modulation of PD-1 ligand costimulation or by modulation of PD-1 ligand/PD-1 binding may also be useful in treating an autoimmune attack of autologous tissues. For example, PD-1 ligand is normally highly expressed in the heart and may protect the heart from autoimmune attack. This is evidenced by the fact that the Balb/c PD-1 knockout mouse exhibits massive autoimmune attack on the heart with thrombosis. Thus, conditions that are caused or exacerbated by autoimmune attack (e.g., in this example, heart disease, myocardial infarction or atherosclerosis) may be ameliorated or improved by modulation of these interactions. It is therefore within the scope of the invention to modulate conditions exacerbated by autoimmune attack, such as autoimmune disorders (as well as conditions such as heart disease, myocardial infarction, and atherosclerosis).

5. Upregulation of Immune Responses

Also useful therapeutically is the blockage of the interaction of a PD-1 ligand with PD-1 or B7-1 as a means of upregulating an immune response. Upregulation of immune responses can be in the form of enhancing an existing immune response or eliciting an initial immune response. For instance, enhancing an immune response using the subject compositions and methods is useful in cases of infections with microbes (e.g., bacteria, viruses, or parasites). In one embodiment, an antibody that blocks the interaction of a PD-1 ligand with PD-1 is used to enhance the immune response. Such an antibody (e.g., a non-activating antibody that blocks PD-L1 binding to PD-1) is therapeutically useful in situations where upregulation of antibody and cell-mediated responses would be beneficial. Exemplary disorders include viral skin diseases, such as Herpes or shingles, in which case such an agent can be delivered topically to the skin. In addition, systemic viral diseases such as influenza, the common cold, and encephalitis might be alleviated by systemic administration of such agents.

Alternatively, immune responses can be enhanced in an infected patient through an ex vivo approach, for instance, by removing immune cells from the patient, contacting immune cells in vitro with an antibody that blocks the interaction of a PD-1 ligand with PD-1 and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response.

An antibody that blocks the interaction of a PD-1 ligand with PD-1 or B7-1 can be used prophylactically in vaccines against various polypeptides (e.g., polypeptides derived from pathogens). Immunity against a pathogen (e.g., a virus) can be induced by vaccinating with a viral protein along with an antibody that blocks the interaction of a PD-1 ligand with PD-1 or B7-1 in an appropriate adjuvant.

In another embodiment, upregulation or enhancement of an immune response function, as described herein, is useful in the induction of tumor immunity In another embodiment, the immune response can be stimulated by the methods described herein, such that pre-existing tolerance is overcome. For example, immune responses against antigens to which a subject cannot mount a significant immune response, e.g., to an autologous antigen, such as a tumor specific antigens can be induced by administering an antibody that blocks the interaction of a PD-1 ligand with PD-1. In one embodiment, an autologous antigen, such as a tumor-specific antigen can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In one embodiment, immune cells are obtained from a subject and cultured ex vivo in the presence of an antibody as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

EXAMPLES

The examples below describe the generation of monoclonal antibodies suitable for therapeutic purposes targeting human PD-1, PD-L1 and PD-L2. Composite, human anti-human PD-1, PD-L1 and PD-L2 antibodies were generated from mouse anti-human EH12.2H7, 29E.2A3 and 24F.10C12 antibodies, respectively. Segments of human V region sequence were sourced from unrelated human antibody (germline and non-germline) sequence databases. Each selected sequence segment (as well as the junctions between segments) was tested for the potential to bind to MHC class II using binding prediction algorithms. All final composite, human antibody sequence variants were designed to avoid T cell epitopes. Composite, human antibody V region genes were generated using synthetic oligonucleotides encoding combinations of the human sequence segments. These were then cloned into vectors containing human constant regions, and antibodies were produced and tested for binding to target antigens by competition ELISA.

Example 1: Design of Composite, Human Antibody Variable Region Sequences

Structural models of the mouse EH12.2H7, 29E.2A3 and 24F.10C12 V regions were produced using Swiss Pdb and analyzed in order to identify important "constraining" amino acids in the mouse V regions that might be essential for the binding properties of the antibodies. Only residues contained within the CDRs were considered to be important, including CDR residues defined under both Kabat and Chothia definitions.

From the above analysis, it was considered that composite, human forms of EH12.2H7, 29E.2A3 and 24F.10C12 could be created with wide latitude of sequences outside of CDRs but with a narrow menu of possible alternative residues within the CDR sequences. Preliminary analysis indicated that corresponding sequence segments from several human antibodies could be combined to create CDRs similar or identical to those in the mouse sequences. For regions outside of and flanking the CDRs, a wide selection of human sequence segments were identified as possible components of the novel composite, human antibody variable regions.

Based upon the above analysis, a large preliminary set of sequence segments that could be used to create EH12.2H7, 29E.2A3 and 24F.10C12 composite, human antibody variants were selected and analyzed via MHC class II binding prediction algorithms and BLAST searched through a proprietary database of known antibody sequence related T cell epitopes. Sequence segments where potential MHC class II binding peptides were identified, or scored significant hits against the database of known T cell epitopes, were discarded. This resulted in a reduced set of segments, and combinations of these were again analyzed, as above, to ensure that junctions between segments did not contain potential T cell epitopes. Selected segments were then combined to produce heavy and light chain variable region sequences for synthesis. For all three antibodies, five heavy chains and four light chains were constructed with sequences detailed as follows;

| Antigen | Composite VH Sequences | Composite VK Sequences |
|---|---|---|
| PD-1 | FIGS. 2A-2E | FIGS. 3A-3D |
| PD-L1 | FIGS. 4A-4E | FIGS. 5A-5D |
| PD-L2 | FIGS. 6A-6E | FIGS. 7A-7D |

Sequence segments used to produce these composite, human antibody sequences are detailed in Tables 1, 2, and 3 for antibodies against PD-1, PD-L1 and PD-L2 respectively.

TABLE 1

Derivation of Human Sequence Segments that Comprise the Anti-PD-1 Composite, Human Antibodies (a)

| Genbank Accession No. | VH3 Sequence |
|---|---|
| BAA75018 | QVQLVQSGHEVKQPGASVK (SEQ ID NO: 82) |
| AAG00910 | MSCKASGYSFTS (SEQ ID NO: 83) |
| AAY18543 | SGYSFTSSWI (SEQ ID NO: 84) |
| AAY57105 | WIHWV (SEQ ID NO: 85) |
| AAG00910 | KQ |
| AAD16517 | QAPGQGLEWIG (SEQ ID NO: 86) |
| AAD53797 | GLEWIGYIYPS (SEQ ID NO: 87) |
| CAA08742 | STGF (SEQ ID NO: 88) |

TABLE 1-continued

Derivation of Human Sequence Segments that Comprise the Anti-PD-1 Composite, Human Antibodies

| | |
|---|---|
| CAC87219 | TEYN (SEQ ID NO: 89) |
| AAT96419 | QKF |
| AAA17939 | KDR |
| AAR02530 | DRAT (SEQ ID NO: 90) |
| AAA17939 | TLT |
| AAM87977 | TADKSTSTAYMELSSLRSEDTAVYYCAR (SEQ ID NO: 91) |
| CAA78534 | STAYMELSSLRSEDTAVYYCARWRD (SEQ ID NO: 92) |
| AAV40096 | DSSGY (SEQ ID NO: 93) |
| AAR38557 | YHA |
| AAW29142 | AMD |
| IGHJ4 | DYWGQGTLVTVSS (SEQ ID NO: 94) |

(b)

| Genbank Accession No. | VH4 Sequence |
|---|---|
| BAA75018 | QVQLVQSGHEVKQPGASVK (SEQ ID NO: 82) |
| AAG00910 | MSCKASGYSFTS (SEQ ID NO: 83) |
| AAY18543 | SGYSFTSSWI (SEQ ID NO: 84) |
| AAA02616 | HWVRQAPGQGLEWIG (SEQ ID NO: 95) |
| AAD53797 | GLEWIGYIYPS (SEQ ID NO: 87) |
| CAA08742 | STGF (SEQ ID NO: 88) |
| CAC87219 | TEYN (SEQ ID NO: 89) |
| AAT96419 | QKF |
| AAA17939 | KDR |
| AAR02530 | DRAT (SEQ ID NO: 90) |
| AAA17939 | TLT |
| AAM87977 | TADKSTSTAYMELSSLRSEDTAVYYCAR (SEQ ID NO: 91) |
| CAA78534 | STAYMELSSLRSEDTAVYYCARWRD (SEQ ID NO: 92) |
| AAV40096 | DSSGY (SEQ ID NO: 93) |
| AAR38557 | YHA |
| AAW29142 | AMD |
| IGHJ4 | DYWGQGTLVTVSS (SEQ ID NO: 94) |

(c)

| Genbank Accession No. | Vκ3 Sequence |
|---|---|
| AAY16615 | EIVLTQSPATLSLSPGQR (SEQ ID NO: 96) |
| AAD09377 | RLTISCRASQ (SEQ ID NO: 97) |
| AAA99362 | TISCRASQSVST (SEQ ID NO: 98) |
| AAL04518 | SVSTSGYSYMHW (SEQ ID NO: 99) |

TABLE 1-continued

Derivation of Human Sequence Segments that Comprise the Anti-PD-1 Composite, Human Antibodies

| | |
|---|---|
| AAA58912 | WYQQKPDQSPKLLIK (SEQ ID NO: 100) |
| AAD16648 | FGS |
| AAD19478 | SNLESG (SEQ ID NO: 101) |
| AAL10884 | GIPARFSGSGSGTDFTLTISSLEPEDFA (SEQ ID NO: 102) |
| AAD16559 | PEDFATYYCQHS (SEQ ID NO: 103) |
| AAA99326 | SW |
| AAC16811 | EIP |
| human J2 | YTFGQGTKLEIK (SEQ ID NO: 104) |

(d)

| Genbank Accession No. | Vκ4 Sequence |
|---|---|
| AAB53267 | DIVLTQSP (SEQ ID NO: 105) |
| AAY16615 | IVLTQSPATLSLSPGQR (SEQ ID NO: 106) |
| AAD09377 | RLTISCRASQ (SEQ ID NO: 97) |
| AAA99362 | TISCRASQSVST (SEQ ID NO: 98) |
| AAL04518 | SVSTSGYSYMHW (SEQ ID NO: 99) |
| AAA58912 | WYQQKPDQSPKLLIK (SEQ ID NO: 100) |
| AAD16648 | FGS |
| AAD19478 | SNLESG (SEQ ID NO: 101) |
| AAL10884 | GIPARFSGSGSGTDFTLTISSLEPEDFA (SEQ ID NO: 102) |
| AAD16559 | PEDFATYYCQHS (SEQ ID NO: 103) |
| AAA99326 | SW |
| AAC16811 | EIP |
| human J2 | YTFGQGTKLEIK (SEQ ID NO: 104) |

TABLE 2

Derivation of Human Sequence Segments that Comprise the Anti-PD-L1 Composite, Human Antibodies (a)

| Genbank Accession No. | VH2 Sequence |
|---|---|
| ABI50688 | EVQLVQSGAEVKKPGASVK (SEQ ID NO: 107) |
| AAG00910 | MSCKASGY (SEQ ID NO: 108) |
| ABI50688 | SCKASGYTFTSY (SEQ ID NO: 109) |
| AAC50839 | SYVMHWV (SEQ ID NO: 110) |
| CAC43594 | WVKQ (SEQ ID NO: 111) |
| AAA18267 | QAPGQRLEWIG (SEQ ID NO: 112) |
| ABF20472 | GY |

TABLE 2-continued

Derivation of Human Sequence Segments that Comprise the Anti-PD-L1 Composite, Human Antibodies

| | |
|---|---|
| AAD30737 | VNPF (SEQ ID NO: 113) |
| CAL06274 | NDGT (SEQ ID NO: 114) |
| CAC43212 | KYN |
| CAC87219 | YNE |
| CAD31770 | EM |
| AAR32413 | FKGR (SEQ ID NO: 115) |
| AAG30515 | GRAT (SEQ ID NO: 116) |
| ABA62048 | TLT |
| ABI50549 | TSD |
| AAR32572 | DKSTSTAYMELSSLRSEDTAVYYCA (SEQ ID NO: 117) |
| AAC18225 | AVYYCARQA (SEQ ID NO: 118) |
| AAV39747 | AWGY (SEQ ID NO: 119) |
| IGHJ5*02 | PWGQGTLVTVSS (SEQ ID NO: 120) |

(b)

| Genbank Accession No. | VH4 Sequence |
|---|---|
| ABI50688 | EVQLVQSGAEVKKPGASVK (SEQ ID NO: 107) |
| AAG00910 | MSCKASGY (SEQ ID NO: 108) |
| ABI50688 | SCKASGYTFTSY (SEQ ID NO: 109) |
| AAC50839 | SYVMHWV (SEQ ID NO: 110) |
| AAA18267 | WVRQAPGQRLEWIG (SEQ ID NO: 121) |
| ABF20472 | GY |
| AAD30737 | VNPF (SEQ ID NO: 113) |
| CAL06274 | NDGT (SEQ ID NO: 114) |
| CAC43212 | KYN |
| CAC87219 | YNE |
| CAD31770 | EM |
| AAR32413 | FKGR (SEQ ID NO: 115) |
| AAG30515 | GRAT (SEQ ID NO: 116) |
| ABA62048 | TLT |
| ABI50549 | TSD |
| AAR32572 | DKSTSTAYMELSSLRSEDTAVYYCA (SEQ ID NO: 117) |
| AAC18225 | AVYYCARQA (SEQ ID NO: 118) |
| AAV39747 | AWGY (SEQ ID NO: 119) |
| IGHJ5*02 | PWGQGTLVTVSS (SEQ ID NO: 120) |

TABLE 2-continued

Derivation of Human Sequence Segments that Comprise the Anti-PD-L1 Composite, Human Antibodies (c)

| Genbank Accession No. | Vκ1 Sequence |
|---|---|
| CAA31193 | DIVLTQSPASLALS (SEQ ID NO: 122) |
| ABA26115 | LSPGERAT (SEQ ID NO: 123) |
| AAQ21828 | ESV |
| CAA51101 | VE |
| AAA58691 | YYGTSL (SEQ ID NO: 124) |
| AAY33369 | VQWYQQKPGQ (SEQ ID NO: 125) |
| ABI74051 | WYQQKPGQPPKLLIY (SEQ ID NO: 126) |
| CAC39383 | PKLLIYAASS (SEQ ID NO: 127) |
| CAA38592 | SVDS (SEQ ID NO: 128) |
| AAK26833 | DSGVPSRFSGSGSGT (SEQ ID NO: 129) |
| AAM46660 | RFSGSGSGTDFTLTINSLE (SEQ ID NO: 130) |
| AAL04518 | EEEDAA (SEQ ID NO: 131) |
| AAK68016 | AMYFCQQ (SEQ ID NO: 132) |
| CAK50767 | SR |
| AAP23227 | RVPYTFG (SEQ ID NO: 133) |
| Human J2 | YTFGQGTKLEIK (SEQ ID NO: 104) |

(d)

| Genbank Accession No. | Vκ2 Sequence |
|---|---|
| CAA31193 | DIVLTQSPASLALS (SEQ ID NO: 122) |
| CAE54363 | IVLTQSPATLSLSPGE (SEQ ID NO: 134) |
| ABA26115 | LSPGERAT (SEQ ID NO: 123) |
| AAQ21828 | ESV |
| CAA51101 | VE |
| AAA58691 | YYGTSL (SEQ ID NO: 124) |
| AAY33369 | VQWYQQKPGQ (SEQ ID NO: 125) |
| ABI74051 | WYQQKPGQPPKLLIY (SEQ ID NO: 126) |
| CAC39383 | PKLLIYAASS (SEQ ID NO: 127) |
| CAA38592 | SVDS (SEQ ID NO: 128) |
| AAK26833 | DSGVPSRFSGSGSGT (SEQ ID NO: 129) |
| AAM46660 | RFSGSGSGTDFTLTINSLE (SEQ ID NO: 130) |
| AAA58912 | TINSLEAEDAA (SEQ ID NO: 135) |
| AAK68016 | AMYFCQQ (SEQ ID NO: 132) |
| CAK50767 | SR |
| AAP23227 | RVPYTFG (SEQ ID NO: 133) |
| Human J2 | YTFGQGTKLEIK (SEQ ID NO: 104) |

TABLE 2-continued

Derivation of Human Sequence Segments that Comprise the Anti-PD-L1 Composite, Human Antibodies (e)

| Genbank Accession No. | Vκ4 Sequence |
|---|---|
| CAA31193 | DIVLTQSPASLALS (SEQ ID NO: 122) |
| CAE54363 | IVLTQSPATLSLSPGE (SEQ ID NO: 134) |
| ABA26115 | LSPGERAT (SEQ ID NO: 123) |
| AAQ21828 | ESV |
| CAA51101 | VE |
| AAA58691 | YYGTSL (SEQ ID NO: 124) |
| AAY33369 | VQWYQQKPGQ (SEQ ID NO: 125) |
| ABI74051 | WYQQKPGQPPKLLIY (SEQ ID NO: 126) |
| CAC39383 | PKLLIYAASS (SEQ ID NO: 127) |
| CAA38592 | SVDS (SEQ ID NO: 128) |
| AAK26833 | DSGVPSRFSGSGSGT (SEQ ID NO: 129) |
| AAM46660 | RFSGSGSGTDFTLTINSLE (SEQ ID NO: 130) |
| AAA58912 | TINSLEAEDAATYFC (SEQ ID NO: 136) |
| AAK68016 | AMYFCQQ (SEQ ID NO: 132) |
| CAK50767 | SR |
| AAP23227 | RVPYTFG (SEQ ID NO: 133) |
| Human J2 | YTFGQGTKLEIK (SEQ ID NO: 104) |

TABLE 3

Derivation of Human Sequence Segments that Comprise the Anti-PD-L2 Composite, Human Antibodies (a)

| Genbank Accession No. | VH2 Sequence |
|---|---|
| ABF83419 | QVQLVQSGAEVKKPGASVK (SEQ ID NO: 137) |
| AAG00910 | MSCKASGY (SEQ ID NO: 108) |
| ABF83419 | SCKASGYTFTGY (SEQ ID NO: 138) |
| AAL17955 | TMHWV (SEQ ID NO: 139) |
| CAC43594 | WVKQ (SEQ ID NO: 111) |
| AAL17955 | QAPG (SEQ ID NO: 140) |
| AAF40162 | GQGLEWIG (SEQ ID NO: 141) |
| AAR02558 | GYINP (SEQ ID NO: 142) |
| AAR32283 | INPRSG (SEQ ID NO: 143) |
| AAR02553 | GYT |
| CAC87219 | TEYN (SEQ ID NO: 89) |
| AAT96419 | QKF |
| AAA17939 | KDR |

TABLE 3-continued

Derivation of Human Sequence Segments that Comprise the Anti-PD-L2 Composite, Human Antibodies

| Genbank Accession No. | Sequence |
|---|---|
| AAB06403 | RTT |
| AAA17939 | TLT |
| AAG30529 | TADKSTSTAYMELSSLRSEDTAVYYCAR (SEQ ID NO: 91) |
| ABE66740 | DTAVYYCARPW (SEQ ID NO: 144) |
| ABK81281 | WFAYWGQGT (SEQ ID NO: 145) |
| IGHJ4 | YWGQGTLVTVSS (SEQ ID NO: 146) |

(b)

| Genbank Accession No. | VH4 Sequence |
|---|---|
| ABF83419 | QVQLVQSGAEVKKPGASVKVSCKASGYTFTGY (SEQ ID NO: 147) |
| AAL17955 | TMHWVRQAPG (SEQ ID NO: 148) |
| AAF40162 | GQGLEWIG (SEQ ID NO: 141) |
| AAR02558 | GYINP (SEQ ID NO: 142) |
| AAR32283 | INPRSG (SEQ ID NO: 143) |
| AAR02553 | GYT |
| CAC87219 | TEYN (SEQ ID NO: 89) |
| AAT96419 | QKF |
| AAA17939 | KDR |
| AAB06403 | RTT |
| AAA17939 | TLT |
| AAG30529 | TADKSTSTAYMELSSLRSEDTAVYYCAR (SEQ ID NO: 91) |
| ABE66740 | DTAVYYCARPW (SEQ ID NO: 144) |
| ABK81281 | WFAYWGQGT (SEQ ID NO: 145) |
| IGHJ4 | YWGQGTLVTVSS (SEQ ID NO: 146) |

(C)

| Genbank Accession No. | Vκ2 Sequence |
|---|---|
| AAD16249 | DIVMTQSP (SEQ ID NO: 149) |
| CAA31193 | PASL (SEQ ID NO: 150) |
| AAA58913 | LSVTPGEKVTITC (SEQ ID NO: 151) |
| AAQ99244 | CKSSQSLL (SEQ ID NO: 152) |
| ABA71421 | LNS |
| AAD19451 | GN |
| AAS86065 | QK |
| AAD14073 | KNYLTWYQQKPGQPPKLLIYWASTRESGVPDRF (SEQ ID NO: 153) |
| AAZ09126 | RFTGSGSGTDFTLTISSLQAEDVAVYYCQ (SEQ ID NO: 154) |
| CAA31484 | NDY |

TABLE 3-continued

Derivation of Human Sequence Segments that Comprise the Anti-PD-L2 Composite, Human Antibodies

| | |
|---|---|
| CAC87582 | YSYPL (SEQ ID NO: 155) |
| human J1 | TFGQGTKLEIK (SEQ ID NO: 156) |

(d)

| Genbank Accession No. | Vκ3 Sequence |
|---|---|
| AAD16249 | DIVMTQSP (SEQ ID NO: 149) |
| AAA58913 | VMTQSPAFLSVTPGEKVTITC (SEQ ID NO: 157) |
| AAQ99244 | CKSSQSLL (SEQ ID NO: 152) |
| ABA71421 | LNS |
| AAD19451 | GN |
| AAS86065 | QK |
| AAD14073 | KNYLTWYQQKPGQPPKLLIYWASTRESGVPDRF (SEQ ID NO: 153) |
| AAZ09126 | RFTGSGSGTDFTLTISSLQAEDVAVYYCQ (SEQ ID NO: 154) |
| CAA31484 | NDY |
| CAC87582 | YSYPL (SEQ ID NO: 155) |
| human J1 | TFGQGTKLEIK (SEQ ID NO: 156) |

(e)

| Genbank Accession No. | Vκ4 Sequence |
|---|---|
| AAD16249 | DIVMTQSP (SEQ ID NO: 149) |
| AAA58913 | VMTQSPAFLSVTPGEKVTITC (SEQ ID NO: 157) |
| AAQ99244 | CKSSQSLL (SEQ ID NO: 152) |
| ABA71421 | LNS |
| AAD19451 | GN |
| AAS86065 | QK |
| AAD14073 | KNYLTWYQQKPGQPPKLLIYWASTRESGVPDRF (SEQ ID NO: 153) |
| CAD44754 | RFSGSGSGTDFTLTISSLQAEDVAVYYCQ (SEQ ID NO: 158) |
| CAA31484 | NDY |
| CAC87582 | YSYPL (SEQ ID NO: 155) |
| human J1 | TFGQGTKLEIK (SEQ ID NO: 156) |

Example 2: Generation and Testing of Composite, Human Antibodies

Initial variant 1 composite, human antibody VH and VK region genes were synthesized for EH12.2H7, 29E.2A3 and 24F.10C12 using a series of overlapping oligonucleotides that were annealed, ligated and PCR amplified to give full length synthetic V-regions (FIG. 2A, FIG. 3A, FIG. 4A, FIG. 5A, FIG. 6A and FIG. 7A). For each composite, human antibody, subsequent sequence variants were constructed using long overlapping oligonucleotides and PCR, using the initial variant 1 as the template. The assembled variants were then cloned directly into expression vectors (FIG. 1) and their sequences were verified.

All combinations of chimeric and composite heavy and light chains (i.e. a total of 20 pairings for each antibody) were stably transfected into NS0 cells by electroporation and selected in media (high glucose DMEM with L-glutamine and Na pyruvate, 5% ultra-low IgG FCS, pen/strep—all from Invitrogen) containing 200 nM methotrexate. Several drug resistant colonies for each construct were tested for expression levels and the best expressing lines were selected and frozen under liquid nitrogen.

Supernatants from the best expressing lines for each combination were quantified using an Fc capture, Kappa light chain detection ELISA in comparison to a IgG1/kappa standard. The quantified supernatants were then tested in a competition ELISA for binding to their target antigen. Ninety-six well Maxisorb™ plates (Nunc) were coated overnight at 4° C. with 50 μl/well of 1 μg/ml human Fc-PD-1, Fc-PD-L1 or Fc-PD-L2 (R&D systems) in carbonate buffer pH 9.6. Duplicate titrations of mouse reference antibody and composite, human antibody samples were generated (in the range 0.0078 μg/ml to 8 μg/ml) and mixed with a constant concentration (40 ng/ml) of biotinylated mouse reference antibody in PBS pH 7.4/2% BSA. The titrations, 100 μl/well, were added to washed (4× with PBS pH 7.4/0.05% Tween 20) assay plates and incubated at room temperature for 1 hour. Plates were washed as above and 100 μl/well of a 1/1000 dilution of streptavidin HRP (Sigma) in PBS pH 7.4/2% BSA was added and incubated for a further 1 hour at room temperature. After a further wash, bound biotinylated reference antibody was detected with 100 μl/well OPD substrate. Absorbance was measured at 490 nm and the binding curves of the test antibodies were compared to the mouse reference standard. Absorbance was plotted against sample concentration and straight lines were fitted through each of the data sets. The equations of the lines were used to calculate the concentration required to inhibit Biotin-EH12.2H7 binding to PD-1, Biotin-29E.2A3 binding to PD-L1 and Biotin-24F.10C12 binding to human PD-L2 by 50% ($IC_{50}$).

The antibodies with the best $IC_{50}$ were selected and cell lines for all these variants of EH12.2H7, 29E.2A3 and 24F.10C12 antibodies were bulked up to 100 ml and grown to saturation. Antibodies were purified from each culture via protein A affinity chromatography. Briefly, supernatants were pH adjusted with 0.1 volume of 10×PBS pH 7.4 and passed over 1 ml Mab Select Sure protein A columns (GE Healthcare). The columns were washed with 10 volumes of PBS pH 7.4 before elution with 50 mM citrate buffer pH 3.0. 1 ml fractions were collected and immediately neutralized with 0.1 ml of 1 m Tris-HCl pH 9.0. Protein containing fractions (as judged by absorbance at 280 nm) were pooled, buffer exchanged into PBS pH 7.4 and the purified antibodies stored at +4° C. FIGS. 8A-8C show a SDS-PAGE gel of 1 μg of each antibody, stained with coomassie blue. The concentrations of the antibodies were calculated by UV absorption based upon calculated molar extinction coefficients such that $E_{0.1}\%$ at 280 nm=1.61 for EH12.2H7, $E_{0.1}\%$ at 280 nm=1.46 for 29E.2A3 and $E_{0.1}\%$ at 280 nm=1.57 for 24F.10C12.

The purified antibodies were tested for binding to human Fc-PD-1, Fc-PD-L1 or Fc-PD-L2 via competition ELISA as described above. Titrations of the test antibodies were done from 0.0625 μg/ml to 8.0 μg/ml in duplicate. Absorbance at 490 nm was measured and this was plotted against test antibody concentration (FIGS. 9A-9C and 10A-10C).

Table 4 summarizes the results for the combinations of the composite VH and VK variant sequences for the anti-PD-1, PD-L1 and PD-L2 antibodies. For EH12.2H7 all the humanized antibodies have an IC50 that is improved compared to the mouse reference, particularly VH4/VK3 that has a two-fold increase in binding. In the case of 29E.2A3, variants VH2/VK1 and VH2/VK4 have equivalent binding to the mouse reference whereas variants VH2/VK2 and VH4/VK2 have reduced binding by 1.75 and 1.36 fold respectively. For 24F.10C12, all selected variants have similar, but slightly reduced, binding compared to the mouse reference (1.13 fold).

TABLE 4

IC50 Values for PD-1, PD-L1 and PD-L2 Composite, human Antibody Sequence Variants

| EH12.2H7 | | 29E.2A3 | | 24F.10C12 | |
| --- | --- | --- | --- | --- | --- |
| Antibody | IC50 μg/ml | Antibody | IC50 μg/ml | Antibody | IC50 μg/ml |
| mouse | 1.23 | mouse | 0.28 | mouse | 0.52 |
| VH3/VK3 | 0.93 | VH2/VK1 | 0.27 | VH2/VK2 | 0.58 |
| VH3/VK4 | 0.74 | VH2/VK2 | 0.49 | VH2/VK3 | 0.59 |
| VH4/VK3 | 0.57 | VH4/VK2 | 0.38 | VH4/VK2 | 0.60 |
| VH4/VK4 | 0.91 | VH2/VK4 | 0.29 | VH4/VK4 | 0.58 |

As a result of these experiments, composite, human antibodies specific for human PD-1, PD-L1 and PD-L2 have been constructed from amino acid sequence segments derived entirely from unrelated human antibody variable regions. All CDR and framework regions in the composite, human antibody variants comprised more than one unrelated human sequence segment (sourced from the human sequence database), and all composite, human antibodies were designed specifically to avoid T cell epitopes. Four lead candidates were initially selected for binding to human PD-1, PD-L1 or PD-L2 and, upon subsequent analysis, were demonstrated to have binding within two-fold of the murine antibody.

Example 3: Enhanced Stimulation of T Cell Activation by Inhibition of PD-1:PD-Ligand Interaction The PD-1 signaling pathway inhibits moderate TCR/CD28 costimulatory signals, with cytokine production being reduced first without a decrease in T cell proliferation. As the TCR/CD28 costimulatory signals weaken, the PD-1 pathway dominates, with a great reduction in cytokine production accompanied by a reduction in proliferation. Accordingly, in order to confirm that the inhibition of the PD-1 pathway via inhibition of the interaction with PD-L1 or PD-L2 using composite, human antibodies of the invention enhances T cell activation, mixed lymphocyte reactions (MLRs) are performed.

Immature myeloid dendritic cells are isolated by culturing human peripheral blood monocytes in IL-4 and GM-CSF. Exposure of immature dendritic cells to an inflammatory cocktail of IL-1β, TNF-α, IL-6, and $PGE_2$ elicits the development of mature dendritic cells that function as APCs. However, the addition of IL-10 to the inflammatory cytokines given during the maturation phase results in APCs that function only 1/6 to 1/3 as well.

T cell activation assays (MLRs) are performed, using IL-10 treated dendritic cells as APCs, in the presence of composite, human antibodies to PD-1, PD-L1 and/or PD-L2, or control antibodies. The addition of anti-PD-1, anti-PD-L1 and/or PD-L2 mAb to cultures of IL-1 0 treated dendritic cells plus allogeneic T cells is predicted to result in an increase in T cell proliferation and cytokine expression, as compared to control IgG treated cultures. A combination of anti-PD-1 antibodies with anti-PD-L1 antibodies, anti-PD-L2 antibodies, may also result in an increase in stimulation greater than that seen with either antibody alone.

Example 4: Inhibition of the PD-1 Pathway in Chronically-Infected Mice

Mice infected with various strains of the lymphocytic choriomeningitis virus (LCMV) are used to study the effect of chronic viral infection on CD8 T cell function. The LCMV Armstrong strain causes an acute infection that is cleared within 8 days, leaving behind a long-lived population of highly functional, resting memory CD8 T cells. The LCMV Cl-13 strain, in contrast, establishes a persistent infection in the host, characterized by a viremia that lasts up to 3 months.

To confirm that blocking the PD-1 signaling restores T cell function and enhances viral control during chronic LCMV infection, the PD-1 signalling is disrupted during chronic LCMV infection using composite, human anti-PD-1 antibodies, anti-PD-L1 antibodies and/or anti-PD-L2 antibodies of the invention. The antibodies are administered every third day to mice infected with LCMV Cl-13 from day 23 to day 37 post-infection. It is expected that at day 37 there will be several-fold more LCMV specific CD8 T cells in treated mice relative to the untreated controls. It is also expected that the induction of proliferation will be specific to CD8 T cells since and the number of CD4 T cells in the spleen will probably be approximately the same in both treated mice and untreated mice.

In addition to an increase in CD8 T cell proliferation, it is expected that the inhibition of PD-1 signaling will also result in an increased production of anti-viral cytokines in virus-specific CD8 T cells. The production of IFN-gamma and TNF-alpha by CD8 T cells will likely be several-fold higher in treated mice as compared to untreated mice. Viral clearance should also be accelerated, and reduced viral titers should be observed in the lung and kidney by day 37 post-infection in treated mice, while untreated mice likely will display significant levels of virus in all these tissues.

CD4 T cells play a key role in the generation and maintenance of CD8 T cell responses. In this regard, CD8 T cells primed in the absence of CD4 T cells are incapable of mounting normal immune responses, and are thus often referred to as "helpless T cells." Furthermore, chronic LCMV infection is more severe in the absence of CD4 T cells. Accordingly, helpless T cells generated during LCMV-Cl-13 infection display an even more profound functional impairment than T cells generated in the presence of CD4 T cells.

CD4 T cells are depleted at the time of LCMV-Cl-13 infection and mice are treated with composite, human anti-PD-1 antibodies, anti-PD-L1 antibodies and/or anti-PD-L1 antibodies of the present invention from day 46 to day 60 post-infection. It is expected that following treatment, treated mice likely will have several-fold more LCMV-specific CD8T cells in their spleen than untreated control mice. This increase in virus-specific CD8 T cells in treated mice likely will be the result to an increase in proliferation, as detected by BrdU incorporation. BrdU analysis is performed by introducing 1 mg/ml BrdU in the drinking water during treatment and staining is performed according to the manufacturer's protocol (BD Biosciences, San Diego, Calif.).

To confirm that the inhibition of PD-1 signals increases the lytic activity of helpless, exhausted, virus-specific CD8 T cells, ex vivo lytic activity of virus-specific CD8 T cells is detected following treatment using a $^{51}Cr$ release assay (Wherry et al., 2003. J. Virol. 77:4911-27). Viral titers are expected to be reduced by several-fold in the spleen, liver, lung, and serum after 2 weeks of treatment relative to untreated mice.

Example 5: Administration of a Vaccine with an Inhibitor of PD-1 Signaling

One approach for boosting T cell responses during a persistent infection is therapeutic vaccination. The rationale for this approach is that endogenous antigens may not be presented in an optimal or immunogenic manner during chronic viral infection and that providing antigen in the form of a vaccine may provide a more effective stimulus for virus-specific T and B cells. Using the chronic LCMV model, mice are administered a recombinant vaccinia virus expressing the LCMV GP33 epitope as a therapeutic vaccine (VVGP33), which results in a modest enhancement of CD8 T cell responses in some chronically infected mice. This therapeutic vaccination is combined with composite, human anti-PD-1 antibodies, anti-PD-L1 antibodies and/or anti-PD-L2 antibodies of the invention. It is expected that LCMV specific T cell responses will be boosted to a greater level than compared to either treatment alone and the effect of combined treatment will likely be more than additive.

Example 6: Chimpanzees as a Model for Immunotherapy of Persistent HCV Infection Chimpanzees provide a model of HCV persistence in humans. Defects in T cell immunity leading to life-long virus persistence both include a deficit in HCV-specific CD4 helper T cells and impaired or altered CD8 effector T cell activity. Persistently infected chimpanzees are treated with composite, human anti-PD-1 antibodies, anti-PD-L1 antibodies and/or anti-PD-L2 antibodies of the invention. The efficacy of blockade of the inhibitory pathways, combined with vaccination using recombinant structural and non-structural HCV proteins, and whether such strategies can enhance the frequency and longevity of virus-specific memory T cells are determined. The defect in T cell immunity is exclusively HCV-specific in persistently infected humans and chimpanzees. Antiviral activity may then be restored by delivering to chimpanzees humanized monoclonal antibodies that block signaling through these molecules.

Persistently infected chimpanzees are treated with composite, human anti-PD-1 antibodies, anti-PD-L1 antibodies and/or anti-PD-L2 antibodies of the invention. After treatment with antibodies, the humoral and cellular immune responses as well as the HCV RNA load are determined. Samples are collected at weeks 1, 2, 3, 5, and 8, and then at monthly intervals. Samples include: 1) serum for analysis of transaminases, autoantibodies, neutralizing antibodies to HCV, and cytokine responses, 2) plasma for viral load and genome evolution, 3) PBMC for in vitro measures of immunity, costimulatory/inhibitory receptor expression and function, 4) fresh (unfixed) liver for isolation of intrahepatic lymphocytes and RNA, and 5) fixed (formalin/paraffin embedded) liver for histology and immunohistochemical analysis. Regional lymph nodes are also collected at 2 or 3 time points to assess expression of co-inhibitory molecules and splice variants by immunohistochemistry and molecular techniques.

To determine if vaccination with HCV antigens potentiates the therapeutic effect of the antibodies, chimpazees are treated as follows: 1) intramuscular immunization with recombinant envelope glycoproteins E1 and E2 (in MF59 adjuvant) and other proteins (core plus NS 3, 4, and 5 formulated with ISCOMS) at weeks 0, 4, and 24; 2) intramuscular immunization with the vaccine used in, but co-administered with composite, human anti-PD-1 antibodies, anti-PD-L1 antibodies and/or anti-PD-L2 antibodies of the invention antibodies. HCV-specific T and B cell responses are monitored at monthly intervals after immunization for a period of 1 year.

Markers examined on HCV-tetramer positive and total T cells in this analysis include markers of differentiation (e.g. CD45RA/RO, CD62L, CCR7, and CD27), activation (e.g. CD25, CD69, CD38, and HLA-DR), survival/proliferation (e.g. bcl-2 and Ki67), cytotoxic potential (e.g. granzymes and perforin), and cytokine receptors (CD122 and CD127). An interesting correlation exists between pre-therapy levels of the chemokine IP-10 and response to PEG IFN-.gamma./ribavirin. IP-10 levels are measured to investigate a potential correlation between negative regulatory pathways or HCV-specific T cell responses and IP-10 levels. Expression of inhibitory receptors and ligands on PBMC are performed by flow cytometry.

Example 7: Enhancing SIV-Specific Immunity In Vivo by PD-1 Blockade

Immune restoration potential of blockade of PD-1 during chronic simian immunodeficiency virus (SIV) infection was tested in macaques. Fourteen Indian rhesus macaques (*Macaca mulatta*) infected with SIV were studied. Eight macaques were used for the early chronic phase and were infected intravenously with 200 50% tissue culture infectious dose ($TCID_{50}$) of SIV251. Six macaques were used for the late chronic phase, three were infected with SIV251 intrarectally and three were infected with SIV239 intravenously. All macaques, except RDb11, were negative for Mamu B08 and Mamu B17 alleles. RDb11 was positive for Mamu B17 allele.

In vivo antibody treatment: Macaques were infused with either partially humanized mouse anti-human PD-1 antibody (clone EH12-1540) (Dorfman et al., Am. J. Surg. Pathol. 30:802-810, 2006) or a control antibody (SYNAGIS). The anti-PD-1 antibody has mouse variable heavy chain domain linked to human IgG1 (mutated to reduce FcR and complement binding) and mouse variable light chain domain linked to human κ. The clone EH12 binds to macaque PD-1 and blocks interactions between PD-1 and its ligands in vitro. SYNAGIS is a humanized mouse monoclonal antibody (IgG1κ) specific to F protein of respiratory syncytial virus. Antibodies were administered intravenously at 3 mg kg$^{-1}$ of body weight on days 0, 3, 7 and 10.

Immune responses: Peripheral blood mononuclear cells from blood and lymphocytes from rectal pinch biopsies were isolated as described previously (Velu et al., J. Virol. 81:5819-5828, 2007). Tetramer staining, intracellular cytokine production, and measurements of anti-SIV Env binding antibody were performed as described previously (Amara et al, Science 292:69-74, 2001; Kannanganat et al., J. Virol. 81:8468-8476, 2007; Lai et al., Virology 369:153-167, 2007).

PD-1 blockade was performed during the early (10 weeks) as well as late (about 90 weeks) phases of chronic SIV infection. Nine macaques (five during the early phase and four during the late phase) received the anti-PD-1 antibody and five macaques (three during the early phase and two during the late phase) received an isotype control antibody (Synagis, anti-respiratory syncytial virus (RSV)-specific).

PD-1 blockade during chronic SIV infection resulted in a rapid expansion of SIV-specific CD8 T cells in the blood of all macaques. The CD8 T-cell responses to two immunodominant epitopes, Gag CM9 (Allen et al., J. Immunol. 160:6062-6071, 1998) and Tat SL8/TL8 (Allen et al., Nature 407:386-390, 2000), were studied using major histocompatibility complex (MHC) I tetrameric complexes in seven of the anti-PD-1-antibody-treated and three of the control-antibody-treated macaques that expressed the Mamu A*01 histocompatibility molecule. Most (>98%) of the Gag-CM9 tetramer-specific CD8 T cells expressed PD-1 before blockade. After PD-1 blockade, the Gag-CM9 tetramer-specific CD8 T cells expanded rapidly and peaked by 7-21 days. At the peak response, these levels were about 2.5 to 11-fold higher than their respective levels on day 0 (P=0.007) and remained elevated until 28-45 days. Similar results were observed with blockade during the early as well as late phases of chronic SIV infection. A 3-4-fold increase in the frequency of Gag-specific interferon (IFN)-γ-positive CD8 T cells was also observed by day 14 after blockade in the two Mamu A*01-negative animals (RTd11 and RDb11), demonstrating that PD-1 blockade can enhance the frequency of virus-specific CD8 T cells that are restricted by non-Mamu A*01 alleles. Expansion of SIV-specific CD8 T cells was not observed in the control-antibody treated macaques.

PD-1 blockade was also associated with a significant increase in the frequency of virus-specific CD8 T cells that were undergoing active cell division in vivo with improved functional quality. Consistent with the rapid expansion of SIV-specific CD8 T cells, the frequency of Gag-CM9 tetramer-specific CD8 cells that co-expressed Ki67 (marker for proliferating cells) also increased as early as by day 7 after blockade (P=0.01). Similarly, we observed an increase in the frequencies of Gag-CM9 tetramer-specific CD8 T cells co-expressing perforin and granzyme B (cytolytic potential; P=0.001 and P=0.03, respectively), CD28 (co-stimulation potential; P=0.001), CD127 (proliferative potential; P=0.0003) and CCR7 (lymph-node homing potential; 0.001). A transient 1.5 to 2-fold increase in the frequency of tetramer-negative and Ki67-positive CD8 T cells after blockade was observed. This could be due to expansion of CD8 T cells specific to other epitopes in Gag as well as other proteins of SIV, and other chronic viral infections in these animals. No significant enhancement was observed for these markers in the three control antibody-treated macaques.

No expansion was observed for Tat-TL8-specific CD8 T cells after blockade. This could be due to viral escape from recognition by Tat-TL8-specific CD8 T cells, as PD-1 blockade is known to result in expansion of T cells only when they simultaneously receive signals through T-cell receptor. To test this possibility, the viral genomes present in the plasma just before the initiation of blockade from all three Mamu A*01-positive macaques that were infected with SIV251 and received the blocking antibody during the early phase of infection were sequenced. Indeed, mutations in the viral genome corresponding to the Tat TL8 epitope region were found. All these mutations either have been shown or predicted to reduce the binding of Tat SL8/TL8 peptide to Mamu A*01 MHC molecule and result in escape from recognition by the Tat-SL8/TL8-specific CD8 T cells". These results suggest that in vivo blockade of PD-1 may not result in expansion of T cells that are specific to escape mutants of viral epitopes.

PD-1 blockade also resulted in expansion of Gag-CM9-specific CD8 T cells at the colorectal mucosal tissue (gut), a preferential site of SIV/HIV replication. Expansion was not observed for two of the seven macaques, although expansion was evident for one of them in blood. In contrast to blood, the expansion in gut peaked much later by day 42 and ranged from 2- to 3-fold compared with their respective day 0 levels (P=0.003). Similar to blood, the Gag-CM9 tetramer-specific cells that co-expressed Ki67 (P=0.01), perforin (P=0.03), granzyme B (P=0.01) and CD28 (P=0.01) also increased in the gut after blockade.

More importantly, PD-1 blockade also enhanced the functional quality of anti-viral CD8 T cells and resulted in the generation of polyfunctional cells capable of co-producing the cytokines IFN-$\gamma$, tumour-necrosis factor (TNF)-$\alpha$ and interleukin (IL)-2. On the day of initiation of PD-1 blockade during the late chronic phase of infection, the frequency of Gag-specific IFN-$\gamma$-positive cells was low and they failed to co-express TNF-$\alpha$ and IL-2. However, after the blockade, the frequency of IFN-$\gamma$-positive cells increased in all four PD-1 antibody-treated macaques (P=0.03) and they acquired the ability to co-express TNF-$\alpha$ and IL-2. The expansion of IFN-$\gamma$ positive cells peaked by 14-21 days and the peak levels were 2-10-fold higher than the respective day 0 levels. On day 21, about 16% of the total Gag-specific cells co-expressed all three cytokines, and about 30% co-expressed IFN-$\gamma$ and TNF-$\alpha$. This is in contrast to <1% of the total Gag-specific cells co-expressing all three cytokines (P=0.01), and about 14% co-expressing IFN-$\gamma$ and TNF-$\alpha$ on day 0 (P=0.04). Similar results were also observed after blockade during the early chronic phase of infection.

To test the role of PD-1 in regulating B-cell function during chronic immunodeficiency virus infections, the B-cell responses after PD-1 blockade in SIV-infected macaques were characterized. Analysis of PD-1 expression on different B-cell subsets before PD-1 blockade revealed preferential expression of PD-1 by memory B cells ($CD20^+CD27^+CD21^-$) compared to naive B cells ($CD20^+CD27^-CD21^+$; P<0.001). In vivo blockade of PD-1 resulted in a 2 to 8-fold increase in the titer of SIV-specific binding antibody by day 28 after blockade (P<0.001). To understand this further, experiments were carried out to the proliferation of memory B cells in SIV-infected macaques that were treated simultaneously with anti-PD-1 antibody and anti-retroviral therapy and observed a significant increase in Ki67+ (proliferating) memory, but not naive, B cells as early as day 3. These results demonstrate that the PD-1-PDL pathway could have a role in regulating B-cell dysfunction during chronic SIV infection.

Neutralization assays revealed a two-fold increase in titers against the easily neutralizable laboratory-adapted SIV251 and no increase in titers against hard-to-neutralize wild-type SIV251 or SIV239. In two of the nine animals treated with anti-PD-1 antibody, only a minimal (<2-fold) expansion of SIV-specific antibody after blockade. Notably, the frequency of total memory B cells in these two animals was lower (~40% of total B cells) compared with the remaining seven animals (60-90% of total B cells) before blockade, indicating that the level of SIV-specific memory B cells before blockade may determine the level of expansion of SIV-specific antibody after blockade.

PD-1 blockade resulted in significant reductions in plasma viraemia (P=0.03) and also prolonged the survival of SIV-infected macaques (P=0.001). In two of the five macaques treated with anti-PD-1 antibody during the early chronic phase, viral load declined by day 10 and persisted at or below this level until day 90. In one macaque viral load declined transiently and in the remaining two macaques increased transiently and returned to pre-blockade levels. In contrast to the early chronic phase, all four macaques treated with the anti-PD-1 antibody during the late chronic phase showed a transient increase in viraemia by day 7, but rapidly reduced the virus load by day 21 to levels that were below their respective day 0 levels. However, the viral RNA levels returned to pre-blockade levels by day 43. As expected, no significant reductions in the plasma viral loads were observed in any of the five macaques treated with the control antibody. By 21-28 days after blockade, the viral RNA levels in the anti-PD-1-antibody-treated animals were 2-10-fold lower than their respective day 0 levels (P=0.03). By day 150 after the blockade, four of the five macaques in the control group were killed owing to AIDS-related symptoms (for example loss of appetite, diarrhoea, weight loss), whereas all nine animals in the anti-PD-1-antibody-treated group had survived (P=0.001).

The observed initial rise in plasma viraemia levels in all of the late phase-treated and some of the early-phase-treated animals could be due to an increase in the frequency of activated CD4 T cells. To determine this, the percentage of Ki67-positive total CD4 T cells as well as the frequency of SIV Gag-specific IFN-$\gamma$ producing CD4 T cells (preferential targets for virus replication") after blockade were measured. These analyses revealed a transient increase in the percentage of Ki67-positive CD4 T cells by day 7-14 after blockade (P=0.002) and this increase was higher in animals treated during the late phase than early phase of infection (P=0.015). Similarly, an increase in the frequency of Gag-specific CD4 T cells was also observed, but only in animals treated during the late phase of infection. No significant increases were observed for these activated CD4 T cells in the control-antibody-treated macaques. These results suggest that the activated CD4 T cells could have contributed to the observed initial rise in plasma viraemia levels after blockade.

Before initiation of PD-1 blockade, the set point viral load in plasma and total CD4 T cells in blood and gut were similar between the anti-PD-1-antibody-treated and control-antibody treated groups. However, the frequencies of Gag CM9+ cells and Gag CM9+ cells co-expressing perforin, granzyme B or CD28 were not similar between the two treatment groups before in vivo blockade. This raises the possibility that these differences could have contributed to the expansion of Gag CM9+ cells after PD-1 blockade. To study the influence of the frequency of Gag CM9+ cells before blockade on their expansion after blockade, the anti-PD-1-antibody-treated group into was divided into two subgroups based on the frequency of Gag CM9+ cells before initiation of blockade such that one group has similar levels and the other group has higher levels of Gag CM9+ cells compared with the control-antibody-treated group. These subgroups were then analyzed for expansion of Gag CM9+ cells after blockade. Expansion of Gag CM9+ cells was evident in both subgroups of animals after blockade of PD-1, irrespective of whether they were at low or high levels before blockade. Similar results were also observed with subgroup analyses based on the frequency of Gag CM9+ cells co-expressing molecules associated with better T-cell function such as perforin, granzyme B, CCR7, CD 127 or CD28. However, a trend towards better expansion of Gag CM9+CD28+ cells in animals with higher levels of Gag CM9+CD28+ cells before blockade was observed, suggesting that CD28 expression may serve as a biomarker for predicting the outcome of in vivo PD-1 blockade.

The experiments described above demonstrate that PD-1 blockade using an antibody to PD-1 results in rapid expansion of virus-specific CD8 T cells with improved functional quality. This enhanced T-cell immunity was seen in the blood and also in the gut, a major reservoir of SIV infection.

PD-1 blockade also resulted in proliferation of memory B cells and increases in SIV envelope-specific antibody. These improved immune responses were associated with significant reductions in plasma viral load and also prolonged the survival of SIV-infected macaques. Blockade was effective during the early (week 10) as well as late (~week 90) phases of chronic infection even under conditions of severe lymphopenia. These results demonstrate enhancement of both cellular and humoral immune responses during a pathogenic immunodeficiency virus infection by blocking a single inhibitory pathway and identify a novel therapeutic approach for control of human immunodeficiency virus infections.

Example 8: Enhanced Proliferation of SIV-Specific CD8 T Cells Following In Vitro Blockade of the PD-1:PDL Pathway by a Humanized PD-1 Antibody and a Humanized PD-L1 Antibody Effect of a humanized anti-PD-1 antibody derived from EH-12.2H7 and a humanized anti-PD-L1 antibody derived from 29E.2A3 on the proliferative capacity of SIV Gag-specific CD8 T cells was tested in vitro. The humanized anti-PD-1 antibody has the heavy chain variable region sequence of SEQ ID NO:28, and the light chain variable region sequence of SEQ ID NO:32. The humanized anti-PD-L1 antibody has the heavy chain variable region sequence of SEQ ID NO:35, and the light chain variable region sequence of SEQ ID NO:42. The heavy chain constant region of the humanized antibodies is from human IgG4 with Ser 228 to Pro mutation (from CPSCP to CPPCP) so that the antibody forms dimers, and the light chain constant region is human kappa light chain constant region. The amino acid numbering for Ser 228 is according to the EU numbering system. See Aalberse et al., *Immunology* 105:9-19, 2002. PBMC obtained from SIV-infected macaques (between 3 months to 1.5 years after infection) were stained with carboxyfluorescein diacetate succinimidyl ester (CFSE) and stimulated either with SIV Gag peptide pool or culture medium for 6 days in the presence or absence of a blocking antibody. At the end of stimulation, cells were stained for surface CD3 and CD8, and intracellular Ki-67. Cells were then acquired on a FACS Calibur and analyzed using Flowjo software. Lymphocytes were identified based on the scatter, then CD8 T cells (CD3+, CD8+) were analyzed for co-staining for Ki-67 and CFSE. Ki-67+, CFSE low cells were identified as proliferating cells.

Figure 14B:
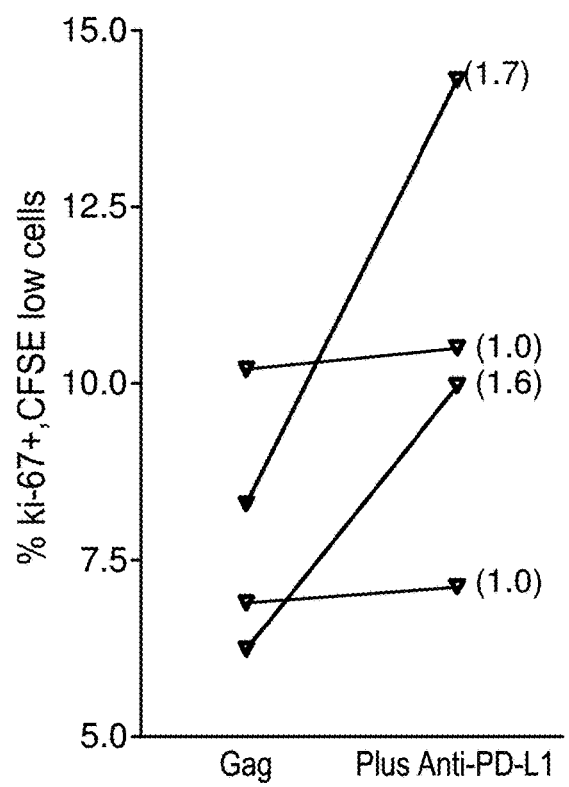

As shown in FIG. 14A, in vitro blockade of PD-1:PD-1 ligand pathway using the anti-PD-1 Ab results in a significant increase in proliferation of SIV-specific CD8 T cells responses. In vitro blockade using the anti-PD-L1 Ab results in a modest increase in proliferation of SIV-specific CD8 T cells responses (FIG. 14B).

Example 9: Restoration of HCV-Specific T Cell Proliferation by Intrahepatic Mononuclear Cells from a Persistently Infected Chimpanzee CFSE-labeled intrahepatic lymphocytes ($2 \times 10^6$) were isolated from chimpanzee 1564 that had been chronically infected with the genotype 1a H77 strain of HCV for more than 10 years. The intrahepatic lymphocytes were co-cultured for 6 days with $4 \times 10^6$ irradiated autologous CD8-depleted PBMC that were either unmanipulated or pulsed with overlapping peptides spanning the entire HCV polyprotein (genotype 1a H77 strain). Cells were cultured in RPMI media supplemented with L-glutamine and 10% FCS, with and without an anti-PD-L1 blocking antibody (10 µg/ml, added at day 0 and day 2). The humanized anti-PD-L1 antibody has the heavy chain variable region sequence of SEQ ID NO:35, and the light chain variable region sequence of SEQ ID NO:42. The heavy chain constant region of the humanized antibodies is from human IgG4 with Ser 228 to Pro mutation (from CPSCP to CPPCP) so that the antibody forms dimers, and the light chain constant region is human kappa light chain constant region. The amino acid numbering for Ser 228 is according to the EU numbering system. See Aalberse et al., *Immunology* 105:9-19, 2002. On day 6, cells were stained with CD8-PerCP, A0701/P7(758)-PE tetramer, PD-1-Alexa 647, CD4-Alexa 700, CD14-Alexa 700, CD16-Alexa 700, CD19-Alexa 700, and Live/Dead Blue. Samples were acquired on a BD LSR II flow cytometer, and data was analyzed using FlowJo software.

Figure 15:
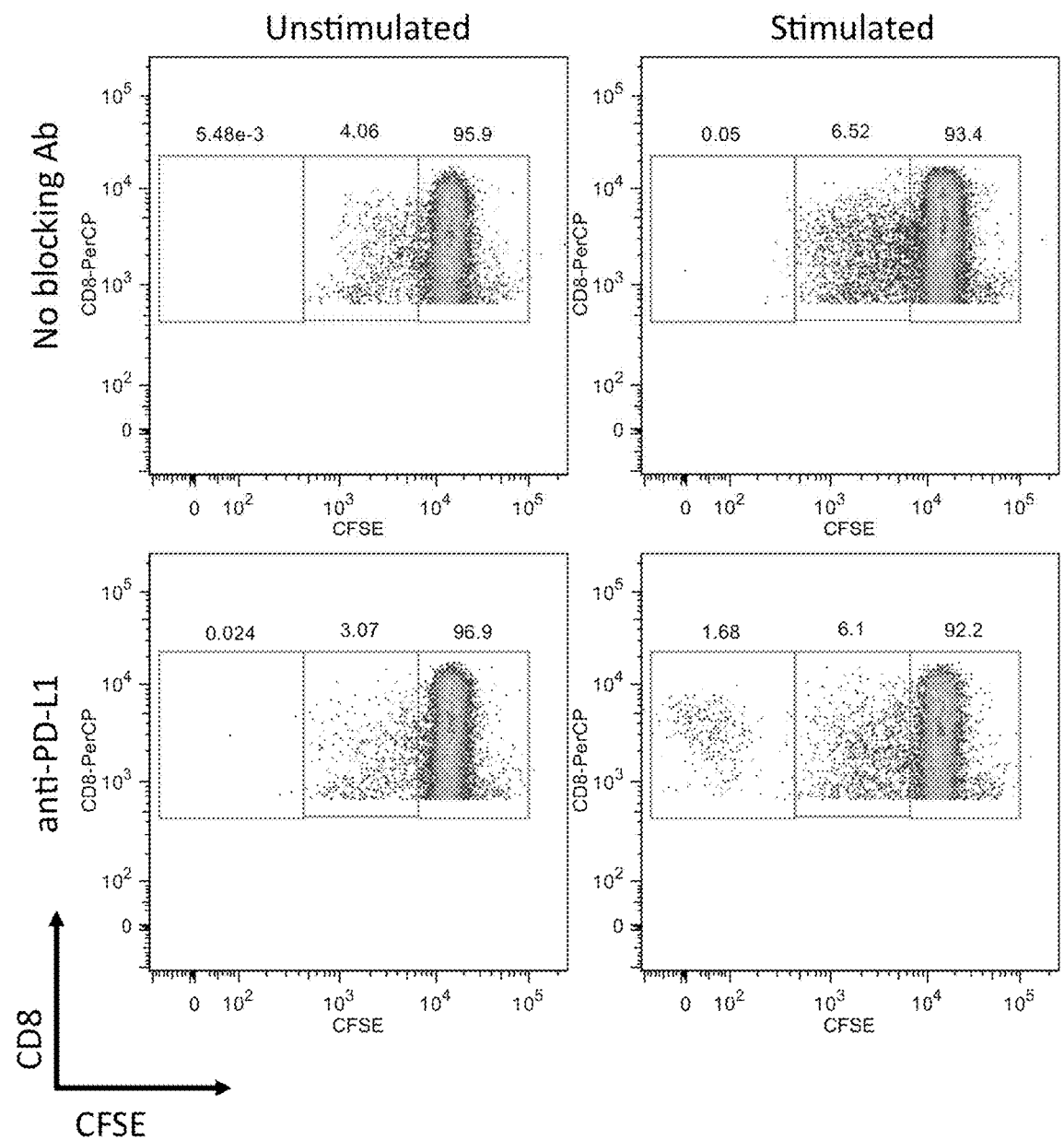
FIG. 15 shows that PD-L1 blockage restores antigen-driven proliferation of intrahepatic CD8 T cells (representative data from animal 1564).

As shown in FIG. 15, the anti-PD-L1 antibody treatment restored HCV-specific T cell proliferation by intrahepatic mononuclear cells from a persistently infected chimpanzee.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject suffering from cancer, comprising administering to the subject an effective amount of a composition comprising an isolated antibody or antigen-binding fragment thereof, wherein the isolated antibody or antigen-binding fragment thereof comprises:
   a) a heavy chain variable region sequence comprising three CDRs with the sequences of SEQ ID NOs: 13-15; and/or
   b) a light chain variable region sequence comprising three CDRs with the sequences of SEQ ID NOs: 16-18,
wherein the isolated antibody or antigen-binding fragment thereof binds to a PD-L1 protein comprising the amino acid sequence of SEQ ID NO: 4, and wherein the isolated antibody or antigen-binding fragment thereof is chimeric, humanized, composite, or human.

2. The method of claim 1, wherein the cancer is selected from the group consisting of a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, and thyroid cancer.

3. A method of treating a subject suffering from a cancer over-expressing PD-L1, comprising administering to the subject an effective amount of a composition comprising an isolated antibody or antigen-binding fragment thereof, wherein the isolated antibody or antigen-binding fragment thereof comprises:
   a) a heavy chain variable region sequence comprising three CDRs with the sequences of SEQ ID NOs: 13-15; and/or
   b) a light chain variable region sequence comprising three CDRs with the sequences of SEQ ID NOs: 16-18,
wherein the isolated antibody or antigen-binding fragment thereof binds to a PD-L1 protein comprising the amino acid sequence of SEQ ID NO: 4, and wherein the isolated antibody or antigen-binding fragment thereof is chimeric, humanized, composite, or human.

4. The method of claim 3, wherein the antibody is modified to increase antibody-induced cytotoxicity.

5. The method of claim 4, wherein the antibody is conjugated to an agent selected from the group consisting of a toxin and an imaging agent.

6. The method of claim 1, wherein the isolated antibody or antigen-binding fragment thereof comprises:
   a) a heavy chain variable region sequence comprising three CDRs with the sequences of SEQ ID NOs: 13-15; and
   b) a light chain variable region sequence comprising three CDRs with the sequences of SEQ ID NOs: 16-18.

7. The method of claim 6, wherein the isolated antibody or antigen-binding fragment thereof comprises:
   a) a heavy chain variable region sequence selected from the group consisting of SEQ ID NOs: 34-38, or a sequence with at least about 95% homology to a heavy chain variable region sequence selected from the group consisting of SEQ ID NOs: 34-38; and
   b) a light chain variable region sequence selected from the group consisting of SEQ ID NOs: 39-42, or a sequence with at least about 95% homology to a light chain variable region sequence selected from the group consisting of SEQ ID NOs: 39-42.

8. The method of claim 1, wherein the isolated antibody or antigen-binding fragment thereof comprises:
   a) a heavy chain variable region sequence selected from the group consisting of SEQ ID NOs: 34-38; and
   b) a light chain variable region sequence selected from the group consisting of SEQ ID NOs: 39-42.

9. The method of claim 8, wherein the isolated antibody or antigen-binding fragment thereof comprises:
   a) a heavy chain variable region sequence comprising SEQ ID NO: 35 or 37; and
   b) a light chain variable region sequence comprising SEQ ID NO: 39, 40, or 42.

10. The method of claim 6, wherein the isolated antibody or antigen-binding fragment comprises:
   a) a heavy chain variable region sequence comprising SEQ ID NO: 35 or 37, or a sequence with at least about 95% homology to a heavy chain variable region sequence comprising SEQ ID NO: 35 or 37; and
   b) a light chain variable region sequence comprising SEQ ID NO: 39, 40 or 42, or a sequence with at least about 95% homology to a light chain variable region sequence comprising SEQ ID NO: 39, 40 or 42.

11. The method of claim 1, wherein the isolated antibody or antigen-binding fragment thereof inhibits the binding of an antibody comprising a heavy chain variable region comprising the sequence of SEQ ID NO: 78 and a light chain variable region comprising the sequence of SEQ ID NO: 79 to Fc-PD-L1.

12. The method of claim 1, wherein the isolated antibody or antigen-binding fragment thereof inhibits a PD-L1-mediated signal.

13. The method of claim 3, wherein the isolated antibody or antigen-binding fragment thereof comprises:
   a) a heavy chain variable region sequence comprising three CDRs with the sequences of SEQ ID NOs: 13-15; and
   b) a light chain variable region sequence comprising three CDRs with the sequences of SEQ ID NOs: 16-18.

14. The method of claim 13, wherein the isolated antibody or antigen-binding fragment thereof comprises:
   a) a heavy chain variable region sequence selected from the group consisting of SEQ ID NOs: 34-38, or a sequence with at least about 95% homology to a heavy chain variable region sequence selected from the group consisting of SEQ ID NOs: 34-38; and
   b) a light chain variable region sequence selected from the group consisting of SEQ ID NOs: 39-42, or a sequence with at least about 95% homology to a light chain variable region sequence selected from the group consisting of SEQ ID NOs: 39-42.

15. The method of claim 3, wherein the isolated antibody or antigen-binding fragment thereof comprises:
   a) a heavy chain variable region sequence selected from the group consisting of SEQ ID NOs: 34-38; and
   b) a light chain variable region sequence selected from the group consisting of SEQ ID NOs: 39-42.

16. The method of claim 15, wherein the isolated antibody or antigen-binding fragment thereof comprises:
   a) a heavy chain variable region sequence comprising SEQ ID NO: 35 or 37; and
   b) a light chain variable region sequence comprising SEQ ID NO: 39, 40, or 42.

17. The method of claim 13, wherein the isolated antibody or antigen-binding fragment comprises:
   a) a heavy chain variable region sequence comprising SEQ ID NO: 35 or 37, or a sequence with at least about 95% homology to a heavy chain variable region sequence comprising SEQ ID NO: 35 or 37; and
   b) a light chain variable region sequence comprising SEQ ID NO: 39, 40 or 42, or a sequence with at least about 95% homology to a light chain variable region sequence comprising SEQ ID NO: 39, 40 or 42.

18. The method of claim 3, wherein the isolated antibody or antigen-binding fragment thereof inhibits the binding of an antibody comprising a heavy chain variable region comprising the sequence of SEQ ID NO: 78 and a light chain variable region comprising the sequence of SEQ ID NO: 79 to Fc-PD-L1.

19. The method of claim 3, wherein the isolated antibody or antigen-binding fragment thereof inhibits a PD-L1-mediated signal.

\* \* \* \* \*

SEQUENCE LISTING

<160> NUMBER OF SEQ ID NOS: 158

<210> SEQ ID NO 1
<211> LENGTH: 363
<212> TYPE: DNA
<213> ORGANISM: Artificial Sequence
<220> FEATURE:
<223> OTHER INFORMATION: Synthetic Construct

<400> SEQUENCE: 1

```
caggtccagc ttgtgcagtc tggggctgaa ctgaaacagc ctggggcctc agtgaagatg      60
tcctgcaagg cttctggcta cagttttact agctcctgga tacactgggt gaaacaggct     120
cctggacagg gtctggaatg gattggatac atttatccta gcactggttt tactgagtac     180
aatcagaagt tcaaggacag ggccacattg actgcagaca atccaccag cacagcctac      240 atggaactga gcagcctgag atctgaggac tctgcagtct attactgtgc aagatggagg     300
gacagctcgg gctaccatgc tatggactac tggggtcaag gaacctcagt caccgtctcc     360
tca                                                                  363
```

<210> SEQ ID NO 2
<211> LENGTH: 288
<212> TYPE: PRT
<213> ORGANISM: Homo sapiens

<400> SEQUENCE: 2

| Met<br>1 | Gln | Ile | Pro | Gln<br>5 | Ala | Pro | Trp | Pro | Val<br>10 | Val | Trp | Ala | Val | Leu<br>15 | Gln |
|---|---|---|---|---|---|---|---|---|---|---|---|---|---|---|---|
| Leu | Gly | Trp | Arg<br>20 | Pro | Gly | Trp | Phe | Leu<br>25 | Asp | Ser | Pro | Asp | Arg<br>30 | Pro | Trp |
| Asn | Pro | Pro<br>35 | Thr | Phe | Ser | Pro | Ala<br>40 | Leu | Leu | Val | Val | Thr<br>45 | Glu | Gly | Asp |
| Asn | Ala<br>50 | Thr | Phe | Thr | Cys | Ser<br>55 | Phe | Ser | Asn | Thr | Ser<br>60 | Glu | Ser | Phe | Val |
| Leu<br>65 | Asn | Trp | Tyr | Arg | Met<br>70 | Ser | Pro | Ser | Asn | Gln<br>75 | Thr | Asp | Lys | Leu | Ala<br>80 |
| Ala | Phe | Pro | Glu | Asp<br>85 | Arg | Ser | Gln | Pro | Gly<br>90 | Gln | Asp | Cys | Arg | Phe<br>95 | Arg |
| Val | Thr | Gln | Leu<br>100 | Pro | Asn | Gly | Arg | Asp<br>105 | Phe | His | Met | Ser | Val<br>110 | Val | Arg |
| Ala | Arg | Arg<br>115 | Asn | Asp | Ser | Gly | Thr<br>120 | Tyr | Leu | Cys | Gly | Ala<br>125 | Ile | Ser | Leu |
| Ala | Pro<br>130 | Lys | Ala | Gln | Ile | Lys<br>135 | Glu | Ser | Leu | Arg | Ala<br>140 | Glu | Leu | Arg | Val |
| Thr<br>145 | Glu | Arg | Arg | Ala | Glu<br>150 | Val | Pro | Thr | Ala | His<br>155 | Pro | Ser | Pro | Ser | Pro<br>160 |
| Arg | Pro | Ala | Gly | Gln<br>165 | Phe | Gln | Thr | Leu | Val<br>170 | Val | Gly | Val | Val | Gly<br>175 | Gly |
| Leu | Leu | Gly | Ser<br>180 | Leu | Val | Leu | Leu | Val<br>185 | Trp | Val | Leu | Ala | Val<br>190 | Ile | Cys |
| Ser | Arg | Ala<br>195 | Ala | Arg | Gly | Thr | Ile<br>200 | Gly | Ala | Arg | Arg | Thr<br>205 | Gly | Gln | Pro |
| Leu | Lys<br>210 | Glu | Asp | Pro | Ser | Ala<br>215 | Val | Pro | Val | Phe | Ser<br>220 | Val | Asp | Tyr | Gly |
| Glu<br>225 | Leu | Asp | Phe | Gln | Trp<br>230 | Arg | Glu | Lys | Thr | Pro<br>235 | Glu | Pro | Pro | Val | Pro<br>240 |
| Cys | Val | Pro | Glu | Gln<br>245 | Thr | Glu | Tyr | Ala | Thr<br>250 | Ile | Val | Phe | Pro | Ser<br>255 | Gly |
| Met | Gly | Thr | Ser<br>260 | Ser | Pro | Ala | Arg | Arg<br>265 | Gly | Ser | Ala | Asp | Gly<br>270 | Pro | Arg |
| Ser | Ala | Gln<br>275 | Pro | Leu | Arg | Pro | Glu<br>280 | Asp | Gly | His | Cys | Ser<br>285 | Trp | Pro | Leu |

```
<210> SEQ ID NO 3
<211> LENGTH: 363
<212> TYPE: DNA
<213> ORGANISM: Artificial Sequence
<220> FEATURE:
<223> OTHER INFORMATION: Synthetic Construct

<400> SEQUENCE: 3
caggtccagc ttgtgcagtc tggggctgaa gtgaaacagc ctggggcctc agtgaagatg      60
tcctgcaagg cttctggcta cagttttact agctcctgga tacactgggt gaaacaggct     120
cctggacagg gtctggaatg gattggatac atttatccta gcactggttt tactgagtac     180
aatcagaagt tcaaggacag gccacattg actgcagaca atccaccag cacagcctac      240 atggaactga gcagcctgag atctgaggac actgcagtct attactgtgc aagatggagg     300
gacagctcgg gctaccatgc tatggactac tggggtcaag gaacctcagt caccgtctcc     360
tca                                                                   363

<210> SEQ ID NO 4
<211> LENGTH: 290
<212> TYPE: PRT
<213> ORGANISM: Homo sapiens

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255
```

```
Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
        275                 280                 285

Glu Thr
    290

<210> SEQ ID NO 5
<211> LENGTH: 363
<212> TYPE: DNA
<213> ORGANISM: Artificial Sequence
<220> FEATURE:
<223> OTHER INFORMATION: Synthetic Construct

<400> SEQUENCE: 5
caggtccagc ttgtgcagtc tggggctgaa gtgaaacagc ctggggcctc agtgaagatg      60
tcctgcaagg cttctggcta cagttttact agctcctgga tacactgggt gaaacaggct     120
cctggacagg gtctggaatg gattggatac atttatccta gcactggttt tactgagtac     180
aatcagaagt tcaaggacag ggccacattg actgcagaca atccaccag cacagcctac      240 atggaactga gcagcctgag atctgaggac actgcagtct attactgtgc aagatggagg     300
gacagctcgg gctaccatgc tatggactac tggggtcaag aaccctggt caccgtctcc      360 tca                                                                   363

<210> SEQ ID NO 6
<211> LENGTH: 273
<212> TYPE: PRT
<213> ORGANISM: Homo sapiens

<400> SEQUENCE: 6

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205
```

Leu Gln Ser Gln Met Glu Pro Arg Thr His Pro Thr Trp Leu Leu His
            210                 215                 220

Ile Phe Ile Pro Phe Cys Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

<210> SEQ ID NO 7
<211> LENGTH: 5
<212> TYPE: PRT
<213> ORGANISM: Mus musculus

<400> SEQUENCE: 7

Ser Ser Trp Ile His
1               5

<210> SEQ ID NO 8
<211> LENGTH: 17
<212> TYPE: PRT
<213> ORGANISM: Mus musculus

<400> SEQUENCE: 8

Tyr Ile Tyr Pro Ser Thr Gly Phe Thr Glu Tyr Asn Gln Lys Phe Lys
1               5                   10                  15

Asp

<210> SEQ ID NO 9
<211> LENGTH: 12
<212> TYPE: PRT
<213> ORGANISM: Mus musculus

<400> SEQUENCE: 9

Trp Arg Asp Ser Ser Gly Tyr His Ala Met Asp Tyr
1               5                   10

<210> SEQ ID NO 10
<211> LENGTH: 15
<212> TYPE: PRT
<213> ORGANISM: Mus musculus

<400> SEQUENCE: 10

Arg Ala Ser Gln Ser Val Ser Thr Ser Gly Tyr Ser Tyr Met His
1               5                   10                  15

<210> SEQ ID NO 11
<211> LENGTH: 7
<212> TYPE: PRT
<213> ORGANISM: Mus musculus

<400> SEQUENCE: 11

Phe Gly Ser Asn Leu Glu Ser
1               5

<210> SEQ ID NO 12
<211> LENGTH: 9
<212> TYPE: PRT
<213> ORGANISM: Mus musculus

<400> SEQUENCE: 12

```
Gln His Ser Trp Glu Ile Pro Tyr Thr
1               5
```

\<210\> SEQ ID NO 13
\<211\> LENGTH: 5
\<212\> TYPE: PRT
\<213\> ORGANISM: Mus musculus

\<400\> SEQUENCE: 13

```
Ser Tyr Val Met His
1               5
```

\<210\> SEQ ID NO 14
\<211\> LENGTH: 17
\<212\> TYPE: PRT
\<213\> ORGANISM: Mus musculus

\<400\> SEQUENCE: 14

```
Tyr Val Asn Pro Phe Asn Asp Gly Thr Lys Tyr Asn Glu Met Phe Lys
1               5                   10                  15
Gly
```

\<210\> SEQ ID NO 15
\<211\> LENGTH: 6
\<212\> TYPE: PRT
\<213\> ORGANISM: Mus musculus

\<400\> SEQUENCE: 15

```
Gln Ala Trp Gly Tyr Pro
1               5
```

\<210\> SEQ ID NO 16
\<211\> LENGTH: 15
\<212\> TYPE: PRT
\<213\> ORGANISM: Mus musculus

\<400\> SEQUENCE: 16

```
Arg Ala Thr Glu Ser Val Glu Tyr Tyr Gly Thr Ser Leu Val Gln
1               5                   10                  15
```

\<210\> SEQ ID NO 17
\<211\> LENGTH: 7
\<212\> TYPE: PRT
\<213\> ORGANISM: Mus musculus

\<400\> SEQUENCE: 17

```
Ala Ala Ser Ser Val Asp Ser
1               5
```

\<210\> SEQ ID NO 18
\<211\> LENGTH: 9
\<212\> TYPE: PRT
\<213\> ORGANISM: Mus musculus

\<400\> SEQUENCE: 18

```
Gln Gln Ser Arg Arg Val Pro Tyr Thr
1               5
```

\<210\> SEQ ID NO 19
\<211\> LENGTH: 5
\<212\> TYPE: PRT
\<213\> ORGANISM: Mus musculus

\<400\> SEQUENCE: 19

```
Gly Tyr Thr Met His
1               5

<210> SEQ ID NO 20
<211> LENGTH: 17
<212> TYPE: PRT
<213> ORGANISM: Mus musculus

<400> SEQUENCE: 20

Tyr Ile Asn Pro Arg Ser Gly Tyr Thr Glu Tyr Asn Gln Lys Phe Lys
1               5                   10                  15

Asp

<210> SEQ ID NO 21
<211> LENGTH: 5
<212> TYPE: PRT
<213> ORGANISM: Mus musculus

<400> SEQUENCE: 21

Pro Trp Phe Ala Tyr
1               5

<210> SEQ ID NO 22
<211> LENGTH: 17
<212> TYPE: PRT
<213> ORGANISM: Mus musculus

<400> SEQUENCE: 22

Lys Ser Ser Gln Ser Leu Leu Asn Ser Gly Asn Gln Lys Asn Tyr Leu
1               5                   10                  15

Thr

<210> SEQ ID NO 23
<211> LENGTH: 7
<212> TYPE: PRT
<213> ORGANISM: Mus musculus

<400> SEQUENCE: 23

Trp Ala Ser Thr Arg Glu Ser
1               5

<210> SEQ ID NO 24
<211> LENGTH: 9
<212> TYPE: PRT
<213> ORGANISM: Mus musculus

<400> SEQUENCE: 24

Gln Asn Asp Tyr Ser Tyr Pro Leu Thr
1               5

<210> SEQ ID NO 25
<211> LENGTH: 121
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Leu Lys Gln Pro Gly Ala
1               5                   10                  15

Ser Val Lys Met Ser Cys Lys Ala Ser Gly Tyr Ser Phe Thr Ser Ser
                20                  25                  30
```

```
Trp Ile His Trp Val Lys Gln Ala Pro Gly Gln Gly Leu Glu Trp Ile
            35                  40                  45

Gly Tyr Ile Tyr Pro Ser Thr Gly Phe Thr Glu Tyr Asn Gln Lys Phe
        50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
        115                 120
```

<210> SEQ ID NO 26
<211> LENGTH: 121
<212> TYPE: PRT
<213> ORGANISM: Artificial Sequence
<220> FEATURE:
<223> OTHER INFORMATION: Synthetic Construct

<400> SEQUENCE: 26

```
Gln Val Gln Leu Val Gln Ser Gly Ala Glu Val Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Ile
            35                  40                  45

Gly Tyr Ile Tyr Pro Ser Thr Gly Phe Thr Glu Tyr Asn Gln Lys Phe
        50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
        115                 120
```

<210> SEQ ID NO 27
<211> LENGTH: 121
<212> TYPE: PRT
<213> ORGANISM: Artificial Sequence
<220> FEATURE:
<223> OTHER INFORMATION: Synthetic Construct

<400> SEQUENCE: 27

```
Gln Val Gln Leu Val Gln Ser Gly His Glu Val Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Ile
            35                  40                  45

Gly Tyr Ile Tyr Pro Ser Thr Gly Phe Thr Glu Tyr Asn Gln Lys Phe
        50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Trp Arg Asp Ser Ser Gly Tyr His Ala Met Asp Tyr Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly His Glu Val Lys Gln Pro Gly Ala
1               5                   10                  15

Ser Val Lys Met Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Arg Asp Ser Ser Gly Tyr His Ala Met Asp Tyr Trp Gly
            100                 105                 110

Gln Gly Thr Leu Val Thr Val Ser Ser
        115                 120

<210> SEQ ID NO 29
<211> LENGTH: 121
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Tyr Ile Tyr Pro Ser Thr Gly Phe Thr Glu Tyr Asn Gln Lys Phe
    50                  55                  60

Lys Asp Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Trp Arg Asp Ser Ser Gly Tyr His Ala Met Asp Tyr Trp Gly
            100                 105                 110

Gln Gly Thr Leu Val Thr Val Ser Ser
        115                 120

<210> SEQ ID NO 30
<211> LENGTH: 111
<212> TYPE: PRT

<213> ORGANISM: Artificial Sequence
<220> FEATURE:
<223> OTHER INFORMATION: Synthetic Construct

<400> SEQUENCE: 30

Asp Ile Val Leu Thr Gln Ser Pro Ala Ser Leu Thr Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Thr Tyr Tyr Cys Gln His Ser Trp
                85                  90                  95

Glu Ile Pro Tyr Thr Phe Gly Gln Gly Thr Lys Leu Glu Ile Lys
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Synthetic Construct

<400> SEQUENCE: 31

Asp Ile Val Leu Thr Gln Ser Pro Ala Thr Leu Ser Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln His Ser Trp
                85                  90                  95

Glu Ile Pro Tyr Thr Phe Gly Gln Gly Thr Lys Leu Glu Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Synthetic Construct

<400> SEQUENCE: 32

Glu Ile Val Leu Thr Gln Ser Pro Ala Thr Leu Ser Leu Ser Pro Gly
1               5                   10                  15

Gln Arg Leu Thr Ile Ser Cys Arg Ala Ser Gln Ser Val Ser Thr Ser
            20                  25                  30

Gly Tyr Ser Tyr Met His Trp Tyr Gln Gln Lys Pro Asp Gln Ser Pro
        35                  40                  45

Lys Leu Leu Ile Lys Phe Gly Ser Asn Leu Glu Ser Gly Ile Pro Ala
    50                  55                  60

```
Arg Phe Ser Gly Ser Gly Ser Gly Thr Asp Phe Thr Leu Thr Ile Ser
 65                  70                  75                  80

Ser Leu Glu Pro Glu Asp Phe Ala Thr Tyr Tyr Cys Gln His Ser Trp
                 85                  90                  95

Glu Ile Pro Tyr Thr Phe Gly Gln Gly Thr Lys Leu Glu Ile Lys
            100                 105                 110
```

<210> SEQ ID NO 33
<211> LENGTH: 111
<212> TYPE: PRT
<213> ORGANISM: Artificial Sequence
<220> FEATURE:
<223> OTHER INFORMATION: Synthetic Construct

<400> SEQUENCE: 33

```
Asp Ile Val Leu Thr Gln Ser Pro Ala Thr Leu Ser Leu Ser Pro Gly
  1               5                  10                  15

Gln Arg Leu Thr Ile Ser Cys Arg Ala Ser Gln Ser Val Ser Thr Ser
                 20                  25                  30

Gly Tyr Ser Tyr Met His Trp Tyr Gln Gln Lys Pro Asp Gln Ser Pro
             35                  40                  45

Lys Leu Leu Ile Lys Phe Gly Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Trp
                 85                  90                  95

Glu Ile Pro Tyr Thr Phe Gly Gln Gly Thr Lys Leu Glu Ile Lys
            100                 105                 110
```

<210> SEQ ID NO 34
<211> LENGTH: 115
<212> TYPE: PRT
<213> ORGANISM: Artificial Sequence
<220> FEATURE:
<223> OTHER INFORMATION: Synthetic Construct

<400> SEQUENCE: 34

```
Glu Val Gln Leu Val Gln Ser Gly Pro Glu Leu Lys Lys Pro Gly Ala
  1               5                  10                  15

Ser Val Lys Met Ser Cys Lys Ala Ser Gly Tyr Thr Phe Thr Ser Tyr
                 20                  25                  30

Val Met His Trp Val Lys Gln Ala Pro Gly Gln Arg Leu Glu Trp Ile
             35                  40                  45

Gly Tyr Val Asn Pro Phe Asn Asp Gly Thr Lys Tyr Asn Glu Met Phe
 50                  55                  60

Lys Gly Arg Ala Thr Leu Thr Ser Asp Lys Ser Thr Ser Thr Ala Tyr
 65                  70                  75                  80

Met Glu Leu Ser Ser Leu Arg Ser Glu Asp Ser Ala Val Tyr Tyr Cys
                 85                  90                  95

Ala Arg Gln Ala Trp Gly Tyr Pro Trp Gly Gln Gly Thr Leu Val Thr
            100                 105                 110

Val Ser Ser
        115
```

<210> SEQ ID NO 35
<211> LENGTH: 115
<212> TYPE: PRT

```
<213> ORGANISM: Artificial Sequence
<220> FEATURE:
<223> OTHER INFORMATION: Synthetic Construct

<400> SEQUENCE: 35

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
                100                 105                 110

Val Ser Ser
        115

<210> SEQ ID NO 38
<211> LENGTH: 115
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Val Asn Pro Phe Asn Asp Gly Thr Lys Tyr Asn Glu Met Phe
    50                  55                  60

Lys Gly Arg Ala Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Trp Gly Tyr Pro Trp Gly Gln Gly Thr Leu Val Thr
                100                 105                 110

Val Ser Ser
        115

<210> SEQ ID NO 39
<211> LENGTH: 111
<212> TYPE: PRT
<213> ORGANISM: Artificial Sequence
<220> FEATURE:
<223> OTHER INFORMATION: Synthetic Construct

<400> SEQUENCE: 39

Asp Ile Val Leu Thr Gln Ser Pro Ala Ser Leu Ala Leu Ser Pro Gly
1               5                   10                  15

Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Glu Glu Asp Ala Ala Met Tyr Phe Cys Gln Gln Ser Arg
```

```
                85                  90                  95

Arg Val Pro Tyr Thr Phe Gly Gln Gly Thr Lys Leu Glu Ile Lys
                100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Synthetic Construct

<400> SEQUENCE: 40

Asp Ile Val Leu Thr Gln Ser Pro Ala Thr Leu Ser Leu Ser Pro Gly
1               5                   10                  15

Glu Arg Ala Thr Leu Ser Cys Arg Ala Thr Glu Ser Val Glu Tyr Tyr
                20                  25                  30

Gly Thr Ser Leu Val Gln Trp Tyr Gln Gln Lys Pro Gly Gln Pro Pro
            35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
                100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Synthetic Construct

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Thr Glu Ser Val Glu Tyr Tyr
                20                  25                  30

Gly Thr Ser Leu Val Gln Trp Tyr Gln Gln Lys Pro Gly Gln Pro Pro
            35                  40                  45

Lys Leu Leu Ile Tyr Ala Ala Ser Ser Val Asp Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Met Tyr Phe Cys Gln Gln Ser Arg
                85                  90                  95

Arg Val Pro Tyr Thr Phe Gly Gln Gly Thr Lys Leu Glu Ile Lys
                100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Synthetic Construct

<400> SEQUENCE: 42

Asp Ile Val Leu Thr Gln Ser Pro Ala Thr Leu Ser Leu Ser Pro Gly
1               5                   10                  15
```

```
Glu Arg Ala Thr Leu Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ser
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Phe Cys Gln Gln Ser Arg
                85                  90                  95

Arg Val Pro Tyr Thr Phe Gly Gln Gly Thr Lys Leu Glu Ile Lys
                100                 105                 110

<210> SEQ ID NO 43
<211> LENGTH: 114
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Leu Lys Lys Pro Gly Ala
 1               5                  10                  15

Ser Val Lys Met Ser Cys Lys Ala Ser Gly Tyr Thr Phe Thr Gly Tyr
                20                  25                  30

Thr Met His Trp Val Lys Gln Ala Pro Gly Gln Gly Leu Glu Trp Ile
            35                  40                  45

Gly Tyr Ile Asn Pro Arg Ser Gly Tyr Thr Glu Tyr Asn Gln Lys Phe
 50                  55                  60

Lys Asp Arg Thr Thr Leu Thr Ala Asp Lys Ser Thr Ser Thr Ala Tyr
 65                  70                  75                  80

Met Glu Leu Ser Ser Leu Arg Ser Glu Asp Ser Ala Val Tyr Tyr Cys
                85                  90                  95

Ala Arg Pro Trp Phe Ala Tyr Trp Gly Gln Gly Thr Leu Val Thr Val
                100                 105                 110

Ser Ser

<210> SEQ ID NO 44
<211> LENGTH: 114
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Val Gln Ser Gly Ala Glu Val Lys Lys Pro Gly Ala
 1               5                  10                  15

Ser Val Lys Met Ser Cys Lys Ala Ser Gly Tyr Thr Phe Thr Gly Tyr
                20                  25                  30

Thr Met His Trp Val Lys Gln Ala Pro Gly Gln Gly Leu Glu Trp Ile
            35                  40                  45

Gly Tyr Ile Asn Pro Arg Ser Gly Tyr Thr Glu Tyr Asn Gln Lys Phe
 50                  55                  60

Lys Asp Arg Thr Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95
```

Ala Arg Pro Trp Phe Ala Tyr Trp Gly Gln Gly Thr Leu Val Thr Val
            100                 105                 110

Ser Ser

<210> SEQ ID NO 45
<211> LENGTH: 114
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Pro Trp Phe Ala Tyr Trp Gly Gln Gly Thr Leu Val Thr Val
            100                 105                 110

Ser Ser

<210> SEQ ID NO 46
<211> LENGTH: 114
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Pro Trp Phe Ala Tyr Trp Gly Gln Gly Thr Leu Val Thr Val
            100                 105                 110

Ser Ser

<210> SEQ ID NO 47
<211> LENGTH: 114
<212> TYPE: PRT
<213> ORGANISM: Artificial Sequence
<220> FEATURE:
<223> OTHER INFORMATION: Synthetic Construct

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Gln Lys Phe
50                  55                  60

Lys Asp Arg Thr Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Trp Phe Ala Tyr Trp Gly Gln Gly Thr Leu Val Thr Val
            100                 105                 110

Ser Ser
```

<210> SEQ ID NO 48
<211> LENGTH: 113
<212> TYPE: PRT
<213> ORGANISM: Artificial Sequence
<220> FEATURE:
<223> OTHER INFORMATION: Synthetic Construct

<400> SEQUENCE: 48

```
Asp Ile Val Met Thr Gln Ser Pro Ala Ser Leu Thr Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Leu Glu Ile
            100                 105                 110

Lys
```

<210> SEQ ID NO 49
<211> LENGTH: 113
<212> TYPE: PRT
<213> ORGANISM: Artificial Sequence
<220> FEATURE:
<223> OTHER INFORMATION: Synthetic Construct

<400> SEQUENCE: 49

```
Asp Ile Val Met Thr Gln Ser Pro Ala Ser Leu Ser Val Thr Pro Gly
1               5                   10                  15

Glu Lys Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
```

```
                50                  55                  60
Pro Asp Arg Phe Thr Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                     85                  90                  95

Asp Tyr Ser Tyr Pro Leu Thr Phe Gly Gln Gly Thr Lys Leu Glu Ile
                100                 105                 110

Lys

<210> SEQ ID NO 50
<211> LENGTH: 113
<212> TYPE: PRT
<213> ORGANISM: Artificial Sequence
<220> FEATURE:
<223> OTHER INFORMATION: Synthetic Construct

<400> SEQUENCE: 50

Asp Ile Val Met Thr Gln Ser Pro Ala Phe Leu Ser Val Thr Pro Gly
  1               5                  10                  15

Glu Lys Val Thr Ile Thr Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                     85                  90                  95

Asp Tyr Ser Tyr Pro Leu Thr Phe Gly Gln Gly Thr Lys Leu Glu Ile
                100                 105                 110

Lys

<210> SEQ ID NO 51
<211> LENGTH: 113
<212> TYPE: PRT
<213> ORGANISM: Artificial Sequence
<220> FEATURE:
<223> OTHER INFORMATION: Synthetic Construct

<400> SEQUENCE: 51

Asp Ile Val Met Thr Gln Ser Pro Ala Phe Leu Ser Val Thr Pro Gly
  1               5                  10                  15

Glu Lys Val Thr Ile Thr Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                     85                  90                  95

Asp Tyr Ser Tyr Pro Leu Thr Phe Gly Gln Gly Thr Lys Leu Glu Ile
                100                 105                 110

Lys
```

<210> SEQ ID NO 52
<211> LENGTH: 363
<212> TYPE: DNA
<213> ORGANISM: Artificial Sequence
<220> FEATURE:
<223> OTHER INFORMATION: Synthetic Construct

<400> SEQUENCE: 52
caggtccagc ttgtgcagtc tgggcatgaa gtgaaacagc ctggggcctc agtgaagatg    60
tcctgcaagg cttctggcta cagttttact agctcctgga tacactgggt gagacaggct   120
cctggacagg gtctggaatg gattggatac atttatccta gcactggttt tactgagtac   180
aatcagaagt tcaaggacag ggccacattg actgcagaca atccaccag cacagcctac    240 atggaactga gcagcctgag atctgaggac actgcagtct attactgtgc aagatggagg   300
gacagctcgg gctaccatgc tatggactac tggggtcaag aaccctggt caccgtctcc    360 tca                                                                  363

<210> SEQ ID NO 53
<211> LENGTH: 363
<212> TYPE: DNA
<213> ORGANISM: Artificial Sequence
<220> FEATURE:
<223> OTHER INFORMATION: Synthetic Construct

<400> SEQUENCE: 53
caggtccagc ttgtgcagtc tgggcatgaa gtgaaacagc ctggggcctc agtgaaggtg    60
tcctgcaagg cttctggcta cagttttact agctcctgga tacactgggt gagacaggct   120
cctggacagg gtctggaatg gattggatac atttatccta gcactggttt tactgagtac   180
aatcagaagt tcaaggacag ggccacaatc actgcagaca atccaccag cacagcctac    240 atggaactga gcagcctgag atctgaggac actgcagtct attactgtgc aagatggagg   300
gacagctcgg gctaccatgc tatggactac tggggtcaag aaccctggt caccgtctcc    360 tca                                                                  363

<210> SEQ ID NO 54
<211> LENGTH: 333
<212> TYPE: DNA
<213> ORGANISM: Artificial Sequence
<220> FEATURE:
<223> OTHER INFORMATION: Synthetic Construct

<400> SEQUENCE: 54
gacattgtgc tgacacagtc tcctgcttcc ttaactctgt ctccagggca gaggctcacc    60
atctcatgca gggccagcca aagtgtcagt acatctggct atagttatat gcactggtac   120
caacagaaac cagaccagtc ccccaaactc ctcatcaagt ttggctccaa cctagaatct   180
ggcatccctg ccaggttcag tggcagtggg tctgggacag acttcaccct caccatctct   240
tctctggagg aggaggattt tgcaacatat tactgtcagc acagtgggga gattccgtac   300
acgttcggac aggggaccaa gctggaaata aaa                                 333

<210> SEQ ID NO 55
<211> LENGTH: 333
<212> TYPE: DNA
<213> ORGANISM: Artificial Sequence
<220> FEATURE:
<223> OTHER INFORMATION: Synthetic Construct

<400> SEQUENCE: 55

```
gacattgtgc tgacacagtc tcctgctacc ttatctctgt ctccagggca gaggctcacc      60
atctcatgca gggccagcca aagtgtcagt acatctggct atagttatat gcactggtac     120
caacagaaac cagaccagtc ccccaaactc ctcatcaagt ttggctccaa cctagaatct     180
ggcatccctg ccaggttcag tggcagtggg tctgggacag acttcaccct caccatctct     240
tctctggagc ctgaggattt tgcaacatat tactgtcagc acagttggga gattccgtac     300
acgttcggac aggggaccaa gctggaaata aaa                                  333
```

<210> SEQ ID NO 56
<211> LENGTH: 333
<212> TYPE: DNA
<213> ORGANISM: Artificial Sequence
<220> FEATURE:
<223> OTHER INFORMATION: Synthetic Construct

<400> SEQUENCE: 56

```
gagattgtgc tgacacagtc tcctgctacc ttatctctgt ctccagggca gaggctcacc      60
atctcatgca gggccagcca aagtgtcagt acatctggct atagttatat gcactggtac     120
caacagaaac cagaccagtc ccccaaactc ctcatcaagt ttggctccaa cctagaatct     180
ggcatccctg ccaggttcag tggcagtggg tctgggacag acttcaccct caccatctct     240
tctctggagc ctgaggattt tgcaacatat tactgtcagc acagttggga gattccgtac     300
acgttcggac aggggaccaa gctggaaata aaa                                  333
```

<210> SEQ ID NO 57
<211> LENGTH: 333
<212> TYPE: DNA
<213> ORGANISM: Artificial Sequence
<220> FEATURE:
<223> OTHER INFORMATION: Synthetic Construct

<400> SEQUENCE: 57

```
gacattgtgc tgacacagtc tcctgctacc ttatctctgt ctccagggca gaggctcacc      60
atctcatgca gggccagcca aagtgtcagt acatctggct gaggctcacc atctcatgca     120
gggccagcca aagtgtcagt acatctggct ctcatcaagt ttggctccaa cctagaatct     180
ggcatccctg ccaggttcag tggcagtggg tctgggacag acttcaccct caccatctct     240
tctctggagc ctgaggattt tgcagtgtat tactgtcagc acagttggga gattccgtac     300
acgttcggac aggggaccaa gctggaaata aaa                                  333
```

<210> SEQ ID NO 58
<211> LENGTH: 345
<212> TYPE: DNA
<213> ORGANISM: Artificial Sequence
<220> FEATURE:
<223> OTHER INFORMATION: Synthetic Construct

<400> SEQUENCE: 58

```
gaggtccagc tggtgcagtc tggacctgag ctgaaaaagc ctggggcttc agtgaagatg      60
tcctgcaagg cttctggata cacattcact agctatgtta tgcactgggt gaagcaggcc     120
cctgggcagc gccttgagtg gattggatat gttaatcctt caatgatgg tactaagtac      180 aatgagatgt tcaaaggcag ggccacactg acttcagaca atccaccag cacagcctac      240 atggagctca gcagcctgag gtctgaggac tctgcggtct attactgtgc aagacaggct     300
tggggttacc cctggggcca agggactctg gtcactgtct cttct                     345
```

<210> SEQ ID NO 59
<211> LENGTH: 345
<212> TYPE: DNA
<213> ORGANISM: Artificial Sequence
<220> FEATURE:
<223> OTHER INFORMATION: Synthetic Construct

<400> SEQUENCE: 59

```
gaggtccagc tggtgcagtc tggagctgag gtgaaaaagc ctggggcttc agtgaagatg     60
tcctgcaagg cttctggata cacattcact agctatgtta tgcactgggt gaagcaggcc    120
cctgggcagc gccttgagtg gattggatat gttaatcctt tcaatgatgg tactaagtac    180
aatgagatgt tcaaaggcag ggccacactg acttcagaca aatccaccag cacagcctac    240
atggagctca gcagcctgag gtctgaggac actgcggtct attactgtgc aagacaggct    300
tggggttacc cctggggcca agggactctg gtcactgtct cttct                    345
```

<210> SEQ ID NO 60
<211> LENGTH: 344
<212> TYPE: DNA
<213> ORGANISM: Artificial Sequence
<220> FEATURE:
<223> OTHER INFORMATION: Synthetic Construct

<400> SEQUENCE: 60

```
gaggtccagc tggtgcagtc tggagctgag gtgaaaaagc ctggggcttc agtgaagatg     60
tcctgcaagg cttctggata cacattcact agctatgtta tgcactgggt gaggcaggcc    120
cctgggcagc gccttgagtg gattggatat gttaatcctt tcaatgatgg tactaagtac    180
aatgagatgt tcaaaggcag ggccacactg acttcagaca aatccaccag cacagcctac    240
atggagctca gcagcctgag gtctgaggac actgcggtct attactgtgc aagacaggct    300
ggggttaccc ctggggccaa gggactctgg tcactgtctc ttct                     344
```

<210> SEQ ID NO 61
<211> LENGTH: 345
<212> TYPE: DNA
<213> ORGANISM: Artificial Sequence
<220> FEATURE:
<223> OTHER INFORMATION: Synthetic Construct

<400> SEQUENCE: 61

```
gaggtccagc tggtgcagtc tggagctgag gtgaaaaagc ctggggcttc agtgaaggtg     60
tcctgcaagg cttctggata cacattcact agctatgtta tgcactgggt gaggcaggcc    120
cctgggcagc gccttgagtg gattggatat gttaatcctt tcaatgatgg tactaagtac    180
aatgagatgt tcaaaggcag ggccacactg acttcagaca aatccaccag cacagcctac    240
atggagctca gcagcctgag gtctgaggac actgcggtct attactgtgc aagacaggct    300
tggggttacc cctggggcca agggactctg gtcactgtct cttct                    345
```

<210> SEQ ID NO 62
<211> LENGTH: 345
<212> TYPE: DNA
<213> ORGANISM: Artificial Sequence
<220> FEATURE:
<223> OTHER INFORMATION: Synthetic Construct

<400> SEQUENCE: 62

```
gaggtccagc tggtgcagtc tggagctgag gtgaaaaagc ctggggcttc agtgaaggtg     60
tcctgcaagg cttctggata cacattcact agctatgtta tgcactgggt gaggcaggcc    120
```

```
cctgggcagc gccttgagtg gattggatat gttaatcctt tcaatgatgg tactaagtac    180
aatgagatgt tcaaaggcag ggccacaatc acttcagaca aatccaccag cacagcctac    240
atggagctca gcagcctgag gtctgaggac actgcggtct attactgtgc aagacaggct    300
tggggttacc cctggggcca agggactctg gtcactgtct cttct                    345
```

<210> SEQ ID NO 63
<211> LENGTH: 333
<212> TYPE: DNA
<213> ORGANISM: Artificial Sequence
<220> FEATURE:
<223> OTHER INFORMATION: Synthetic Construct

<400> SEQUENCE: 63

```
gacattgtgc tcacccaatc tccagcttct ttggctctgt ctcccgggga gagagccacc     60
ctctcctgca gagccactga aagtgttgaa tactatggca caagtttagt gcagtggtac    120
caacagaaac caggacagcc acccaaactc ctcatctatg ctgcatccag cgtagattct    180
ggggtccctt ccaggtttag tggcagtggg tctgggacag acttcaccct caccatcaat    240
tctctggagg aggaggatgc tgcaatgtat ttctgtcagc aaagtaggag ggttccgtac    300
acgttcggac aggggaccaa gctggagata aaa                                 333
```

<210> SEQ ID NO 64
<211> LENGTH: 333
<212> TYPE: DNA
<213> ORGANISM: Artificial Sequence
<220> FEATURE:
<223> OTHER INFORMATION: Synthetic Construct

<400> SEQUENCE: 64

```
gacattgtgc tcacccaatc tccagctact ttgtctctgt ctcccgggga gagagccacc     60
ctctcctgca gagccactga aagtgttgaa tactatggca caagtttagt gcagtggtac    120
caacagaaac caggacagcc acccaaactc ctcatctatg ctgcatccag cgtagattct    180
ggggtccctt ccaggtttag tggcagtggg tctgggacag acttcaccct caccatcaat    240
tctctggagg ccgaggatgc tgcaatgtat ttctgtcagc aaagtaggag ggttccgtac    300
acgttcggac aggggaccaa gctggagata aaa                                 333
```

<210> SEQ ID NO 65
<211> LENGTH: 333
<212> TYPE: DNA
<213> ORGANISM: Artificial Sequence
<220> FEATURE:
<223> OTHER INFORMATION: Synthetic Construct

<400> SEQUENCE: 65

```
gagattgtgc tcacccaatc tccagctact ttgtctctgt ctcccgggga gagagccacc     60
ctctcctgca gagccactga aagtgttgaa tactatggca caagtttagt gcagtggtac    120
caacagaaac caggacagcc acccaaactc ctcatctatg ctgcatccag cgtagattct    180
ggggtccctt ccaggtttag tggcagtggg tctgggacag acttcaccct caccatcaat    240
tctctggagg ccgaggatgc tgcaatgtat ttctgtcagc aaagtaggag ggttccgtac    300
acgttcggac aggggaccaa gctggagata aaa                                 333
```

<210> SEQ ID NO 66
<211> LENGTH: 333
<212> TYPE: DNA

```
<213> ORGANISM: Artificial Sequence
<220> FEATURE:
<223> OTHER INFORMATION: Synthetic Construct

<400> SEQUENCE: 66
gacattgtgc tcacccaatc tccagctact ttgtctctgt ctcccgggga gagagccacc      60
ctctcctgca gagccactga aagtgttgaa tactatggca caagtttagt gcagtggtac     120
caacagaaac caggacagcc acccaaactc ctcatctatg ctgcatccag cgtagattct     180 ggggtcccctt ccaggtttag tggcagtggg tctgggacag acttcaccct caccatcaat    240
tctctggagg ccgaggatgc tgcaacctat ttctgtcagc aaagtaggag ggttccgtac     300
acgttcggac aggggaccaa gctggagata aaa                                  333

<210> SEQ ID NO 67
<211> LENGTH: 342
<212> TYPE: DNA
<213> ORGANISM: Artificial Sequence
<220> FEATURE:
<223> OTHER INFORMATION: Synthetic Construct

<400> SEQUENCE: 67
caggtccagc tggtgcagtc tggagctgaa ctgaagaaac ctggggcctc agtgaagatg      60
tcctgcaagg cttctggcta cacctttact ggctacacga tgcactgggt aaaacaggcc    120
cctggacagg gtctggaatg gattggatac attaatccta gaagtggata tactgagtat    180
aatcagaagt tcaaggacag gaccacattg actgcagaca atctaccag cacagcctac     240 atggaactga gcagcctgag atctgaggac tctgcggtct attattgtgc aagaccctgg    300
tttgcttact ggggccaagg gactctggtc actgtctctt ca                        342

<210> SEQ ID NO 68
<211> LENGTH: 342
<212> TYPE: DNA
<213> ORGANISM: Artificial Sequence
<220> FEATURE:
<223> OTHER INFORMATION: Synthetic Construct

<400> SEQUENCE: 68
caggtccagc tggtgcagtc tggagctgaa gtgaagaaac ctggggcctc agtgaagatg      60
tcctgcaagg cttctggcta cacctttact ggctacacga tgcactgggt aaaacaggcc    120
cctggacagg gtctggaatg gattggatac attaatccta gaagtggata tactgagtat    180
aatcagaagt tcaaggacag gaccacattg actgcagaca atctaccag cacagcctac     240 atggaactga gcagcctgag atctgaggac actgcggtct attattgtgc aagaccctgg    300
tttgcttact ggggccaagg gactctggtc actgtctctt ca                        342

<210> SEQ ID NO 69
<211> LENGTH: 342
<212> TYPE: DNA
<213> ORGANISM: Artificial Sequence
<220> FEATURE:
<223> OTHER INFORMATION: Synthetic Construct

<400> SEQUENCE: 69
caggtccagc tggtgcagtc tggagctgaa gtgaagaaac ctggggcctc agtgaagatg      60
tcctgcaagg cttctggcta cacctttact ggctacacga tgcactgggt aagacaggcc    120
cctggacagg gtctggaatg gattggatac attaatccta gaagtggata tactgagtat    180
aatcagaagt tcaaggacag gaccacattg actgcagaca atctaccag cacagcctac     240
```

```
atggaactga gcagcctgag atctgaggac actgcggtct attattgtgc aagaccctgg    300
tttgcttact ggggccaagg gactctggtc actgtctctt ca                       342
```

<210> SEQ ID NO 70
<211> LENGTH: 342
<212> TYPE: DNA
<213> ORGANISM: Artificial Sequence
<220> FEATURE:
<223> OTHER INFORMATION: Synthetic Construct

<400> SEQUENCE: 70

```
caggtccagc tggtgcagtc tggagctgaa gtgaagaaac ctggggcctc agtgaaggtg     60
tcctgcaagg cttctggcta cacctttact ggctacacga tgcactgggt aagacaggcc    120
cctggacagg gtctggaatg gattggatac attaatccta gaagtggata tactgagtat    180
aatcagaagt tcaaggacag gaccacattg actgcagaca atctaccag cacagcctac     240 atggaactga gcagcctgag atctgaggac actgcggtct attattgtgc aagaccctgg    300
tttgcttact ggggccaagg gactctggtc actgtctctt ca                       342
```

<210> SEQ ID NO 71
<211> LENGTH: 342
<212> TYPE: DNA
<213> ORGANISM: Artificial Sequence
<220> FEATURE:
<223> OTHER INFORMATION: Synthetic Construct

<400> SEQUENCE: 71

```
caggtccagc tggtgcagtc tggagctgaa gtgaagaaac ctggggcctc agtgaaggtg     60
tcctgcaagg cttctggcta cacctttact ggctacacga tgcactgggt aagacaggcc    120
cctggacagg gtctggaatg gattggatac attaatccta gaagtggata tactgagtat    180
aatcagaagt tcaaggacag gaccacaatc actgcagaca atctaccag cacagcctac     240 atggaactga gcagcctgag atctgaggac actgcggtct attattgtgc aagaccctgg    300
tttgcttact ggggccaagg gactctggtc actgtctctt ca                       342
```

<210> SEQ ID NO 72
<211> LENGTH: 339
<212> TYPE: DNA
<213> ORGANISM: Artificial Sequence
<220> FEATURE:
<223> OTHER INFORMATION: Synthetic Construct

<400> SEQUENCE: 72

```
gacattgtga tgacacagtc tccagcctcc ctgactgtga caccaggaga gaaggtcact     60
atcacctgca gtccagtca gagtctgtta aacagtggaa atcaaaagaa ctacttgacc     120
tggtaccagc agaaaccagg gcagcctcct aaactgttga tctactgggc atccactagg    180
gaatctgggg tccctgatcg cttcacaggc agtggatctg gaacagattt cactctcacc    240
atcagcagtc tgcaggctga agacgtggca gtttattact gtcagaatga ttatagttat    300
cctctcacgt tcggtcaggg gaccaagctg gagatcaaa                           339
```

<210> SEQ ID NO 73
<211> LENGTH: 339
<212> TYPE: DNA
<213> ORGANISM: Artificial Sequence
<220> FEATURE:
<223> OTHER INFORMATION: Synthetic Construct

<400> SEQUENCE: 73

```
gacattgtga tgacacagtc tccagcctcc ctgtctgtga caccaggaga gaaggtcact      60
atcacctgca agtccagtca gagtctgtta aacagtggaa atcaaaagaa ctacttgacc     120
tggtaccagc agaaaccagg gcagcctcct aaactgttga tctactgggc atccactagg    180
gaatctgggg tccctgatcg cttcacaggc agtggatctg gaacagattt cactctcacc    240
atcagcagtc tgcaggctga agacgtggca gtttattact gtcagaatga ttatagttat    300
cctctcacgt tcggtcaggg gaccaagctg gagatcaaa                           339
```

<210> SEQ ID NO 74
<211> LENGTH: 339
<212> TYPE: DNA
<213> ORGANISM: Artificial Sequence
<220> FEATURE:
<223> OTHER INFORMATION: Synthetic Construct

<400> SEQUENCE: 74

```
gacattgtga tgacacagtc tccagccttc ctgtctgtga caccaggaga gaaggtcact    60
atcacctgca agtccagtca gagtctgtta aacagtggaa atcaaaagaa ctacttgacc   120
tggtaccagc agaaaccagg gcagcctcct aaactgttga tctactgggc atccactagg  180
gaatctgggg tccctgatcg cttcacaggc agtggatctg gaacagattt cactctcacc  240
atcagcagtc tgcaggctga agacgtggca gtttattact gtcagaatga ttatagttat  300
cctctcacgt tcggtcaggg gaccaagctg gagatcaaa                         339
```

<210> SEQ ID NO 75
<211> LENGTH: 339
<212> TYPE: DNA
<213> ORGANISM: Artificial Sequence
<220> FEATURE:
<223> OTHER INFORMATION: Synthetic Construct

<400> SEQUENCE: 75

```
gacattgtga tgacacagtc tccagccttc ctgtctgtga caccaggaga gaaggtcact    60
atcacctgca agtccagtca gagtctgtta aacagtggaa atcaaaagaa ctacttgacc   120
tggtaccagc agaaaccagg gcagcctcct aaactgttga tctactgggc atccactagg  180
gaatctgggg tccctgatcg cttctccggc agtggatctg gaacagattt cactctcacc  240
atcagcagtc tgcaggctga agacgtggca gtttattact gtcagaatga ttatagttat  300
cctctcacgt tcggtcaggg gaccaagctg gagatcaaa                         339
```

<210> SEQ ID NO 76
<211> LENGTH: 121
<212> TYPE: PRT
<213> ORGANISM: Mus musculus

<400> SEQUENCE: 76

Gln Val Gln Leu Gln Gln Ser Gly Ala Glu Leu Ala Lys Pro Gly Ala
1               5                   10                  15

Ser Val Gln Met Ser Cys Lys Ala Ser Gly Tyr Ser Phe Thr Ser Ser
                20                  25                  30

Trp Ile His Trp Val Lys Gln Arg Pro Gly Gln Gly Leu Glu Trp Ile
            35                  40                  45

Gly Tyr Ile Tyr Pro Ser Thr Gly Phe Thr Glu Tyr Asn Gln Lys Phe
        50                  55                  60

Lys Asp Lys Ala Thr Leu Thr Ala Asp Lys Ser Ser Ser Thr Ala Tyr

```
                65                  70                  75                  80
Met Gln Leu Ser Ser Leu Thr Ser Glu Asp Ser Ala Val Tyr Tyr Cys
                    85                  90                  95

Ala Arg Trp Arg Asp Ser Ser Gly Tyr His Ala Met Asp Tyr Trp Gly
                100                 105                 110

Gln Gly Thr Ser Val Thr Val Ser Ser
            115                 120
```

<210> SEQ ID NO 77
<211> LENGTH: 111
<212> TYPE: PRT
<213> ORGANISM: Mus musculus

<400> SEQUENCE: 77

```
Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Lys Phe Gly Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
                100                 105                 110
```

<210> SEQ ID NO 78
<211> LENGTH: 115
<212> TYPE: PRT
<213> ORGANISM: Mus musculus

<400> SEQUENCE: 78

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Val Asn Pro Phe Asn Asp Gly Thr Lys Tyr Asn Glu Met Phe
50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gln Ala Trp Gly Tyr Pro Trp Gly Gln Gly Thr Leu Val Thr
                100                 105                 110

Val Ser Ala
        115
```

<210> SEQ ID NO 79
<211> LENGTH: 111
<212> TYPE: PRT
<213> ORGANISM: Mus musculus

<400> SEQUENCE: 79

Asp Ile Val Leu Thr Gln Ser Pro Ala Ser Leu Ala Val Ser Leu Gly
1               5                   10                  15

Gln Arg Ala Thr Ile Ser Cys Arg Ala Thr Glu Ser Val Glu Tyr Tyr
            20                  25                  30

Gly Thr Ser Leu Val Gln Trp Tyr Gln Gln Lys Pro Gly Gln Pro Pro
        35                  40                  45

Lys Leu Leu Ile Tyr Ala Ala Ser Ser Val Asp Ser Gly Val Pro Ala
    50                  55                  60

Arg Phe Ser Gly Ser Gly Ser Gly Thr Asp Phe Ser Leu Thr Ile His
65                  70                  75                  80

Pro Val Glu Glu Asp Asp Ile Ala Met Tyr Phe Cys Gln Gln Ser Arg
                85                  90                  95

Arg Val Pro Tyr Thr Phe Gly Gly Gly Thr Lys Leu Glu Ile Lys
            100                 105                 110

<210> SEQ ID NO 80
<211> LENGTH: 114
<212> TYPE: PRT
<213> ORGANISM: Mus musculus

<400> SEQUENCE: 80

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Gly Tyr
            20                  25                  30

Thr Met His Trp Val Lys Gln Arg Pro Gly Gln Gly Leu Glu Trp Ile
        35                  40                  45

Gly Tyr Ile Asn Pro Arg Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Pro Trp Phe Ala Tyr Trp Gly Gln Gly Thr Leu Val Thr Val
            100                 105                 110

Ser Ala

<210> SEQ ID NO 81
<211> LENGTH: 113
<212> TYPE: PRT
<213> ORGANISM: Mus musculus

<400> SEQUENCE: 81

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110
Lys

<210> SEQ ID NO 82
<211> LENGTH: 19
<212> TYPE: PRT
<213> ORGANISM: Homo sapiens

<400> SEQUENCE: 82

Gln Val Gln Leu Val Gln Ser Gly His Glu Val Lys Gln Pro Gly Ala
1               5                   10                  15

Ser Val Lys

<210> SEQ ID NO 83
<211> LENGTH: 12
<212> TYPE: PRT
<213> ORGANISM: Homo sapiens

<400> SEQUENCE: 83

Met Ser Cys Lys Ala Ser Gly Tyr Ser Phe Thr Ser
1               5                   10

<210> SEQ ID NO 84
<211> LENGTH: 10
<212> TYPE: PRT
<213> ORGANISM: Homo sapiens

<400> SEQUENCE: 84

Ser Gly Tyr Ser Phe Thr Ser Ser Trp Ile
1               5                   10

<210> SEQ ID NO 85
<211> LENGTH: 5
<212> TYPE: PRT
<213> ORGANISM: Homo sapiens

<400> SEQUENCE: 85

Trp Ile His Trp Val
1               5

<210> SEQ ID NO 86
<211> LENGTH: 11
<212> TYPE: PRT
<213> ORGANISM: Homo sapiens

<400> SEQUENCE: 86

Gln Ala Pro Gly Gln Gly Leu Glu Trp Ile Gly
1               5                   10

<210> SEQ ID NO 87
<211> LENGTH: 11
<212> TYPE: PRT
<213> ORGANISM: Homo sapiens

<400> SEQUENCE: 87

Gly Leu Glu Trp Ile Gly Tyr Ile Tyr Pro Ser
1               5                   10

<210> SEQ ID NO 88
<211> LENGTH: 4
<212> TYPE: PRT
<213> ORGANISM: Homo sapiens

```
<400> SEQUENCE: 88

Ser Thr Gly Phe
1

<210> SEQ ID NO 89
<211> LENGTH: 4
<212> TYPE: PRT
<213> ORGANISM: Homo sapiens

<400> SEQUENCE: 89

Thr Glu Tyr Asn
1

<210> SEQ ID NO 90
<211> LENGTH: 4
<212> TYPE: PRT
<213> ORGANISM: Homo sapiens

<400> SEQUENCE: 90

Asp Arg Ala Thr
1

<210> SEQ ID NO 91
<211> LENGTH: 28
<212> TYPE: PRT
<213> ORGANISM: Homo sapiens

<400> SEQUENCE: 91

Thr Ala Asp Lys Ser Thr Ser Thr Ala Tyr Met Glu Leu Ser Ser Leu
1               5                   10                  15

Arg Ser Glu Asp Thr Ala Val Tyr Tyr Cys Ala Arg
            20                  25

<210> SEQ ID NO 92
<211> LENGTH: 25
<212> TYPE: PRT
<213> ORGANISM: Homo sapiens

<400> SEQUENCE: 92

Ser Thr Ala Tyr Met Glu Leu Ser Ser Leu Arg Ser Glu Asp Thr Ala
1               5                   10                  15

Val Tyr Tyr Cys Ala Arg Trp Arg Asp
            20                  25

<210> SEQ ID NO 93
<211> LENGTH: 5
<212> TYPE: PRT
<213> ORGANISM: Homo sapiens

<400> SEQUENCE: 93

Asp Ser Ser Gly Tyr
1               5

<210> SEQ ID NO 94
<211> LENGTH: 13
<212> TYPE: PRT
<213> ORGANISM: Homo sapiens

<400> SEQUENCE: 94

Asp Tyr Trp Gly Gln Gly Thr Leu Val Thr Val Ser Ser
1               5                   10

<210> SEQ ID NO 95
```

```
<211> LENGTH: 15
<212> TYPE: PRT
<213> ORGANISM: Homo sapiens

<400> SEQUENCE: 95

His Trp Val Arg Gln Ala Pro Gly Gln Gly Leu Glu Trp Ile Gly
1               5                   10                  15

<210> SEQ ID NO 96
<211> LENGTH: 18
<212> TYPE: PRT
<213> ORGANISM: Homo sapiens

<400> SEQUENCE: 96

Glu Ile Val Leu Thr Gln Ser Pro Ala Thr Leu Ser Leu Ser Pro Gly
1               5                   10                  15

Gln Arg

<210> SEQ ID NO 97
<211> LENGTH: 10
<212> TYPE: PRT
<213> ORGANISM: Homo sapiens

<400> SEQUENCE: 97

Arg Leu Thr Ile Ser Cys Arg Ala Ser Gln
1               5                   10

<210> SEQ ID NO 98
<211> LENGTH: 12
<212> TYPE: PRT
<213> ORGANISM: Homo sapiens

<400> SEQUENCE: 98

Thr Ile Ser Cys Arg Ala Ser Gln Ser Val Ser Thr
1               5                   10

<210> SEQ ID NO 99
<211> LENGTH: 12
<212> TYPE: PRT
<213> ORGANISM: Homo sapiens

<400> SEQUENCE: 99

Ser Val Ser Thr Ser Gly Tyr Ser Tyr Met His Trp
1               5                   10

<210> SEQ ID NO 100
<211> LENGTH: 15
<212> TYPE: PRT
<213> ORGANISM: Homo sapiens

<400> SEQUENCE: 100

Trp Tyr Gln Gln Lys Pro Asp Gln Ser Pro Lys Leu Leu Ile Lys
1               5                   10                  15

<210> SEQ ID NO 101
<211> LENGTH: 6
<212> TYPE: PRT
<213> ORGANISM: Homo sapiens

<400> SEQUENCE: 101

Ser Asn Leu Glu Ser Gly
1               5

<210> SEQ ID NO 102
```

```
<211> LENGTH: 28
<212> TYPE: PRT
<213> ORGANISM: Homo sapiens

<400> SEQUENCE: 102

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala
            20                  25

<210> SEQ ID NO 103
<211> LENGTH: 12
<212> TYPE: PRT
<213> ORGANISM: Homo sapiens

<400> SEQUENCE: 103

Pro Glu Asp Phe Ala Thr Tyr Tyr Cys Gln His Ser
1               5                   10

<210> SEQ ID NO 104
<211> LENGTH: 12
<212> TYPE: PRT
<213> ORGANISM: Homo sapiens

<400> SEQUENCE: 104

Tyr Thr Phe Gly Gln Gly Thr Lys Leu Glu Ile Lys
1               5                   10

<210> SEQ ID NO 105
<211> LENGTH: 8
<212> TYPE: PRT
<213> ORGANISM: Homo sapiens

<400> SEQUENCE: 105

Asp Ile Val Leu Thr Gln Ser Pro
1               5

<210> SEQ ID NO 106
<211> LENGTH: 17
<212> TYPE: PRT
<213> ORGANISM: Homo sapiens

<400> SEQUENCE: 106

Ile Val Leu Thr Gln Ser Pro Ala Thr Leu Ser Leu Ser Pro Gly Gln
1               5                   10                  15

Arg

<210> SEQ ID NO 107
<211> LENGTH: 19
<212> TYPE: PRT
<213> ORGANISM: Homo sapiens

<400> SEQUENCE: 107

Glu Val Gln Leu Val Gln Ser Gly Ala Glu Val Lys Lys Pro Gly Ala
1               5                   10                  15

Ser Val Lys

<210> SEQ ID NO 108
<211> LENGTH: 8
<212> TYPE: PRT
<213> ORGANISM: Homo sapiens

<400> SEQUENCE: 108
```

Met Ser Cys Lys Ala Ser Gly Tyr
1               5

<210> SEQ ID NO 109
<211> LENGTH: 12
<212> TYPE: PRT
<213> ORGANISM: Homo sapiens

<400> SEQUENCE: 109

Ser Cys Lys Ala Ser Gly Tyr Thr Phe Thr Ser Tyr
1               5                   10

<210> SEQ ID NO 110
<211> LENGTH: 7
<212> TYPE: PRT
<213> ORGANISM: Homo sapiens

<400> SEQUENCE: 110

Ser Tyr Val Met His Trp Val
1               5

<210> SEQ ID NO 111
<211> LENGTH: 4
<212> TYPE: PRT
<213> ORGANISM: Homo sapiens

<400> SEQUENCE: 111

Trp Val Lys Gln
1

<210> SEQ ID NO 112
<211> LENGTH: 11
<212> TYPE: PRT
<213> ORGANISM: Homo sapiens

<400> SEQUENCE: 112

Gln Ala Pro Gly Gln Arg Leu Glu Trp Ile Gly
1               5                   10

<210> SEQ ID NO 113
<211> LENGTH: 4
<212> TYPE: PRT
<213> ORGANISM: Homo sapiens

<400> SEQUENCE: 113

Val Asn Pro Phe
1

<210> SEQ ID NO 114
<211> LENGTH: 4
<212> TYPE: PRT
<213> ORGANISM: Homo sapiens

<400> SEQUENCE: 114

Asn Asp Gly Thr
1

<210> SEQ ID NO 115
<211> LENGTH: 4
<212> TYPE: PRT
<213> ORGANISM: Homo sapiens

<400> SEQUENCE: 115

Phe Lys Gly Arg
1

<210> SEQ ID NO 116
<211> LENGTH: 4
<212> TYPE: PRT
<213> ORGANISM: Homo sapiens

<400> SEQUENCE: 116

Gly Arg Ala Thr
1

<210> SEQ ID NO 117
<211> LENGTH: 25
<212> TYPE: PRT
<213> ORGANISM: Homo sapiens

<400> SEQUENCE: 117

Asp Lys Ser Thr Ser Thr Ala Tyr Met Glu Leu Ser Ser Leu Arg Ser
1               5                   10                  15

Glu Asp Thr Ala Val Tyr Tyr Cys Ala
            20                  25

<210> SEQ ID NO 118
<211> LENGTH: 9
<212> TYPE: PRT
<213> ORGANISM: Homo sapiens

<400> SEQUENCE: 118

Ala Val Tyr Tyr Cys Ala Arg Gln Ala
1               5

<210> SEQ ID NO 119
<211> LENGTH: 4
<212> TYPE: PRT
<213> ORGANISM: Homo sapiens

<400> SEQUENCE: 119

Ala Trp Gly Tyr
1

<210> SEQ ID NO 120
<211> LENGTH: 12
<212> TYPE: PRT
<213> ORGANISM: Homo sapiens

<400> SEQUENCE: 120

Pro Trp Gly Gln Gly Thr Leu Val Thr Val Ser Ser
1               5                   10

<210> SEQ ID NO 121
<211> LENGTH: 14
<212> TYPE: PRT
<213> ORGANISM: Homo sapiens

<400> SEQUENCE: 121

Trp Val Arg Gln Ala Pro Gly Gln Arg Leu Glu Trp Ile Gly
1               5                   10

<210> SEQ ID NO 122
<211> LENGTH: 14
<212> TYPE: PRT
<213> ORGANISM: Homo sapiens

<400> SEQUENCE: 122

Asp Ile Val Leu Thr Gln Ser Pro Ala Ser Leu Ala Leu Ser

```
1               5                   10
```

<210> SEQ ID NO 123
<211> LENGTH: 8
<212> TYPE: PRT
<213> ORGANISM: Homo sapiens

<400> SEQUENCE: 123

```
Leu Ser Pro Gly Glu Arg Ala Thr
1               5
```

<210> SEQ ID NO 124
<211> LENGTH: 6
<212> TYPE: PRT
<213> ORGANISM: Homo sapiens

<400> SEQUENCE: 124

```
Tyr Tyr Gly Thr Ser Leu
1               5
```

<210> SEQ ID NO 125
<211> LENGTH: 10
<212> TYPE: PRT
<213> ORGANISM: Homo sapiens

<400> SEQUENCE: 125

```
Val Gln Trp Tyr Gln Gln Lys Pro Gly Gln
1               5                   10
```

<210> SEQ ID NO 126
<211> LENGTH: 15
<212> TYPE: PRT
<213> ORGANISM: Homo sapiens

<400> SEQUENCE: 126

```
Trp Tyr Gln Gln Lys Pro Gly Gln Pro Pro Lys Leu Leu Ile Tyr
1               5                   10                  15
```

<210> SEQ ID NO 127
<211> LENGTH: 10
<212> TYPE: PRT
<213> ORGANISM: Homo sapiens

<400> SEQUENCE: 127

```
Pro Lys Leu Leu Ile Tyr Ala Ala Ser Ser
1               5                   10
```

<210> SEQ ID NO 128
<211> LENGTH: 4
<212> TYPE: PRT
<213> ORGANISM: Homo sapiens

<400> SEQUENCE: 128

```
Ser Val Asp Ser
1
```

<210> SEQ ID NO 129
<211> LENGTH: 15
<212> TYPE: PRT
<213> ORGANISM: Homo sapiens

<400> SEQUENCE: 129

```
Asp Ser Gly Val Pro Ser Arg Phe Ser Gly Ser Gly Ser Gly Thr
1               5                   10                  15
```

<210> SEQ ID NO 130
<211> LENGTH: 19
<212> TYPE: PRT
<213> ORGANISM: Homo sapiens

<400> SEQUENCE: 130

Arg Phe Ser Gly Ser Gly Ser Gly Thr Asp Phe Thr Leu Thr Ile Asn
1               5                   10                  15
Ser Leu Glu

<210> SEQ ID NO 131
<211> LENGTH: 6
<212> TYPE: PRT
<213> ORGANISM: Homo sapiens

<400> SEQUENCE: 131

Glu Glu Glu Asp Ala Ala
1               5

<210> SEQ ID NO 132
<211> LENGTH: 7
<212> TYPE: PRT
<213> ORGANISM: Homo sapiens

<400> SEQUENCE: 132

Ala Met Tyr Phe Cys Gln Gln
1               5

<210> SEQ ID NO 133
<211> LENGTH: 7
<212> TYPE: PRT
<213> ORGANISM: Homo sapiens

<400> SEQUENCE: 133

Arg Val Pro Tyr Thr Phe Gly
1               5

<210> SEQ ID NO 134
<211> LENGTH: 16
<212> TYPE: PRT
<213> ORGANISM: Homo sapiens

<400> SEQUENCE: 134

Ile Val Leu Thr Gln Ser Pro Ala Thr Leu Ser Leu Ser Pro Gly Glu
1               5                   10                  15

<210> SEQ ID NO 135
<211> LENGTH: 11
<212> TYPE: PRT
<213> ORGANISM: Homo sapiens

<400> SEQUENCE: 135

Thr Ile Asn Ser Leu Glu Ala Glu Asp Ala Ala
1               5                   10

<210> SEQ ID NO 136
<211> LENGTH: 15
<212> TYPE: PRT
<213> ORGANISM: Homo sapiens

<400> SEQUENCE: 136

Thr Ile Asn Ser Leu Glu Ala Glu Asp Ala Ala Thr Tyr Phe Cys
1               5                   10                  15

<210> SEQ ID NO 137
<211> LENGTH: 19
<212> TYPE: PRT
<213> ORGANISM: Homo sapiens

<400> SEQUENCE: 137

Gln Val Gln Leu Val Gln Ser Gly Ala Glu Val Lys Lys Pro Gly Ala
1               5                   10                  15

Ser Val Lys

<210> SEQ ID NO 138
<211> LENGTH: 12
<212> TYPE: PRT
<213> ORGANISM: Homo sapiens

<400> SEQUENCE: 138

Ser Cys Lys Ala Ser Gly Tyr Thr Phe Thr Gly Tyr
1               5                   10

<210> SEQ ID NO 139
<211> LENGTH: 5
<212> TYPE: PRT
<213> ORGANISM: Homo sapiens

<400> SEQUENCE: 139

Thr Met His Trp Val
1               5

<210> SEQ ID NO 140
<211> LENGTH: 4
<212> TYPE: PRT
<213> ORGANISM: Homo sapiens

<400> SEQUENCE: 140

Gln Ala Pro Gly
1

<210> SEQ ID NO 141
<211> LENGTH: 8
<212> TYPE: PRT
<213> ORGANISM: Homo sapiens

<400> SEQUENCE: 141

Gly Gln Gly Leu Glu Trp Ile Gly
1               5

<210> SEQ ID NO 142
<211> LENGTH: 5
<212> TYPE: PRT
<213> ORGANISM: Homo sapiens

<400> SEQUENCE: 142

Gly Tyr Ile Asn Pro
1               5

<210> SEQ ID NO 143
<211> LENGTH: 6
<212> TYPE: PRT
<213> ORGANISM: Homo sapiens

<400> SEQUENCE: 143

Ile Asn Pro Arg Ser Gly
1               5

<210> SEQ ID NO 144
<211> LENGTH: 11
<212> TYPE: PRT
<213> ORGANISM: Homo sapiens

<400> SEQUENCE: 144

Asp Thr Ala Val Tyr Tyr Cys Ala Arg Pro Trp
1               5                   10

<210> SEQ ID NO 145
<211> LENGTH: 9
<212> TYPE: PRT
<213> ORGANISM: Homo sapiens

<400> SEQUENCE: 145

Trp Phe Ala Tyr Trp Gly Gln Gly Thr
1               5

<210> SEQ ID NO 146
<211> LENGTH: 12
<212> TYPE: PRT
<213> ORGANISM: Homo sapiens

<400> SEQUENCE: 146

Tyr Trp Gly Gln Gly Thr Leu Val Thr Val Ser Ser
1               5                   10

<210> SEQ ID NO 147
<211> LENGTH: 32
<212> TYPE: PRT
<213> ORGANISM: Homo sapiens

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

<210> SEQ ID NO 148
<211> LENGTH: 10
<212> TYPE: PRT
<213> ORGANISM: Homo sapiens

<400> SEQUENCE: 148

Thr Met His Trp Val Arg Gln Ala Pro Gly
1               5                   10

<210> SEQ ID NO 149
<211> LENGTH: 8
<212> TYPE: PRT
<213> ORGANISM: Homo sapiens

<400> SEQUENCE: 149

Asp Ile Val Met Thr Gln Ser Pro
1               5

<210> SEQ ID NO 150
<211> LENGTH: 4
<212> TYPE: PRT
<213> ORGANISM: Homo sapiens

<400> SEQUENCE: 150

Pro Ala Ser Leu
1

<210> SEQ ID NO 151
<211> LENGTH: 13
<212> TYPE: PRT
<213> ORGANISM: Homo sapiens

<400> SEQUENCE: 151

Leu Ser Val Thr Pro Gly Glu Lys Val Thr Ile Thr Cys
1               5                   10

<210> SEQ ID NO 152
<211> LENGTH: 8
<212> TYPE: PRT
<213> ORGANISM: Homo sapiens

<400> SEQUENCE: 152

Cys Lys Ser Ser Gln Ser Leu Leu
1               5

<210> SEQ ID NO 153
<211> LENGTH: 33
<212> TYPE: PRT
<213> ORGANISM: Homo sapiens

<400> SEQUENCE: 153

Lys Asn Tyr Leu Thr Trp Tyr Gln Gln Lys Pro Gly Gln Pro Pro Lys
1               5                   10                  15

Leu Leu Ile Tyr Trp Ala Ser Thr Arg Glu Ser Gly Val Pro Asp Arg
            20                  25                  30

Phe

<210> SEQ ID NO 154
<211> LENGTH: 29
<212> TYPE: PRT
<213> ORGANISM: Homo sapiens

<400> SEQUENCE: 154

Arg Phe Thr Gly Ser Gly Ser Gly Thr Asp Phe Thr Leu Thr Ile Ser
1               5                   10                  15

Ser Leu Gln Ala Glu Asp Val Ala Val Tyr Tyr Cys Gln
            20                  25

<210> SEQ ID NO 155
<211> LENGTH: 5
<212> TYPE: PRT
<213> ORGANISM: Homo sapiens

<400> SEQUENCE: 155

Tyr Ser Tyr Pro Leu
1               5

<210> SEQ ID NO 156
<211> LENGTH: 11
<212> TYPE: PRT
<213> ORGANISM: Homo sapiens

<400> SEQUENCE: 156

Thr Phe Gly Gln Gly Thr Lys Leu Glu Ile Lys
1               5                   10

<210> SEQ ID NO 157
<211> LENGTH: 21
<212> TYPE: PRT

```
<213> ORGANISM: Homo sapiens

<400> SEQUENCE: 157

Val Met Thr Gln Ser Pro Ala Phe Leu Ser Val Thr Pro Gly Glu Lys
1               5                   10                  15

Val Thr Ile Thr Cys
            20

<210> SEQ ID NO 158
<211> LENGTH: 29
<212> TYPE: PRT
<213> ORGANISM: Homo sapiens

<400> SEQUENCE: 158

Arg Phe Ser Gly Ser Gly Ser Gly Thr Asp Phe Thr Leu Thr Ile Ser
1               5                   10                  15

Ser Leu Gln Ala Glu Asp Val Ala Val Tyr Tyr Cys Gln
            20                  25
```